(12) United States Patent
Misener et al.

(10) Patent No.: US 11,026,630 B2
(45) Date of Patent: *Jun. 8, 2021

(54) CONNECTOR INTERFACE FOR ECG-BASED CATHETER POSITIONING SYSTEM

(71) Applicant: C. R. Bard, Inc., Murray Hill, NJ (US)

(72) Inventors: Anthony K. Misener, Bountiful, UT (US); Zachary S. Davis, Sandy, UT (US); Jason R. Stats, Layton, UT (US)

(73) Assignee: C. R. Bard, Inc., Franklin Lakes, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/457,606

(22) Filed: Jun. 28, 2019

(65) Prior Publication Data
US 2019/0320982 A1    Oct. 24, 2019

Related U.S. Application Data

(63) Continuation of application No. 15/192,561, filed on Jun. 24, 2016, now Pat. No. 10,349,890.
(Continued)

(51) Int. Cl.
*A61B 5/04* (2006.01)
*A61B 5/00* (2006.01)
(Continued)

(52) U.S. Cl.
CPC .......... *A61B 5/6852* (2013.01); *A61B 5/062* (2013.01); *A61B 5/283* (2021.01); *A61B 5/332* (2021.01);
(Continued)

(58) Field of Classification Search
CPC ..... A61B 5/6852; A61B 5/0404; A61B 5/062; A61B 5/042; A61B 2562/227; A61M 25/01; A61M 2230/04
See application file for complete search history.

(56) References Cited

U.S. PATENT DOCUMENTS

| 2,619,515 A | 11/1952 | Doane |
| 2,646,086 A | 7/1953 | Smith |

(Continued)

FOREIGN PATENT DOCUMENTS

| AU | 642647 B2 | 10/1993 |
| AU | 1860597 B2 | 6/1999 |

(Continued)

OTHER PUBLICATIONS

U.S. Appl. No. 15/365,698, filed Nov. 30, 2016 Non-Final Office Action dated Apr. 18, 2019.
(Continued)

*Primary Examiner* — Amanda K Hulbert
*Assistant Examiner* — Natasha Patel
(74) *Attorney, Agent, or Firm* — Rutan & Tucker LLP

(57) ABSTRACT

A connector interface configured to enable component interconnection with a location sensor of a catheter placement system is disclosed. The catheter placement system is configured to assist a clinician in positioning a catheter in a desired location within a body of a patient. In one embodiment, the location sensor assembly comprises a location sensor body for temporary placement on a portion of the patient body, and a connector interface. The connector interface is configured to removably attach to the location sensor and provide a plurality of electrically conductive pathways between the location sensor and additional components of the catheter placement system to enable the additional components to operably connect with the location sensor. The connector interface further includes a first connector configured to operably connect with a second connector of one of the additional components of the catheter placement system through a drape interposed between the first and second connectors.

11 Claims, 15 Drawing Sheets

Related U.S. Application Data

(60) Provisional application No. 62/185,477, filed on Jun. 26, 2015.

(51) Int. Cl.
*A61B 5/06* (2006.01)
*A61M 25/01* (2006.01)
*A61B 5/283* (2021.01)
*A61B 5/332* (2021.01)

(52) U.S. Cl.
CPC ....... *A61M 25/01* (2013.01); *A61B 2562/227* (2013.01); *A61M 2230/04* (2013.01)

(56) References Cited

U.S. PATENT DOCUMENTS

| | | |
|---|---|---|
| 3,133,244 A | 5/1964 | Wojtulewicz |
| 3,297,020 A | 1/1967 | Mathiesen |
| 3,625,200 A | 12/1971 | Muller |
| 3,674,014 A | 7/1972 | Tillander |
| 3,795,855 A | 3/1974 | Browning |
| 3,817,241 A | 6/1974 | Grausz |
| 3,847,157 A | 11/1974 | Caillouette et al. |
| 3,868,565 A | 2/1975 | Kuipers |
| 3,896,373 A | 7/1975 | Zelby |
| 3,902,501 A | 9/1975 | Citron et al. |
| 3,986,373 A | 10/1976 | Goodlaxson |
| 3,995,623 A | 12/1976 | Blake et al. |
| 4,003,369 A | 1/1977 | Heilman et al. |
| 4,063,561 A | 12/1977 | McKenna |
| 4,072,146 A | 2/1978 | Howes |
| 4,114,601 A | 9/1978 | Abels |
| 4,149,535 A | 4/1979 | Voider |
| 4,161,943 A | 7/1979 | Nogier |
| 4,173,228 A | 11/1979 | Van Steenwyk et al. |
| 4,175,566 A | 11/1979 | Millar |
| 4,181,120 A | 1/1980 | Kunii et al. |
| 4,224,949 A | 9/1980 | Scott et al. |
| 4,244,362 A | 1/1981 | Anderson |
| 4,289,139 A | 9/1981 | Enjoji et al. |
| 4,317,078 A | 2/1982 | Weed et al. |
| 4,327,722 A | 5/1982 | Groshong et al. |
| 4,327,723 A | 5/1982 | Frankhouser |
| 4,362,166 A | 12/1982 | Furler et al. |
| 4,365,639 A | 12/1982 | Goldreyer |
| 4,380,237 A | 4/1983 | Newbower |
| 4,407,294 A | 10/1983 | Vilkomerson |
| 4,417,886 A | 11/1983 | Frankhouser et al. |
| 4,429,693 A | 2/1984 | Blake et al. |
| 4,431,005 A | 2/1984 | McCormick |
| 4,431,214 A | 2/1984 | Buffington |
| 4,445,501 A | 5/1984 | Bresler |
| 4,459,854 A | 7/1984 | Richardson et al. |
| 4,469,106 A | 9/1984 | Harui |
| 4,483,343 A | 11/1984 | Beyer et al. |
| 4,491,137 A | 1/1985 | Jingu |
| 4,565,201 A | 1/1986 | Lass |
| 4,572,198 A | 2/1986 | Codrington |
| 4,577,634 A | 3/1986 | Gessman |
| 4,582,067 A | 4/1986 | Silverstein et al. |
| 4,587,975 A | 5/1986 | Salo et al. |
| 4,588,394 A | 5/1986 | Schulte et al. |
| 4,593,687 A | 6/1986 | Gray |
| 4,595,012 A | 6/1986 | Webler et al. |
| 4,601,706 A | 7/1986 | Aillon |
| 4,608,989 A | 9/1986 | Drue |
| 4,608,992 A | 9/1986 | Hakim et al. |
| 4,619,247 A | 10/1986 | Inoue et al. |
| 4,622,644 A | 11/1986 | Hansen |
| 4,644,960 A | 2/1987 | Johans |
| 4,652,820 A | 3/1987 | Maresca |
| 4,660,571 A | 4/1987 | Hess et al. |
| 4,665,925 A | 5/1987 | Millar |
| 4,667,230 A | 5/1987 | Arakawa et al. |
| 4,674,518 A | 6/1987 | Salo |
| 4,676,249 A | 6/1987 | Arenas et al. |
| 4,681,106 A | 7/1987 | Kensey et al. |
| 4,681,117 A | 7/1987 | Brodman et al. |
| 4,688,578 A | 8/1987 | Takano et al. |
| 4,692,148 A | 9/1987 | Kantrowitz et al. |
| 4,697,595 A | 10/1987 | Breyer et al. |
| 4,700,997 A | 10/1987 | Strand |
| 4,706,681 A | 11/1987 | Breyer et al. |
| 4,710,708 A | 12/1987 | Rorden et al. |
| 4,733,669 A | 3/1988 | Segal |
| 4,737,794 A | 4/1988 | Jones |
| 4,741,356 A | 5/1988 | Letzo et al. |
| 4,742,356 A | 5/1988 | Kuipers |
| 4,753,247 A | 6/1988 | Kirsner |
| 4,770,185 A | 9/1988 | Silverstein et al. |
| 4,771,788 A | 9/1988 | Millar |
| 4,781,685 A | 11/1988 | Lehmann et al. |
| 4,784,646 A | 11/1988 | Feingold |
| 4,787,070 A | 11/1988 | Suzuki et al. |
| 4,787,396 A | 11/1988 | Pidorenko |
| 4,790,809 A | 12/1988 | Kuntz |
| 4,793,361 A | 12/1988 | DuFault |
| 4,794,930 A | 1/1989 | Machida et al. |
| 4,796,632 A | 1/1989 | Boyd et al. |
| 4,798,588 A | 1/1989 | Aillon |
| 4,798,598 A | 1/1989 | Bonello et al. |
| 4,809,681 A | 3/1989 | Kantrowitz et al. |
| 4,809,713 A | 3/1989 | Grayzel |
| 4,813,729 A | 3/1989 | Speckhart |
| 4,821,731 A | 4/1989 | Martinelli et al. |
| 4,834,709 A | 5/1989 | Banning et al. |
| 4,836,214 A | 6/1989 | Sramek |
| 4,840,182 A | 6/1989 | Carlson |
| 4,840,622 A | 6/1989 | Hardy |
| 4,841,977 A | 6/1989 | Griffith et al. |
| 4,849,692 A | 7/1989 | Blood |
| 4,850,358 A | 7/1989 | Millar |
| 4,852,580 A | 8/1989 | Wood |
| 4,856,317 A | 8/1989 | Pidorenko et al. |
| 4,856,529 A | 8/1989 | Segal |
| 4,860,757 A | 8/1989 | Lynch et al. |
| 4,867,169 A | 9/1989 | Machida et al. |
| 4,869,263 A | 9/1989 | Segal et al. |
| 4,869,718 A | 9/1989 | Brader |
| 4,873,987 A | 10/1989 | Djordjevich et al. |
| 4,887,606 A | 12/1989 | Yook et al. |
| 4,887,615 A | 12/1989 | Taylor |
| 4,889,128 A | 12/1989 | Millar |
| 4,899,756 A | 2/1990 | Sonek |
| 4,901,725 A | 2/1990 | Nappholz et al. |
| 4,905,698 A | 3/1990 | Strohl, Jr. et al. |
| 4,911,173 A | 3/1990 | Terwilliger |
| 4,911,174 A | 3/1990 | Pederson et al. |
| 4,917,669 A | 4/1990 | Bonaldo |
| 4,924,870 A | 5/1990 | Wlodarczyk et al. |
| 4,943,770 A | 7/1990 | Ashley-Rollman et al. |
| 4,945,305 A | 7/1990 | Blood |
| 4,947,852 A | 8/1990 | Nassi et al. |
| 4,957,110 A | 9/1990 | Vogel et al. |
| 4,957,111 A | 9/1990 | Millar |
| 4,961,433 A | 10/1990 | Christian |
| 4,966,148 A | 10/1990 | Millar |
| 4,967,753 A | 11/1990 | Haase et al. |
| 4,977,886 A | 12/1990 | Takehana et al. |
| 4,989,608 A | 2/1991 | Ratner |
| 4,989,610 A | 2/1991 | Patton et al. |
| 4,995,396 A | 2/1991 | Inaba et al. |
| 4,998,916 A | 3/1991 | Hammerslag et al. |
| 5,004,456 A | 4/1991 | Botterbusch et al. |
| 5,005,592 A | 4/1991 | Cartmell |
| 5,016,173 A | 5/1991 | Kenet et al. |
| 5,025,799 A | 6/1991 | Wilson |
| 5,029,585 A | 7/1991 | Lieber et al. |
| 5,040,548 A | 8/1991 | Yock |
| 5,042,486 A | 8/1991 | Pfeiler et al. |
| 5,045,071 A | 9/1991 | McCormick et al. |
| 5,046,497 A | 9/1991 | Millar |
| 5,050,607 A | 9/1991 | Bradley et al. |
| 5,057,095 A | 10/1991 | Fabian |

(56) References Cited

U.S. PATENT DOCUMENTS

| | | |
|---|---|---|
| 5,058,583 A | 10/1991 | Geddes et al. |
| 5,058,595 A | 10/1991 | Kern |
| 5,067,489 A | 11/1991 | Lind |
| 5,076,278 A | 12/1991 | Vilkomerson et al. |
| 5,078,140 A | 1/1992 | Kwoh |
| 5,078,148 A | 1/1992 | Nassi et al. |
| 5,078,149 A | 1/1992 | Katsumata et al. |
| 5,078,678 A | 1/1992 | Katims |
| 5,078,714 A | 1/1992 | Katims |
| 5,084,022 A | 1/1992 | Claude |
| 5,092,341 A | 3/1992 | Kelen |
| 5,099,845 A | 3/1992 | Besz et al. |
| 5,099,850 A | 3/1992 | Matsui et al. |
| 5,100,387 A | 3/1992 | Ng |
| 5,105,829 A | 4/1992 | Fabian et al. |
| 5,109,862 A | 5/1992 | Kelen et al. |
| 5,114,401 A | 5/1992 | Stuart et al. |
| 5,121,750 A | 6/1992 | Katims |
| 5,125,410 A | 6/1992 | Misono et al. |
| 5,134,370 A | 7/1992 | Jefferts et al. |
| 5,144,955 A | 9/1992 | O'Hara |
| 5,146,151 A | 9/1992 | Korn |
| 5,156,151 A | 10/1992 | Imran |
| 5,158,086 A | 10/1992 | Brown et al. |
| 5,160,342 A | 11/1992 | Reger et al. |
| 5,161,536 A | 11/1992 | Vilkomerson et al. |
| 5,174,295 A | 12/1992 | Christian et al. |
| 5,174,299 A | 12/1992 | Nelson |
| 5,184,601 A | 2/1993 | Putman |
| 5,184,627 A | 2/1993 | de Toledo |
| 5,190,045 A | 3/1993 | Frazin |
| 5,202,985 A | 4/1993 | Goyal |
| 5,205,830 A | 4/1993 | Dassa et al. |
| 5,211,165 A | 5/1993 | Dumoulin et al. |
| 5,211,636 A | 5/1993 | Mische |
| 5,212,988 A | 5/1993 | White et al. |
| 5,214,615 A | 5/1993 | Bauer |
| 5,217,026 A | 6/1993 | Stoy et al. |
| 5,220,924 A | 6/1993 | Frazin |
| 5,233,994 A | 8/1993 | Shmulewitz |
| 5,235,987 A | 8/1993 | Wolfe |
| 5,239,464 A | 8/1993 | Blair et al. |
| 5,240,004 A | 8/1993 | Walinsky et al. |
| 5,243,995 A | 9/1993 | Maier |
| 5,246,007 A | 9/1993 | Frisbie et al. |
| 5,246,426 A | 9/1993 | Lewis et al. |
| 5,247,171 A | 9/1993 | Wlodarczyk et al. |
| 5,251,635 A | 10/1993 | Dumoulin et al. |
| 5,255,680 A | 10/1993 | Darrow et al. |
| 5,257,636 A | 11/1993 | White |
| 5,257,979 A | 11/1993 | Jagpal |
| 5,261,409 A | 11/1993 | Dardel |
| 5,265,610 A | 11/1993 | Darrow et al. |
| 5,265,614 A | 11/1993 | Hayakawa et al. |
| 5,267,569 A | 12/1993 | Lienhard |
| 5,269,306 A | 12/1993 | Warnking et al. |
| 5,270,810 A | 12/1993 | Nishimura |
| 5,271,404 A | 12/1993 | Corl et al. |
| 5,273,025 A | 12/1993 | Sakiyama et al. |
| 5,273,042 A | 12/1993 | Lynch et al. |
| 5,274,551 A | 12/1993 | Corby, Jr. |
| 5,275,053 A | 1/1994 | Wlodarczyk et al. |
| 5,279,129 A | 1/1994 | Ito |
| 5,279,607 A | 1/1994 | Schentag et al. |
| 5,280,786 A | 1/1994 | Wlodarczyk et al. |
| 5,287,331 A | 2/1994 | Schindel et al. |
| 5,289,373 A | 2/1994 | Zarge et al. |
| 5,292,342 A | 3/1994 | Nelson et al. |
| 5,307,072 A | 4/1994 | Jones, Jr. |
| 5,311,871 A | 5/1994 | Yock |
| 5,313,949 A | 5/1994 | Yock |
| 5,318,025 A | 6/1994 | Dumoulin et al. |
| 5,325,293 A | 6/1994 | Dorne |
| 5,325,860 A | 7/1994 | Seward et al. |
| 5,325,873 A | 7/1994 | Hirschi et al. |
| 5,330,496 A | 7/1994 | Alferness |
| 5,331,491 A | 7/1994 | Hayakawa et al. |
| 5,331,966 A | 7/1994 | Bennett et al. |
| 5,333,614 A | 8/1994 | Feiring |
| 5,337,678 A | 8/1994 | Grout |
| 5,341,807 A | 8/1994 | Nardella |
| 5,343,865 A | 9/1994 | Gardineer et al. |
| 5,345,940 A | 9/1994 | Seward et al. |
| 5,348,020 A | 9/1994 | Hutson |
| 5,350,352 A | 9/1994 | Buchholtz et al. |
| 5,357,961 A | 10/1994 | Fields et al. |
| 5,365,935 A | 11/1994 | Righter et al. |
| 5,366,443 A | 11/1994 | Eggers et al. |
| 5,368,048 A | 11/1994 | Stoy et al. |
| 5,375,596 A | 12/1994 | Twiss et al. |
| 5,376,083 A | 12/1994 | Mische |
| 5,377,678 A | 1/1995 | Dumoulin et al. |
| 5,385,053 A | 1/1995 | Wlodarczyk et al. |
| 5,385,146 A | 1/1995 | Goldreyer |
| 5,391,199 A | 2/1995 | Ben-Haim |
| 5,394,876 A | 3/1995 | Ma |
| 5,394,877 A | 3/1995 | Orr et al. |
| 5,395,366 A | 3/1995 | D'Andrea et al. |
| 5,398,683 A | 3/1995 | Edwards et al. |
| 5,398,691 A | 3/1995 | Martin et al. |
| 5,411,485 A | 5/1995 | Tennican et al. |
| 5,413,107 A | 5/1995 | Oakley et al. |
| 5,417,208 A | 5/1995 | Winkler |
| 5,417,701 A | 5/1995 | Holmes |
| 5,422,478 A | 6/1995 | Wlodarczyk et al. |
| 5,423,334 A | 6/1995 | Jordan |
| 5,423,877 A | 6/1995 | Mackey |
| 5,425,367 A | 6/1995 | Shapiro et al. |
| 5,425,370 A | 6/1995 | Vilkomerson |
| 5,425,382 A | 6/1995 | Golden et al. |
| 5,427,114 A | 6/1995 | Colliver et al. |
| 5,429,132 A | 7/1995 | Guy et al. |
| 5,429,617 A | 7/1995 | Hammersmark et al. |
| 5,431,641 A | 7/1995 | Grozinger et al. |
| 5,433,729 A | 7/1995 | Adams et al. |
| 5,437,276 A | 8/1995 | Takada |
| 5,437,277 A | 8/1995 | Dumoulin et al. |
| 5,438,873 A | 8/1995 | Wlodarczyk et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,445,166 A | 8/1995 | Taylor |
| 5,450,846 A | 9/1995 | Goldreyer |
| 5,453,575 A | 9/1995 | O'Donnell et al. |
| 5,453,576 A | 9/1995 | Krivitski |
| 5,456,256 A | 10/1995 | Schneider et al. |
| 5,456,718 A | 10/1995 | Szymaitis |
| 5,464,016 A | 11/1995 | Nicholas et al. |
| 5,474,065 A | 12/1995 | Meathrel et al. |
| 5,476,090 A | 12/1995 | Kishi |
| 5,480,422 A | 1/1996 | Ben-Haim |
| 5,487,729 A | 1/1996 | Avellanet et al. |
| 5,490,522 A | 2/1996 | Dardel |
| 5,492,538 A | 2/1996 | Johlin, Jr. |
| 5,494,038 A | 2/1996 | Wang et al. |
| 5,500,011 A | 3/1996 | Desai |
| 5,500,012 A | 3/1996 | Brucker et al. |
| 5,505,205 A | 4/1996 | Solomon et al. |
| 5,509,822 A | 4/1996 | Negus et al. |
| 5,513,637 A | 5/1996 | Twiss et al. |
| 5,515,160 A | 5/1996 | Schulz et al. |
| 5,515,853 A | 5/1996 | Smith et al. |
| 5,517,989 A | 5/1996 | Frisbie et al. |
| 5,522,878 A | 6/1996 | Montecalvo et al. |
| 5,522,880 A | 6/1996 | Barone et al. |
| 5,526,812 A | 6/1996 | Dumoulin et al. |
| 5,531,664 A | 7/1996 | Adachi et al. |
| 5,536,248 A | 7/1996 | Weaver et al. |
| 5,540,230 A | 7/1996 | Vilkomerson |
| 5,540,681 A | 7/1996 | Strul et al. |
| 5,542,938 A | 8/1996 | Avellanet et al. |
| 5,546,949 A | 8/1996 | Frazin et al. |
| 5,546,951 A | 8/1996 | Ben-Haim |
| 5,555,618 A | 9/1996 | Winkler |

(56) References Cited

U.S. PATENT DOCUMENTS

| | | |
|---|---|---|
| 5,558,091 A | 9/1996 | Acker et al. |
| 5,568,809 A | 10/1996 | Ben-haim |
| D375,450 S | 11/1996 | Bidwell et al. |
| 5,570,671 A | 11/1996 | Hickey |
| 5,575,291 A | 11/1996 | Hayakawa et al. |
| 5,588,442 A | 12/1996 | Scovil et al. |
| 5,592,939 A | 1/1997 | Martinelli |
| 5,598,846 A | 2/1997 | Peszynski |
| 5,599,299 A | 2/1997 | Weaver et al. |
| 5,600,330 A | 2/1997 | Blood |
| 5,603,333 A | 2/1997 | Konings |
| 5,606,981 A | 3/1997 | Tartacower et al. |
| 5,610,967 A | 3/1997 | Moorman et al. |
| 5,617,866 A | 4/1997 | Marian, Jr. |
| 5,622,169 A | 4/1997 | Golden et al. |
| 5,622,170 A | 4/1997 | Schulz |
| 5,622,184 A | 4/1997 | Ashby et al. |
| 5,623,931 A | 4/1997 | Wung et al. |
| 5,624,430 A | 4/1997 | Eton et al. |
| 5,626,554 A | 5/1997 | Ryaby et al. |
| 5,626,870 A | 5/1997 | Monshipouri et al. |
| 5,630,419 A | 5/1997 | Ranalletta |
| 5,638,819 A | 6/1997 | Manwaring et al. |
| 5,640,967 A | 6/1997 | Fine et al. |
| 5,644,612 A | 7/1997 | Moorman et al. |
| 5,645,065 A | 7/1997 | Shapiro et al. |
| 5,651,047 A | 7/1997 | Moorman et al. |
| 5,654,864 A | 8/1997 | Ritter et al. |
| D383,968 S | 9/1997 | Bidwell et al. |
| 5,662,115 A | 9/1997 | Torp et al. |
| 5,665,103 A | 9/1997 | Lafontaine et al. |
| 5,665,477 A | 9/1997 | Meathrel et al. |
| 5,666,473 A | 9/1997 | Wallace |
| 5,666,958 A | 9/1997 | Rothenberg et al. |
| 5,669,383 A | 9/1997 | Johnson |
| 5,669,388 A | 9/1997 | Vilkomerson |
| 5,676,159 A | 10/1997 | Navis |
| 5,676,673 A | 10/1997 | Ferre et al. |
| 5,682,890 A | 11/1997 | Kormos et al. |
| 5,691,898 A | 11/1997 | Rosenberg et al. |
| 5,694,945 A | 12/1997 | Ben-Haim |
| 5,695,479 A | 12/1997 | Jagpal |
| 5,697,377 A | 12/1997 | Wittkampf |
| 5,699,801 A | 12/1997 | Atalar et al. |
| 5,700,889 A | 12/1997 | Blair |
| 5,701,898 A | 12/1997 | Adam et al. |
| 5,702,433 A | 12/1997 | Taylor et al. |
| 5,711,299 A | 1/1998 | Manwaring et al. |
| 5,713,362 A | 2/1998 | Vilkomerson |
| 5,713,363 A | 2/1998 | Seward et al. |
| 5,713,858 A | 2/1998 | Heruth et al. |
| 5,713,946 A | 2/1998 | Ben-Haim |
| 5,715,817 A | 2/1998 | Stevens-Wright et al. |
| 5,716,389 A | 2/1998 | Walinsky et al. |
| 5,718,241 A | 2/1998 | Ben-Haim et al. |
| D391,838 S | 3/1998 | Bidwell et al. |
| 5,722,412 A | 3/1998 | Pflugrath et al. |
| 5,727,550 A | 3/1998 | Montecalvo |
| 5,727,552 A | 3/1998 | Ryan |
| 5,727,553 A | 3/1998 | Saad |
| 5,729,055 A | 3/1998 | Manning |
| 5,729,129 A | 3/1998 | Acker |
| 5,729,584 A | 3/1998 | Moorman et al. |
| 5,730,129 A | 3/1998 | Darrow et al. |
| 5,731,996 A | 3/1998 | Gilbert |
| 5,733,323 A | 3/1998 | Buck et al. |
| 5,738,096 A | 4/1998 | Ben-Haim |
| 5,740,808 A | 4/1998 | Panescu et al. |
| 5,742,394 A | 4/1998 | Hansen |
| 5,744,953 A | 4/1998 | Hansen |
| 5,748,767 A | 5/1998 | Raab |
| 5,749,835 A | 5/1998 | Glantz |
| 5,749,938 A | 5/1998 | Coombs |
| 5,751,785 A | 5/1998 | Moorman et al. |
| 5,752,513 A | 5/1998 | Acker et al. |
| 5,758,650 A | 6/1998 | Miller et al. |
| 5,762,064 A | 6/1998 | Polvani |
| 5,767,669 A | 6/1998 | Hansen et al. |
| 5,767,960 A | 6/1998 | Orman |
| 5,769,786 A | 6/1998 | Wiegel |
| 5,769,843 A | 6/1998 | Abela et al. |
| 5,769,881 A | 6/1998 | Schroeppel et al. |
| 5,771,896 A | 6/1998 | Sliwa, Jr. et al. |
| 5,775,322 A | 7/1998 | Silverstein et al. |
| 5,775,332 A | 7/1998 | Goldman |
| 5,776,064 A | 7/1998 | Kalfas et al. |
| 5,776,080 A | 7/1998 | Thome et al. |
| 5,779,638 A | 7/1998 | Vesely et al. |
| 5,782,767 A | 7/1998 | Pretlow, III |
| 5,782,773 A | 7/1998 | Kuo et al. |
| 5,785,657 A | 7/1998 | Breyer et al. |
| 5,792,055 A | 8/1998 | McKinnon |
| 5,795,297 A | 8/1998 | Daigle |
| 5,795,298 A | 8/1998 | Vesely et al. |
| 5,795,632 A | 8/1998 | Buchalter |
| 5,797,849 A | 8/1998 | Vesely et al. |
| 5,800,352 A | 9/1998 | Ferre et al. |
| 5,800,410 A | 9/1998 | Gawreluk |
| 5,800,497 A | 9/1998 | Bakels et al. |
| 5,803,089 A | 9/1998 | Ferre et al. |
| 5,810,733 A | 9/1998 | Van Creveld et al. |
| RE35,924 E | 10/1998 | Winkler |
| 5,817,022 A | 10/1998 | Vesely |
| 5,817,024 A | 10/1998 | Ogle et al. |
| 5,820,549 A | 10/1998 | Marian, Jr. |
| 5,820,560 A | 10/1998 | Sinderby et al. |
| 5,824,031 A | 10/1998 | Cookston et al. |
| 5,827,192 A | 10/1998 | Gopakumaran et al. |
| 5,829,444 A | 11/1998 | Ferre et al. |
| 5,830,145 A | 11/1998 | Tenhoff |
| 5,831,260 A | 11/1998 | Hansen |
| 5,833,608 A | 11/1998 | Acker |
| 5,833,622 A | 11/1998 | Meathrel et al. |
| 5,835,561 A | 11/1998 | Moorman et al. |
| 5,836,882 A | 11/1998 | Frazin |
| 5,836,990 A | 11/1998 | Li |
| 5,840,024 A | 11/1998 | Taniguchi et al. |
| 5,840,025 A | 11/1998 | Ben-Haim |
| 5,840,030 A | 11/1998 | Ferek-Petric et al. |
| 5,840,031 A | 11/1998 | Crowley |
| 5,842,986 A | 12/1998 | Avrin et al. |
| 5,842,998 A | 12/1998 | Gopakumaran et al. |
| 5,843,076 A | 12/1998 | Webster, Jr. et al. |
| 5,843,153 A | 12/1998 | Johnston et al. |
| 5,844,140 A | 12/1998 | Seale |
| 5,846,198 A | 12/1998 | Killmann |
| 5,851,218 A | 12/1998 | Lev |
| 5,855,553 A | 1/1999 | Tajima et al. |
| 5,859,893 A | 1/1999 | Moorman et al. |
| 5,865,748 A | 2/1999 | Co et al. |
| 5,868,673 A | 2/1999 | Vesely |
| 5,873,822 A | 2/1999 | Ferre et al. |
| 5,876,328 A | 3/1999 | Fox et al. |
| 5,879,297 A | 3/1999 | Haynor et al. |
| 5,893,363 A | 4/1999 | Little et al. |
| 5,897,495 A | 4/1999 | Aida et al. |
| 5,899,860 A | 5/1999 | Pfeiffer et al. |
| 5,902,238 A | 5/1999 | Golden et al. |
| 5,907,487 A | 5/1999 | Rosenberg et al. |
| 5,908,385 A | 6/1999 | Chechelski et al. |
| 5,908,387 A | 6/1999 | LeFree et al. |
| 5,910,113 A | 6/1999 | Pruter |
| 5,910,120 A | 6/1999 | Kim et al. |
| 5,913,820 A | 6/1999 | Bladen et al. |
| 5,913,830 A | 6/1999 | Miles |
| 5,919,141 A | 7/1999 | Money et al. |
| 5,919,170 A | 7/1999 | Woessner |
| 5,928,145 A | 7/1999 | Ocali et al. |
| 5,929,607 A | 7/1999 | Rosenberg et al. |
| 5,931,788 A | 8/1999 | Keen et al. |
| 5,931,818 A | 8/1999 | Werp et al. |
| 5,931,863 A | 8/1999 | Griffin, III et al. |
| 5,935,160 A | 8/1999 | Auricchio et al. |
| 5,941,858 A | 8/1999 | Johnson |

(56) References Cited

U.S. PATENT DOCUMENTS

| | | |
|---|---|---|
| 5,941,889 A | 8/1999 | Cermak |
| 5,941,904 A | 8/1999 | Johnston et al. |
| 5,944,022 A | 8/1999 | Nardella et al. |
| 5,944,023 A | 8/1999 | Johnson et al. |
| 5,951,472 A | 9/1999 | Van Vaals et al. |
| 5,951,598 A | 9/1999 | Bishay et al. |
| 5,953,683 A | 9/1999 | Hansen et al. |
| 5,957,857 A | 9/1999 | Hartley |
| 5,961,923 A | 10/1999 | Nova et al. |
| 5,967,978 A | 10/1999 | Littmann et al. |
| 5,967,980 A | 10/1999 | Ferre et al. |
| 5,967,991 A | 10/1999 | Gardineer et al. |
| 5,969,722 A | 10/1999 | Palm |
| 5,970,119 A | 10/1999 | Hofmann |
| 5,971,933 A | 10/1999 | Gopakumaran et al. |
| 5,971,983 A | 10/1999 | Lesh |
| 5,978,705 A | 11/1999 | KenKnight et al. |
| 5,983,126 A | 11/1999 | Wittkampf |
| 5,984,908 A | 11/1999 | Davis et al. |
| 5,991,693 A | 11/1999 | Zalewski |
| 5,997,473 A | 12/1999 | Taniguchi et al. |
| 5,997,481 A | 12/1999 | Adams et al. |
| 6,006,123 A | 12/1999 | Nguyen et al. |
| 6,011,988 A | 1/2000 | Lynch et al. |
| 6,014,473 A | 1/2000 | Hossack et al. |
| 6,014,580 A | 1/2000 | Blume et al. |
| 6,015,414 A | 1/2000 | Werp et al. |
| 6,017,496 A | 1/2000 | Nova et al. |
| 6,019,724 A | 2/2000 | Gronningsaeter et al. |
| 6,019,725 A | 2/2000 | Vesely et al. |
| 6,022,342 A | 2/2000 | Mukherjee |
| 6,023,638 A | 2/2000 | Swanson |
| 6,026,312 A | 2/2000 | Shemwell et al. |
| 6,031,765 A | 2/2000 | Lee et al. |
| 6,032,070 A | 2/2000 | Flock et al. |
| 6,039,694 A | 3/2000 | Larson et al. |
| 6,050,718 A | 4/2000 | Schena et al. |
| 6,052,610 A | 4/2000 | Koch |
| 6,052,618 A | 4/2000 | Dahlke et al. |
| D424,693 S | 5/2000 | Pruter |
| 6,058,323 A | 5/2000 | Lemelson |
| 6,059,718 A | 5/2000 | Taniguchi et al. |
| 6,060,970 A | 5/2000 | Bell |
| 6,063,032 A | 5/2000 | Grunwald |
| 6,064,905 A | 5/2000 | Webster, Jr. et al. |
| 6,066,094 A | 5/2000 | Ben-Haim |
| 6,068,599 A | 5/2000 | Saito et al. |
| 6,073,043 A | 6/2000 | Schneider |
| 6,074,367 A | 6/2000 | Hubbell |
| 6,075,442 A | 6/2000 | Welch |
| 6,076,007 A | 6/2000 | England et al. |
| 6,081,737 A | 6/2000 | Shah |
| 6,082,366 A | 7/2000 | Andra et al. |
| 6,083,170 A | 7/2000 | Ben-Haim |
| 6,099,524 A | 8/2000 | Lipson et al. |
| 6,100,026 A | 8/2000 | Nova et al. |
| 6,102,044 A | 8/2000 | Naidyhorski |
| 6,102,862 A | 8/2000 | Grunwald et al. |
| 6,107,699 A | 8/2000 | Swanson |
| 6,112,111 A | 8/2000 | Glantz |
| 6,112,115 A | 8/2000 | Feldman et al. |
| 6,113,504 A | 9/2000 | Kuesters |
| 6,115,624 A | 9/2000 | Lewis et al. |
| 6,120,445 A | 9/2000 | Grunwald |
| 6,122,538 A | 9/2000 | Sliwa, Jr. et al. |
| 6,128,174 A | 10/2000 | Ritter et al. |
| 6,129,668 A | 10/2000 | Haynor et al. |
| 6,129,724 A | 10/2000 | Fleischman et al. |
| 6,132,378 A | 10/2000 | Marino |
| 6,132,379 A | 10/2000 | Patacsil et al. |
| 6,135,961 A | 10/2000 | Pflugrath et al. |
| 6,136,274 A | 10/2000 | Nova et al. |
| 6,138,681 A | 10/2000 | Chen et al. |
| 6,139,496 A | 10/2000 | Chen et al. |
| 6,139,502 A | 10/2000 | Fredriksen |
| 6,139,540 A | 10/2000 | Rost et al. |
| 6,144,300 A | 11/2000 | Dames |
| 6,148,823 A | 11/2000 | Hastings |
| 6,152,933 A | 11/2000 | Werp et al. |
| 6,157,853 A | 12/2000 | Blume et al. |
| 6,165,144 A | 12/2000 | Talish et al. |
| 6,165,977 A | 12/2000 | Mochly-Rosen |
| 6,166,496 A | 12/2000 | Lys et al. |
| 6,166,806 A | 12/2000 | Tjin |
| 6,167,765 B1 | 1/2001 | Weitzel |
| 6,172,499 B1 | 1/2001 | Ashe |
| 6,173,199 B1 | 1/2001 | Gabriel |
| 6,173,715 B1 | 1/2001 | Sinanan et al. |
| 6,175,756 B1 | 1/2001 | Ferre et al. |
| 6,176,829 B1 | 1/2001 | Vilkomerson |
| 6,187,744 B1 | 2/2001 | Rooney |
| 6,190,370 B1 | 2/2001 | Tsui |
| 6,191,136 B1 | 2/2001 | Marban |
| 6,193,743 B1 | 2/2001 | Brayton et al. |
| 6,197,001 B1 | 3/2001 | Wilson et al. |
| 6,200,305 B1 | 3/2001 | Berthiaume et al. |
| 6,203,499 B1 | 3/2001 | Imling et al. |
| 6,208,884 B1 | 3/2001 | Kumar et al. |
| 6,211,626 B1 | 4/2001 | Lys et al. |
| 6,211,666 B1 | 4/2001 | Acker |
| 6,212,426 B1 | 4/2001 | Swanson |
| 6,212,430 B1 | 4/2001 | Kung |
| 6,216,027 B1 | 4/2001 | Willis et al. |
| 6,216,028 B1 | 4/2001 | Haynor et al. |
| 6,216,029 B1 | 4/2001 | Paltieli |
| 6,217,517 B1 | 4/2001 | Grunwald |
| 6,223,087 B1 | 4/2001 | Williams |
| 6,226,547 B1 | 5/2001 | Lockhart et al. |
| 6,230,042 B1 | 5/2001 | Slettenmark |
| 6,230,046 B1 | 5/2001 | Crane et al. |
| 6,231,518 B1 | 5/2001 | Grabek et al. |
| 6,233,476 B1 | 5/2001 | Strommer et al. |
| 6,233,994 B1 | 5/2001 | Roy et al. |
| 6,236,883 B1 | 5/2001 | Ciaccio et al. |
| 6,238,344 B1 | 5/2001 | Gamelsky et al. |
| 6,241,673 B1 | 6/2001 | Williams |
| 6,246,231 B1 | 6/2001 | Ashe |
| 6,246,898 B1 | 6/2001 | Vesely et al. |
| 6,248,072 B1 | 6/2001 | Murkin |
| 6,248,074 B1 | 6/2001 | Ohno et al. |
| 6,248,075 B1 | 6/2001 | McGee et al. |
| 6,249,234 B1 | 6/2001 | Ely et al. |
| 6,253,770 B1 | 7/2001 | Acker et al. |
| 6,254,543 B1 | 7/2001 | Grunwald et al. |
| 6,258,035 B1 | 7/2001 | Hoeksel et al. |
| 6,259,938 B1 | 7/2001 | Zarychta et al. |
| 6,259,941 B1 | 7/2001 | Chia et al. |
| 6,261,231 B1 | 7/2001 | Damphousse et al. |
| 6,263,230 B1 | 7/2001 | Haynor et al. |
| 6,266,550 B1 | 7/2001 | Selmon et al. |
| 6,266,551 B1 | 7/2001 | Osadchy et al. |
| 6,266,552 B1 | 7/2001 | Slettenmark |
| 6,266,563 B1 | 7/2001 | KenKnight et al. |
| 6,270,493 B1 | 8/2001 | Lalonde et al. |
| 6,271,833 B1 | 8/2001 | Rosenberg et al. |
| 6,272,371 B1 | 8/2001 | Shlomo |
| 6,272,374 B1 | 8/2001 | Flock et al. |
| 6,275,258 B1 | 8/2001 | Chim |
| 6,275,724 B1 | 8/2001 | Dickinson et al. |
| 6,277,077 B1 | 8/2001 | Brisken et al. |
| 6,284,459 B1 | 9/2001 | Nova et al. |
| 6,285,898 B1 | 9/2001 | Ben-Haim |
| 6,287,259 B1 | 9/2001 | Grunwald |
| 6,287,260 B1 | 9/2001 | Hascoet et al. |
| 6,288,704 B1 | 9/2001 | Flack et al. |
| 6,292,678 B1 | 9/2001 | Hall et al. |
| 6,292,680 B1 | 9/2001 | Somogyi et al. |
| 6,292,901 B1 | 9/2001 | Lys et al. |
| 6,293,955 B1 | 9/2001 | Houser et al. |
| 6,296,604 B1 | 10/2001 | Garibaldi et al. |
| 6,298,261 B1 | 10/2001 | Rex |
| 6,304,768 B1 | 10/2001 | Blume et al. |
| 6,306,097 B1 | 10/2001 | Park et al. |
| 6,306,105 B1 | 10/2001 | Rooney et al. |

(56) References Cited

U.S. PATENT DOCUMENTS

| | | | |
|---|---|---|---|
| 6,311,082 B1 | 10/2001 | Creighton, IV et al. |
| 6,315,709 B1 | 11/2001 | Garibaldi et al. |
| 6,315,727 B1 | 11/2001 | Coleman et al. |
| 6,319,668 B1 | 11/2001 | Nova et al. |
| 6,323,769 B1 | 11/2001 | Dames |
| 6,323,770 B1 | 11/2001 | Dames |
| 6,324,416 B1 | 11/2001 | Seibert |
| 6,325,540 B1 | 12/2001 | Lounsberry et al. |
| 6,325,762 B1 | 12/2001 | Tjin |
| 6,329,139 B1 | 12/2001 | Nova et al. |
| 6,329,916 B1 | 12/2001 | Dames |
| 6,330,467 B1 | 12/2001 | Creighton, IV et al. |
| 6,332,089 B1 | 12/2001 | Acker et al. |
| 6,332,874 B1 | 12/2001 | Eliasen et al. |
| 6,340,588 B1 | 1/2002 | Nova et al. |
| 6,340,868 B1 | 1/2002 | Lys et al. |
| 6,341,231 B1 | 1/2002 | Ferre et al. |
| 6,346,081 B1 | 2/2002 | Vilkomerson |
| 6,348,911 B1 | 2/2002 | Rosenberg et al. |
| 6,350,160 B1 | 2/2002 | Feuersanger et al. |
| 6,352,363 B1 | 3/2002 | Munger et al. |
| 6,354,999 B1 | 3/2002 | Dgany et al. |
| 6,355,026 B1 | 3/2002 | Mick |
| 6,356,791 B1 | 3/2002 | Westlund et al. |
| 6,360,123 B1 | 3/2002 | Kimchi et al. |
| 6,361,499 B1 | 3/2002 | Bates et al. |
| 6,364,823 B1 | 4/2002 | Garibaldi et al. |
| 6,364,839 B1 | 4/2002 | Little et al. |
| 6,366,804 B1 | 4/2002 | Mejia |
| 6,368,141 B1 | 4/2002 | VanAntwerp et al. |
| 6,368,285 B1 | 4/2002 | Osadchy et al. |
| 6,370,411 B1 | 4/2002 | Osadchy et al. |
| 6,373,240 B1 | 4/2002 | Govari |
| 6,373,388 B1 | 4/2002 | Dames |
| 6,374,134 B1 | 4/2002 | Bladen et al. |
| 6,374,670 B1 | 4/2002 | Spelman et al. |
| 6,375,606 B1 | 4/2002 | Garibaldi et al. |
| 6,375,639 B1 | 4/2002 | Duplessie et al. |
| 6,377,857 B1 | 4/2002 | Brayton et al. |
| 6,379,302 B1 | 4/2002 | Kessman et al. |
| 6,379,303 B1 | 4/2002 | Seitz et al. |
| 6,379,307 B1 | 4/2002 | Filly et al. |
| 6,381,485 B1 | 4/2002 | Hunter et al. |
| 6,385,472 B1 | 5/2002 | Hall et al. |
| 6,385,476 B1 | 5/2002 | Osadchy et al. |
| 6,398,736 B1 | 6/2002 | Seward |
| 6,398,738 B1 | 6/2002 | Millar |
| 6,401,723 B1 | 6/2002 | Garibaldi et al. |
| 6,406,422 B1 | 6/2002 | Landesberg |
| 6,406,442 B1 | 6/2002 | McFann et al. |
| 6,412,978 B1 | 7/2002 | Watanabe et al. |
| 6,412,980 B1 | 7/2002 | Lounsberry et al. |
| 6,417,839 B1 | 7/2002 | Odell |
| 6,418,332 B1 | 7/2002 | Mastrototaro et al. |
| 6,418,335 B2 | 7/2002 | Avrin et al. |
| 6,423,002 B1 | 7/2002 | Hossack |
| 6,423,050 B1 | 7/2002 | Twardowski |
| 6,427,079 B1 | 7/2002 | Schneider et al. |
| 6,428,551 B1 | 8/2002 | Hall et al. |
| 6,430,315 B1 | 8/2002 | Makram-Ebeid |
| 6,432,069 B1 | 8/2002 | Godo et al. |
| 6,438,411 B1 | 8/2002 | Guttman et al. |
| 6,442,416 B1 | 8/2002 | Schultz |
| 6,445,943 B1 | 9/2002 | Ferre et al. |
| 6,456,874 B1 | 9/2002 | Hafer et al. |
| 6,459,919 B1 | 10/2002 | Lys et al. |
| 6,463,121 B1 | 10/2002 | Milnes |
| 6,466,815 B1 | 10/2002 | Saito et al. |
| 6,471,656 B1 | 10/2002 | Shalman et al. |
| 6,471,658 B1 | 10/2002 | Daniels et al. |
| 6,471,700 B1 | 10/2002 | Burbank et al. |
| 6,473,167 B1 | 10/2002 | Odell |
| 6,474,341 B1 | 11/2002 | Hunter et al. |
| 6,475,152 B1 | 11/2002 | Kelly, Jr. et al. |
| 6,475,223 B1 | 11/2002 | Werp et al. |
| 6,477,402 B1 | 11/2002 | Lynch et al. |
| 6,484,118 B1 | 11/2002 | Govari |
| 6,487,916 B1 | 12/2002 | Gomm et al. |
| 6,491,671 B1 | 12/2002 | Larson, III et al. |
| 6,493,573 B1 | 12/2002 | Martinelli et al. |
| 6,494,832 B1 | 12/2002 | Feldman et al. |
| 6,496,715 B1 | 12/2002 | Lee et al. |
| 6,498,944 B1 | 12/2002 | Ben-Haim et al. |
| 6,500,141 B1 | 12/2002 | Irion et al. |
| 6,505,062 B1 | 1/2003 | Ritter et al. |
| 6,506,159 B2 | 1/2003 | Hascoet et al. |
| 6,507,751 B2 | 1/2003 | Blume et al. |
| 6,508,802 B1 | 1/2003 | Rosengart et al. |
| 6,511,413 B2 | 1/2003 | Landesberg |
| 6,512,958 B1 | 1/2003 | Swoyer et al. |
| 6,514,202 B2 | 2/2003 | Grunwald |
| 6,514,226 B1 | 2/2003 | Levin et al. |
| 6,514,249 B1 | 2/2003 | Maguire et al. |
| 6,515,657 B1 | 2/2003 | Zanelli |
| 6,516,212 B1 | 2/2003 | Bladen et al. |
| 6,516,231 B1 | 2/2003 | Flammang |
| 6,516,807 B1 | 2/2003 | Panescu et al. |
| 6,517,520 B2 | 2/2003 | Chang et al. |
| 6,522,906 B1 | 2/2003 | Salisbury, Jr. et al. |
| 6,522,907 B1 | 2/2003 | Bladen et al. |
| 6,522,909 B1 | 2/2003 | Garibaldi et al. |
| 6,524,303 B1 | 2/2003 | Garibaldi |
| 6,528,954 B1 | 3/2003 | Lys et al. |
| 6,528,991 B2 | 3/2003 | Ashe |
| 6,529,761 B2 | 3/2003 | Creighton, IV et al. |
| 6,529,766 B1 | 3/2003 | Guendel |
| 6,534,982 B1 | 3/2003 | Jakab |
| 6,535,625 B1 | 3/2003 | Chang et al. |
| 6,537,192 B1 | 3/2003 | Elliott et al. |
| 6,537,196 B1 | 3/2003 | Creighton, IV et al. |
| 6,538,634 B1 | 3/2003 | Chui et al. |
| 6,540,699 B1 | 4/2003 | Smith |
| 6,542,766 B2 | 4/2003 | Hall et al. |
| 6,544,251 B1 | 4/2003 | Crawford |
| 6,545,678 B1 | 4/2003 | Ohazama |
| 6,546,270 B1 | 4/2003 | Goldin et al. |
| 6,546,279 B1 | 4/2003 | Bova et al. |
| 6,546,787 B1 | 4/2003 | Schiller et al. |
| 6,552,841 B1 | 4/2003 | Lasser et al. |
| 6,556,858 B1 | 4/2003 | Zeman |
| 6,562,019 B1 | 5/2003 | Sell |
| 6,564,087 B1 | 5/2003 | Pitris et al. |
| 6,569,101 B2 | 5/2003 | Quistgaard et al. |
| 6,569,103 B2 | 5/2003 | Hoeksel et al. |
| 6,569,160 B1 | 5/2003 | Goldin et al. |
| 6,569,862 B1 | 5/2003 | Marban |
| 6,571,004 B1 | 5/2003 | Florent et al. |
| 6,574,518 B1 | 6/2003 | Lounsberry et al. |
| 6,575,908 B2 | 6/2003 | Barnes et al. |
| 6,577,080 B2 | 6/2003 | Lys et al. |
| 6,577,896 B2 | 6/2003 | Werner et al. |
| 6,584,343 B1 | 6/2003 | Ransbury et al. |
| 6,589,181 B2 | 7/2003 | Grunwald et al. |
| 6,592,565 B2 | 7/2003 | Twardowski |
| 6,593,754 B1 | 7/2003 | Steber et al. |
| 6,593,884 B1 | 7/2003 | Gilboa et al. |
| 6,597,943 B2 | 7/2003 | Taha et al. |
| 6,599,249 B1 | 7/2003 | Nordgren et al. |
| 6,607,488 B1 | 8/2003 | Jackson et al. |
| 6,610,058 B2 | 8/2003 | Flores |
| 6,611,141 B1 | 8/2003 | Schulz et al. |
| 6,615,071 B1 | 9/2003 | Casscells, III et al. |
| 6,615,155 B2 | 9/2003 | Gilboa |
| 6,616,610 B2 | 9/2003 | Steininger et al. |
| 6,618,612 B1 | 9/2003 | Acker et al. |
| 6,626,832 B1 | 9/2003 | Paltieli et al. |
| 6,626,834 B2 | 9/2003 | Dunne et al. |
| 6,626,902 B1 | 9/2003 | Kucharczyk et al. |
| 6,630,879 B1 | 10/2003 | Creighton, IV et al. |
| 6,635,027 B1 | 10/2003 | Cragg et al. |
| 6,645,148 B2 | 11/2003 | Nguyen-Dinh et al. |
| 6,648,875 B2 | 11/2003 | Simpson et al. |
| 6,649,914 B1 | 11/2003 | Moorman et al. |
| 6,652,505 B1 | 11/2003 | Tsugita |

(56) References Cited

U.S. PATENT DOCUMENTS

| | | |
|---|---|---|
| 6,652,506 B2 | 11/2003 | Bowe et al. |
| 6,654,643 B1 | 11/2003 | Schmid |
| 6,660,024 B1 | 12/2003 | Flaherty et al. |
| 6,662,034 B2 | 12/2003 | Segner et al. |
| 6,663,661 B2 | 12/2003 | Boneau |
| 6,666,828 B2 | 12/2003 | Greco et al. |
| 6,672,308 B1 | 1/2004 | Gaspari |
| 6,677,752 B1 | 1/2004 | Creighton, IV et al. |
| 6,679,857 B1 | 1/2004 | Bastia et al. |
| 6,684,176 B2 | 1/2004 | Willins et al. |
| 6,685,644 B2 | 2/2004 | Seo et al. |
| 6,687,386 B1 | 2/2004 | Ito et al. |
| 6,687,531 B1 | 2/2004 | Ferre et al. |
| 6,689,119 B1 | 2/2004 | Di Caprio et al. |
| 6,690,963 B2 | 2/2004 | Ben-Haim et al. |
| 6,690,964 B2 | 2/2004 | Bieger et al. |
| 6,690,968 B2 | 2/2004 | Mejia |
| 6,694,167 B1 | 2/2004 | Ferre et al. |
| 6,695,786 B2 | 2/2004 | Wang et al. |
| 6,701,179 B1 | 3/2004 | Martinelli et al. |
| 6,701,918 B2 | 3/2004 | Fariss et al. |
| 6,702,804 B1 | 3/2004 | Ritter et al. |
| 6,704,590 B2 | 3/2004 | Haldeman |
| 6,709,390 B1 | 3/2004 | Marie Pop |
| 6,711,429 B1 | 3/2004 | Gilboa et al. |
| 6,711,431 B2 | 3/2004 | Sarin et al. |
| 6,719,699 B2 | 4/2004 | Smith |
| 6,719,724 B1 | 4/2004 | Walker et al. |
| 6,719,756 B1 | 4/2004 | Muntermann |
| 6,720,745 B2 | 4/2004 | Lys et al. |
| 6,733,458 B1 | 5/2004 | Steins et al. |
| 6,733,473 B1 | 5/2004 | Reifart et al. |
| 6,733,511 B2 | 5/2004 | Hall et al. |
| 6,736,782 B2 | 5/2004 | Pfeiffer et al. |
| 6,738,656 B1 | 5/2004 | Ferre et al. |
| 6,740,103 B2 | 5/2004 | Hall et al. |
| 6,743,177 B2 | 6/2004 | Ito |
| 6,754,596 B2 | 6/2004 | Ashe |
| 6,754,608 B2 | 6/2004 | Svanerudh et al. |
| 6,755,789 B2 | 6/2004 | Stringer et al. |
| 6,755,816 B2 | 6/2004 | Ritter et al. |
| 6,755,822 B2 | 6/2004 | Reu et al. |
| 6,757,557 B1 | 6/2004 | Bladen et al. |
| 6,763,261 B2 | 7/2004 | Casscells, III et al. |
| 6,764,449 B2 | 7/2004 | Lee et al. |
| 6,768,496 B2 | 7/2004 | Bieger et al. |
| 6,772,001 B2 | 8/2004 | Maschke |
| 6,774,624 B2 | 8/2004 | Anderson et al. |
| 6,783,536 B2 | 8/2004 | Vilsmeier et al. |
| 6,784,660 B2 | 8/2004 | Ashe |
| 6,785,571 B2 | 8/2004 | Glossop |
| 6,786,219 B2 | 9/2004 | Garibaldi et al. |
| 6,786,870 B2 | 9/2004 | Miyaki et al. |
| 6,788,967 B2 | 9/2004 | Ben-Haim et al. |
| 6,794,667 B2 | 9/2004 | Noshi |
| 6,799,066 B2 | 9/2004 | Steines et al. |
| 6,815,651 B2 | 11/2004 | Odell |
| 6,816,266 B2 | 11/2004 | Varshneya et al. |
| 6,817,364 B2 | 11/2004 | Garibaldi et al. |
| 6,834,201 B2 | 12/2004 | Gillies et al. |
| 6,844,713 B2 | 1/2005 | Steber et al. |
| 6,845,142 B2 | 1/2005 | Ohishi |
| 6,850,788 B2 * | 2/2005 | Al-Ali .................. A61B 5/742 600/323 |
| 6,856,823 B2 | 2/2005 | Ashe |
| 6,857,196 B2 | 2/2005 | Dalrymple |
| 6,860,422 B2 | 3/2005 | Hull et al. |
| 6,862,467 B2 | 3/2005 | Moore et al. |
| 6,869,390 B2 | 3/2005 | Elliott et al. |
| 6,875,179 B2 | 4/2005 | Ferguson et al. |
| 6,879,160 B2 | 4/2005 | Jakab |
| 6,887,206 B2 | 5/2005 | Hoeksel et al. |
| 6,889,091 B2 | 5/2005 | Hine et al. |
| 6,895,268 B1 | 5/2005 | Rahn et al. |
| 6,902,528 B1 | 6/2005 | Garibaldi et al. |
| 6,905,469 B2 | 6/2005 | Hascoet et al. |
| 6,908,433 B1 | 6/2005 | Pruter |
| 6,911,026 B1 | 6/2005 | Hall et al. |
| 6,923,782 B2 | 8/2005 | O'Mahony et al. |
| 6,926,673 B2 | 8/2005 | Roberts et al. |
| 6,926,674 B2 | 8/2005 | Tenerz et al. |
| 6,934,575 B2 | 8/2005 | Ferre et al. |
| 6,936,010 B2 | 8/2005 | Fang et al. |
| 6,939,313 B2 | 9/2005 | Saadat et al. |
| 6,940,379 B2 | 9/2005 | Creighton |
| 6,941,166 B2 | 9/2005 | MacAdam et al. |
| 6,945,938 B2 | 9/2005 | Grunwald |
| 6,947,788 B2 | 9/2005 | Gilboa et al. |
| 6,950,689 B1 | 9/2005 | Willis et al. |
| 6,953,754 B2 | 10/2005 | Machida et al. |
| 6,958,677 B1 | 10/2005 | Carter |
| 6,959,214 B2 | 10/2005 | Pape et al. |
| 6,962,566 B2 | 11/2005 | Quistgaard et al. |
| 6,968,846 B2 | 11/2005 | Viswanathan |
| 6,975,197 B2 | 12/2005 | Creighton, IV |
| 6,976,962 B2 | 12/2005 | Bullis |
| 6,976,987 B2 | 12/2005 | Flores |
| 6,979,294 B1 | 12/2005 | Selzer et al. |
| 6,980,843 B2 | 12/2005 | Eng et al. |
| 6,980,852 B2 | 12/2005 | Jersey-Willuhn et al. |
| 6,980,921 B2 | 12/2005 | Anderson et al. |
| 6,986,739 B2 | 1/2006 | Warren et al. |
| 6,986,744 B1 | 1/2006 | Krivitski |
| 6,999,821 B2 | 2/2006 | Jenney et al. |
| 7,001,355 B2 | 2/2006 | Nunomura et al. |
| 7,008,418 B2 | 3/2006 | Hall et al. |
| 7,010,338 B2 | 3/2006 | Ritter et al. |
| 7,015,393 B2 | 3/2006 | Weiner et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| D518,574 S | 4/2006 | Chaggares |
| 7,022,075 B2 | 4/2006 | Grunwald et al. |
| 7,022,082 B2 | 4/2006 | Sonek |
| 7,026,927 B2 | 4/2006 | Wright et al. |
| 7,027,634 B2 | 4/2006 | Odell |
| 7,028,387 B1 | 4/2006 | Huynh et al. |
| 7,029,446 B2 | 4/2006 | Wendelken et al. |
| 7,033,603 B2 | 4/2006 | Nelson et al. |
| D520,139 S | 5/2006 | Chaggares |
| D520,140 S | 5/2006 | Chaggares |
| 7,038,398 B1 | 5/2006 | Lys et al. |
| 7,038,657 B2 | 5/2006 | Rosenberg et al. |
| 7,043,293 B1 | 5/2006 | Baura |
| 7,048,733 B2 | 5/2006 | Hartley et al. |
| 7,054,228 B1 | 5/2006 | Hickling |
| 7,065,403 B1 | 6/2006 | Mouchawar et al. |
| 7,066,914 B2 | 6/2006 | Andersen |
| 7,066,924 B1 | 6/2006 | Garibaldi et al. |
| 7,069,072 B2 | 6/2006 | Jansen et al. |
| D525,363 S | 7/2006 | Chaggares |
| 7,070,565 B2 | 7/2006 | Vaezy et al. |
| 7,072,704 B2 | 7/2006 | Bucholz |
| 7,082,325 B2 | 7/2006 | Hashimshony et al. |
| 7,090,639 B2 | 8/2006 | Govari |
| 7,096,059 B2 | 8/2006 | Geddes et al. |
| 7,096,148 B2 | 8/2006 | Anderson et al. |
| 7,096,870 B2 | 8/2006 | Lamprich et al. |
| 7,098,907 B2 | 8/2006 | Houston et al. |
| 7,103,205 B2 | 9/2006 | Wang et al. |
| 7,104,980 B1 | 9/2006 | Laherty et al. |
| 7,106,043 B1 | 9/2006 | Da Silva et al. |
| 7,106,431 B2 | 9/2006 | Odell |
| 7,106,479 B2 | 9/2006 | Roy et al. |
| 7,107,105 B2 | 9/2006 | Bjorklund et al. |
| 7,112,197 B2 | 9/2006 | Hartley et al. |
| 7,128,734 B1 | 10/2006 | Wilson et al. |
| 7,132,804 B2 | 11/2006 | Lys et al. |
| 7,137,976 B2 | 11/2006 | Ritter et al. |
| 7,141,019 B2 | 11/2006 | Pearlman |
| 7,141,812 B2 | 11/2006 | Appleby et al. |
| 7,142,905 B2 | 11/2006 | Slayton et al. |
| 7,148,970 B2 | 12/2006 | de Boer |
| 7,153,291 B2 | 12/2006 | Bierman |

(56) References Cited

U.S. PATENT DOCUMENTS

| | | |
|---|---|---|
| 7,161,453 B2 | 1/2007 | Creighton, IV |
| 7,162,291 B1 | 1/2007 | Nachaliel |
| 7,167,738 B2 | 1/2007 | Schweikard et al. |
| 7,169,107 B2 | 1/2007 | Jersey-Willuhn et al. |
| 7,169,109 B2 | 1/2007 | Jansen et al. |
| 7,174,201 B2 | 2/2007 | Govari et al. |
| 7,175,646 B2 | 2/2007 | Brenneman et al. |
| 7,180,252 B2 | 2/2007 | Lys et al. |
| 7,184,820 B2 | 2/2007 | Jersey-Willuhn et al. |
| 7,189,198 B2 | 3/2007 | Harburn et al. |
| 7,189,205 B2 | 3/2007 | McMorrow et al. |
| 7,189,208 B1 | 3/2007 | Beatty et al. |
| 7,190,819 B2 | 3/2007 | Viswanathan |
| 7,194,295 B2 | 3/2007 | Vilsmeier |
| 7,204,798 B2 | 4/2007 | Zdeblick et al. |
| 7,206,064 B2 | 4/2007 | Rogers et al. |
| 7,207,941 B2 | 4/2007 | Sharf |
| 7,211,082 B2 | 5/2007 | Hall et al. |
| 7,214,191 B2 | 5/2007 | Stringer et al. |
| 7,215,326 B2 | 5/2007 | Rosenberg |
| 7,221,104 B2 | 5/2007 | Lys et al. |
| 7,223,256 B2 | 5/2007 | Bierman |
| 7,229,400 B2 | 6/2007 | Elliott et al. |
| 7,231,243 B2 | 6/2007 | Tearney et al. |
| 7,236,157 B2 | 6/2007 | Schena et al. |
| 7,236,816 B2 | 6/2007 | Kumar et al. |
| 7,236,820 B2 | 6/2007 | Mabary et al. |
| 7,237,313 B2 | 7/2007 | Skujins et al. |
| 7,238,169 B2 | 7/2007 | Takagi et al. |
| 7,241,267 B2 | 7/2007 | Furia |
| 7,244,234 B2 | 7/2007 | Ridley et al. |
| 7,248,032 B1 | 7/2007 | Hular et al. |
| 7,248,914 B2 | 7/2007 | Hastings et al. |
| 7,252,633 B2 | 8/2007 | Obata et al. |
| 7,261,691 B1 | 8/2007 | Asomani |
| 7,264,584 B2 | 9/2007 | Ritter et al. |
| 7,270,662 B2 | 9/2007 | Visram et al. |
| 7,276,044 B2 | 10/2007 | Ferry et al. |
| 7,286,034 B2 | 10/2007 | Creighton |
| 7,291,146 B2 | 11/2007 | Steinke et al. |
| 7,297,140 B2 | 11/2007 | Orlu et al. |
| 7,299,085 B2 | 11/2007 | Bergelson et al. |
| 7,300,430 B2 | 11/2007 | Wilson et al. |
| 7,302,288 B1 | 11/2007 | Schellenberg |
| 7,308,296 B2 | 12/2007 | Lys et al. |
| 7,310,150 B2 | 12/2007 | Guillermo et al. |
| 7,311,702 B2 | 12/2007 | Tallarida et al. |
| 7,321,228 B2 | 1/2008 | Govari |
| 7,326,241 B2 | 2/2008 | Jang |
| 7,327,872 B2 | 2/2008 | Vaillant et al. |
| 7,331,462 B2 | 2/2008 | Steppe |
| 7,342,058 B2 | 3/2008 | Peppmoller et al. |
| 7,344,554 B2 | 3/2008 | Kuyava et al. |
| 7,349,732 B1 | 3/2008 | Kil et al. |
| 7,355,716 B2 | 4/2008 | de Boer et al. |
| 7,360,427 B2 | 4/2008 | Drinkwater et al. |
| 7,366,376 B2 | 4/2008 | Shishkov et al. |
| 7,366,562 B2 | 4/2008 | Dukesherer et al. |
| 7,366,563 B2 | 4/2008 | Kleen et al. |
| 7,373,271 B1 | 5/2008 | Schneider |
| 7,381,204 B2 | 6/2008 | Wilson et al. |
| 7,382,949 B2 | 6/2008 | Bouma et al. |
| 7,384,407 B2 | 6/2008 | Rodriguez et al. |
| 7,413,562 B2 | 8/2008 | Ferguson et al. |
| 7,418,169 B2 | 8/2008 | Tearney et al. |
| 7,447,408 B2 | 11/2008 | Bouma et al. |
| 7,452,331 B1 | 11/2008 | Pruter |
| 7,452,358 B2 | 11/2008 | Stern et al. |
| 7,454,244 B2 | 11/2008 | Kassab et al. |
| D585,556 S | 1/2009 | Kosaku |
| 7,479,141 B2 | 1/2009 | Kleen et al. |
| 7,507,114 B2 | 3/2009 | Kent et al. |
| 7,519,424 B2 | 4/2009 | Dennis et al. |
| 7,529,584 B2 | 5/2009 | Laske et al. |
| 7,534,223 B2 | 5/2009 | Boutilette et al. |
| 7,538,859 B2 | 5/2009 | Tearney et al. |
| 7,543,239 B2 | 6/2009 | Viswanathan et al. |
| 7,546,158 B2 | 6/2009 | Allison et al. |
| 7,547,282 B2 | 6/2009 | Lo et al. |
| 7,551,293 B2 | 6/2009 | Yelin et al. |
| D603,050 S | 10/2009 | Chen |
| 7,599,730 B2 | 10/2009 | Hunter et al. |
| 7,606,615 B2 | 10/2009 | Makower et al. |
| 7,613,478 B2 | 11/2009 | Jabri et al. |
| 7,616,992 B2 | 11/2009 | Dennis et al. |
| 7,627,376 B2 | 12/2009 | Dennis et al. |
| 7,635,336 B1 | 12/2009 | Pruter |
| 7,637,163 B2 | 12/2009 | Fetzer et al. |
| 7,640,053 B2 | 12/2009 | Verin |
| 7,651,469 B2 | 1/2010 | Osborne et al. |
| 7,652,080 B2 | 1/2010 | Peppmoller et al. |
| 7,660,623 B2 | 2/2010 | Hunter et al. |
| 7,665,893 B2 | 2/2010 | Buchalter |
| 7,666,191 B2 | 2/2010 | Orban, III et al. |
| 7,668,583 B2 | 2/2010 | Fegert et al. |
| 7,697,972 B2 | 4/2010 | Verard et al. |
| 7,699,782 B2 | 4/2010 | Angelsen et al. |
| 7,699,829 B2 | 4/2010 | Harris et al. |
| 7,715,925 B2 | 5/2010 | Hafer et al. |
| 7,727,153 B2 | 6/2010 | Fritz et al. |
| 7,727,192 B2 | 6/2010 | Tokumoto et al. |
| 7,729,743 B2 | 6/2010 | Sabczynski et al. |
| 7,751,865 B2 | 7/2010 | Jascob et al. |
| 7,766,839 B2 | 8/2010 | Rogers et al. |
| 7,771,437 B2 | 8/2010 | Hogg et al. |
| 7,774,051 B2 | 8/2010 | Voth |
| 7,774,055 B1 | 8/2010 | Min |
| 7,794,407 B2 | 9/2010 | Rothenberg |
| 7,798,970 B2 | 9/2010 | Lo et al. |
| 7,819,810 B2 | 10/2010 | Stringer et al. |
| 7,822,464 B2 | 10/2010 | Maschke et al. |
| 7,828,528 B2 | 11/2010 | Estes et al. |
| 7,831,294 B2 | 11/2010 | Viswanathan |
| 7,831,449 B2 | 11/2010 | Ying et al. |
| 7,833,168 B2 | 11/2010 | Taylor et al. |
| 7,833,214 B2 | 11/2010 | Wilson et al. |
| 7,840,252 B2 | 11/2010 | Strommer et al. |
| D629,526 S | 12/2010 | Ladwig et al. |
| D629,527 S | 12/2010 | Crunkilton |
| 7,846,157 B2 | 12/2010 | Kozel |
| 7,850,613 B2 | 12/2010 | Stribling |
| D630,756 S | 1/2011 | Kitayama |
| D630,757 S | 1/2011 | Kitayama |
| 7,869,854 B2 | 1/2011 | Shachar et al. |
| 7,869,865 B2 | 1/2011 | Govari et al. |
| 7,873,402 B2 | 1/2011 | Shachar |
| 7,887,516 B2 | 2/2011 | Young |
| 7,909,815 B2 | 3/2011 | Whitmore, III et al. |
| 7,931,596 B2 | 4/2011 | Rachlin et al. |
| 7,947,040 B2 | 5/2011 | Davies et al. |
| 7,969,142 B2 | 6/2011 | Krueger et al. |
| 7,976,469 B2 | 7/2011 | Bonde et al. |
| 7,976,518 B2 | 7/2011 | Shaughnessy et al. |
| 7,981,038 B2 | 7/2011 | Kanade et al. |
| 7,988,633 B2 | 8/2011 | Hossack et al. |
| 8,016,814 B2 | 9/2011 | Blakstvedt et al. |
| 8,046,052 B2 | 10/2011 | Verard et al. |
| 8,055,327 B2 | 11/2011 | Strommer et al. |
| 8,057,394 B2 | 11/2011 | Dala-Krishna |
| 8,060,185 B2 | 11/2011 | Hunter et al. |
| 8,078,274 B2 | 12/2011 | Kassab |
| 8,078,279 B2 | 12/2011 | Dennis et al. |
| 8,082,025 B2 | 12/2011 | Amitai et al. |
| 8,082,032 B2 | 12/2011 | Kassab et al. |
| 8,088,072 B2 | 1/2012 | Munrow et al. |
| 8,090,427 B2 | 1/2012 | Eck et al. |
| 8,090,430 B2 | 1/2012 | Makower et al. |
| 8,099,161 B2 | 1/2012 | Kassab |
| 8,105,338 B2 | 1/2012 | Anderson et al. |
| 8,114,143 B2 | 2/2012 | Kassab et al. |
| 8,118,743 B2 | 2/2012 | Park et al. |
| 8,123,691 B2 | 2/2012 | Mine et al. |
| 8,133,698 B2 | 3/2012 | Silver |
| 8,142,417 B2 | 3/2012 | Pajunk et al. |

(56) References Cited

U.S. PATENT DOCUMENTS

| | | |
|---|---|---|
| 8,150,522 B2 | 4/2012 | Echauz et al. |
| 8,152,724 B2 | 4/2012 | Ridley et al. |
| 8,155,732 B2 | 4/2012 | Scholz et al. |
| 8,204,582 B2 | 6/2012 | Zantos et al. |
| 8,214,018 B2 | 7/2012 | Markowitz et al. |
| 8,221,402 B2 | 7/2012 | Francischelli et al. |
| 8,226,540 B1 | 7/2012 | Chi |
| 8,228,347 B2 | 7/2012 | Beasley et al. |
| 8,240,211 B2 | 8/2012 | Zeitner et al. |
| 8,241,274 B2 | 8/2012 | Keogh et al. |
| 8,244,339 B2 | 8/2012 | Shen et al. |
| 8,255,035 B2 | 8/2012 | Cao et al. |
| 8,260,395 B2 | 9/2012 | Markowitz et al. |
| 8,262,577 B2 | 9/2012 | Munrow et al. |
| 8,298,147 B2 | 10/2012 | Huennekens et al. |
| 8,298,149 B2 | 10/2012 | Hastings et al. |
| 8,303,502 B2 | 11/2012 | Washburn et al. |
| 8,303,505 B2 | 11/2012 | Webler et al. |
| 8,326,419 B2 | 12/2012 | Rosenberg et al. |
| 8,326,651 B2 | 12/2012 | McLaren et al. |
| 8,340,751 B2 | 12/2012 | Markowitz et al. |
| 8,346,343 B2 | 1/2013 | Kimura et al. |
| 8,369,922 B2 | 2/2013 | Paul et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,400,164 B2 | 3/2013 | Osadchy et al. |
| 8,401,616 B2 | 3/2013 | Verard et al. |
| 8,409,103 B2 | 4/2013 | Grunwald et al. |
| 8,412,313 B2 | 4/2013 | Amitai et al. |
| 8,425,425 B2 | 4/2013 | Hagy et al. |
| 8,437,833 B2 | 5/2013 | Silverstein |
| 8,439,873 B1 | 5/2013 | Donovan |
| 8,442,621 B2 | 5/2013 | Gorek et al. |
| 8,447,384 B2 | 5/2013 | Xu et al. |
| D684,265 S | 6/2013 | Cadera |
| 8,456,182 B2 | 6/2013 | Bar-Tal et al. |
| 8,478,382 B2 | 7/2013 | Burnside et al. |
| 8,478,388 B2 | 7/2013 | Nguyen et al. |
| 8,485,980 B2 | 7/2013 | Sinderby et al. |
| 8,494,608 B2 | 7/2013 | Markowitz et al. |
| 8,496,592 B2 | 7/2013 | Ridley et al. |
| 8,504,139 B2 | 8/2013 | Jacobsen et al. |
| 8,512,256 B2 | 8/2013 | Rothenberg |
| 8,521,122 B2 | 8/2013 | Scott et al. |
| 8,527,036 B2 | 9/2013 | Jalde et al. |
| 8,529,433 B2 | 9/2013 | Kawano et al. |
| 8,538,509 B2 | 9/2013 | Harlev et al. |
| 8,545,255 B2 | 10/2013 | Litzler et al. |
| 8,597,193 B2 | 12/2013 | Grunwald et al. |
| 8,620,412 B2 | 12/2013 | Griffiths et al. |
| 8,644,907 B2 | 2/2014 | Hartmann et al. |
| 8,663,116 B2 | 3/2014 | Hamilton, Jr. |
| 8,676,295 B2 | 3/2014 | Cunningham et al. |
| 8,690,776 B2 | 4/2014 | Razzaque et al. |
| 8,700,137 B2 | 4/2014 | Albert |
| 8,715,195 B2 | 5/2014 | Ziv |
| 8,721,655 B2 | 5/2014 | Viswanathan et al. |
| 8,734,440 B2 | 5/2014 | Wu |
| 8,761,862 B2 | 6/2014 | Ridley et al. |
| 8,774,907 B2 | 7/2014 | Rothenberg |
| 8,781,555 B2 | 7/2014 | Burnside et al. |
| 8,784,336 B2 | 7/2014 | Bown et al. |
| 8,801,693 B2 | 8/2014 | He et al. |
| 8,849,382 B2 | 9/2014 | Cox et al. |
| 8,858,455 B2 | 10/2014 | Rothenberg |
| 8,934,961 B2 | 1/2015 | Lakin et al. |
| 8,942,784 B2 | 1/2015 | Neidert et al. |
| 8,965,490 B2 | 2/2015 | Lee et al. |
| 8,971,994 B2 | 3/2015 | Burnside et al. |
| 9,014,794 B2 | 4/2015 | Brodnick et al. |
| 9,033,889 B2 | 5/2015 | Hamilton, Jr. |
| 9,125,578 B2 | 9/2015 | Grunwald |
| 9,179,860 B2 | 11/2015 | Markowitz et al. |
| 9,198,600 B2 | 12/2015 | Grunwald et al. |
| 9,339,206 B2 | 5/2016 | Grunwald |
| 9,415,188 B2 | 8/2016 | He et al. |
| 9,456,766 B2 | 10/2016 | Cox et al. |
| 9,492,097 B2 | 11/2016 | Wilkes et al. |
| 9,521,961 B2 | 12/2016 | Silverstein et al. |
| 9,526,440 B2 | 12/2016 | Burnside et al. |
| 9,532,724 B2 | 1/2017 | Grunwald |
| 9,554,716 B2 | 1/2017 | Burnside et al. |
| 9,636,031 B2 | 5/2017 | Cox |
| 9,642,986 B2 | 5/2017 | Beasley |
| 9,649,048 B2 | 5/2017 | Cox et al. |
| 9,681,823 B2 | 6/2017 | Messerly et al. |
| 9,833,169 B2 | 12/2017 | Rothenberg |
| 9,839,372 B2 | 12/2017 | Bukhman et al. |
| 9,901,714 B2 | 2/2018 | Lemon et al. |
| 9,907,513 B2 | 3/2018 | Silverstein |
| 9,949,720 B2 | 4/2018 | Southard et al. |
| 9,999,371 B2 | 6/2018 | Messerly et al. |
| 10,004,875 B2 | 6/2018 | Bown et al. |
| 10,046,139 B2 | 8/2018 | Powers et al. |
| 10,105,121 B2 | 10/2018 | Burnside et al. |
| 10,165,962 B2 | 1/2019 | Messerly et al. |
| 10,231,643 B2 | 3/2019 | Grunwald |
| 10,231,753 B2 | 3/2019 | Burnside et al. |
| 10,238,418 B2 | 3/2019 | Cox et al. |
| 10,271,762 B2 | 4/2019 | Grunwald |
| 10,349,857 B2 | 7/2019 | Grunwald |
| 10,349,890 B2 | 7/2019 | Misener et al. |
| 10,449,330 B2 | 10/2019 | Newman et al. |
| 10,524,691 B2 | 1/2020 | Newman et al. |
| 10,524,694 B2 | 1/2020 | Hunter |
| 10,602,958 B2 | 3/2020 | Silverstein et al. |
| 10,751,509 B2 | 8/2020 | Misener |
| 10,849,695 B2 | 12/2020 | Cox et al. |
| 2001/0014774 A1 | 8/2001 | Grunwald |
| 2001/0027332 A1 | 10/2001 | Grunwald et al. |
| 2002/0010392 A1 | 1/2002 | Desai |
| 2002/0016549 A1 | 2/2002 | Mejia |
| 2002/0019447 A1 | 2/2002 | Renn et al. |
| 2002/0022777 A1 | 2/2002 | Crieghton et al. |
| 2002/0032391 A1 | 3/2002 | McFann et al. |
| 2002/0045810 A1 | 4/2002 | Ben-Haim |
| 2002/0049488 A1 | 4/2002 | Boneau |
| 2002/0055680 A1 | 5/2002 | Miele et al. |
| 2002/0082559 A1 | 6/2002 | Chang et al. |
| 2002/0113555 A1 | 8/2002 | Lys et al. |
| 2002/0123679 A1 | 9/2002 | Dominguez |
| 2002/0128554 A1 | 9/2002 | Seward |
| 2002/0129952 A1 | 9/2002 | Matsudate et al. |
| 2002/0133079 A1 | 9/2002 | Sandhu |
| 2002/0156363 A1 | 10/2002 | Hunter et al. |
| 2002/0156376 A1 | 10/2002 | Wang et al. |
| 2002/0165448 A1 | 11/2002 | Ben-Haim et al. |
| 2002/0165534 A1 | 11/2002 | Hayzelden et al. |
| 2002/0165537 A1 | 11/2002 | Kelley et al. |
| 2002/0173721 A1 | 11/2002 | Grunwald et al. |
| 2002/0193756 A1 | 12/2002 | Prindle |
| 2002/0198568 A1 | 12/2002 | Hafer et al. |
| 2003/0009132 A1 | 1/2003 | Schwartz et al. |
| 2003/0011359 A1 | 1/2003 | Ashe |
| 2003/0013959 A1 | 1/2003 | Grunwald et al. |
| 2003/0013966 A1 | 1/2003 | Barnes et al. |
| 2003/0013986 A1 | 1/2003 | Saadat |
| 2003/0018251 A1 | 1/2003 | Solomon |
| 2003/0036696 A1 | 2/2003 | Willis et al. |
| 2003/0040671 A1 | 2/2003 | Somogyi et al. |
| 2003/0040743 A1 | 2/2003 | Cosman et al. |
| 2003/0047126 A1 | 3/2003 | Tomaschko |
| 2003/0072805 A1 | 4/2003 | Miyazawa et al. |
| 2003/0073901 A1 | 4/2003 | Simon et al. |
| 2003/0076281 A1 | 4/2003 | Morgan et al. |
| 2003/0083698 A1 | 5/2003 | Whitehurst et al. |
| 2003/0088195 A1 | 5/2003 | Vardi et al. |
| 2003/0092993 A1 | 5/2003 | Grunwald |
| 2003/0100849 A1 | 5/2003 | Jang |
| 2003/0114742 A1 | 6/2003 | Lewkowicz et al. |
| 2003/0114777 A1 | 6/2003 | Griffin et al. |
| 2003/0120150 A1 | 6/2003 | Govari |
| 2003/0120154 A1 | 6/2003 | Sauer et al. |

(56) References Cited

U.S. PATENT DOCUMENTS

| | | |
|---|---|---|
| 2003/0139661 A1 | 7/2003 | Kimchy et al. |
| 2003/0149328 A1 | 8/2003 | Elliott et al. |
| 2003/0149368 A1 | 8/2003 | Hennemann et al. |
| 2003/0152290 A1 | 8/2003 | Odell |
| 2003/0160721 A1 | 8/2003 | Gilboa et al. |
| 2003/0162414 A1 | 8/2003 | Schulz et al. |
| 2003/0163037 A1 | 8/2003 | Bladen et al. |
| 2003/0163142 A1 | 8/2003 | Paltieli et al. |
| 2003/0171691 A1 | 9/2003 | Casscells et al. |
| 2003/0173953 A1 | 9/2003 | Ashe |
| 2003/0181892 A1 | 9/2003 | Pajunk et al. |
| 2003/0184544 A1 | 10/2003 | Prudent |
| 2003/0191392 A1 | 10/2003 | Haldeman |
| 2003/0191460 A1 | 10/2003 | Hobbs et al. |
| 2003/0195420 A1 | 10/2003 | Mendlein et al. |
| 2003/0199746 A1 | 10/2003 | Fuimaono et al. |
| 2003/0208142 A1 | 11/2003 | Boudewijn et al. |
| 2003/0216639 A1 | 11/2003 | Gilboa et al. |
| 2003/0216723 A1 | 11/2003 | Shinmura et al. |
| 2003/0220557 A1 | 11/2003 | Cleary et al. |
| 2003/0220578 A1 | 11/2003 | Ho et al. |
| 2003/0229298 A1 | 12/2003 | Iwami et al. |
| 2003/0233042 A1 | 12/2003 | Ashe |
| 2003/0236445 A1 | 12/2003 | Couvillon |
| 2004/0010189 A1 | 1/2004 | van Sloun et al. |
| 2004/0015070 A1 | 1/2004 | Liang et al. |
| 2004/0024301 A1 | 2/2004 | Hockett et al. |
| 2004/0030319 A1 | 2/2004 | Korkor et al. |
| 2004/0054278 A1 | 3/2004 | Kimchy et al. |
| 2004/0059217 A1 | 3/2004 | Kessman et al. |
| 2004/0059237 A1 | 3/2004 | Narayan et al. |
| 2004/0082916 A1 | 4/2004 | Jenkins |
| 2004/0087877 A1 | 5/2004 | Besz et al. |
| 2004/0088136 A1 | 5/2004 | Ashe |
| 2004/0092962 A1 | 5/2004 | Thornton et al. |
| 2004/0097803 A1 | 5/2004 | Panescu |
| 2004/0097804 A1 | 5/2004 | Sobe |
| 2004/0097805 A1 | 5/2004 | Verard et al. |
| 2004/0097806 A1 | 5/2004 | Hunter et al. |
| 2004/0116809 A1 | 6/2004 | Chow et al. |
| 2004/0127805 A1 | 7/2004 | MacAdam et al. |
| 2004/0131998 A1 | 7/2004 | Marom et al. |
| 2004/0133111 A1 | 7/2004 | Szczech et al. |
| 2004/0133130 A1 | 7/2004 | Ferry et al. |
| 2004/0135069 A1 | 7/2004 | Odell |
| 2004/0138557 A1 | 7/2004 | Le et al. |
| 2004/0138564 A1 | 7/2004 | Hwang et al. |
| 2004/0138569 A1 | 7/2004 | Grunwald et al. |
| 2004/0138570 A1 | 7/2004 | Nita et al. |
| 2004/0143183 A1 | 7/2004 | Toyoda et al. |
| 2004/0147837 A1 | 7/2004 | Macaulay et al. |
| 2004/0150963 A1 | 8/2004 | Holmberg et al. |
| 2004/0152972 A1 | 8/2004 | Hunter |
| 2004/0155609 A1 | 8/2004 | Lys et al. |
| 2004/0158140 A1 | 8/2004 | Fuimaono et al. |
| 2004/0162487 A1 | 8/2004 | Klingenbeck-Regn et al. |
| 2004/0171924 A1 | 9/2004 | Mire et al. |
| 2004/0176688 A1 | 9/2004 | Haldeman |
| 2004/0186461 A1 | 9/2004 | DiMatteo |
| 2004/0199069 A1 | 10/2004 | Connelly et al. |
| 2004/0210289 A1 | 10/2004 | Wang et al. |
| 2004/0225233 A1 | 11/2004 | Frankowski et al. |
| 2004/0230131 A1 | 11/2004 | Kassab et al. |
| 2004/0230271 A1 | 11/2004 | Wang et al. |
| 2004/0234453 A1 | 11/2004 | Smith |
| 2004/0243018 A1 | 12/2004 | Organ et al. |
| 2004/0243116 A1 | 12/2004 | Joye et al. |
| 2004/0243118 A1 | 12/2004 | Ayers et al. |
| 2004/0253365 A1 | 12/2004 | Warren et al. |
| 2004/0254470 A1 | 12/2004 | Drinkwater et al. |
| 2004/0254495 A1 | 12/2004 | Mabary et al. |
| 2004/0260174 A1 | 12/2004 | Keene |
| 2004/0267086 A1 | 12/2004 | Anstadt et al. |
| 2005/0004450 A1 | 1/2005 | Ben-Haim et al. |
| 2005/0021019 A1 | 1/2005 | Hashimshony et al. |
| 2005/0033150 A1 | 2/2005 | Takahashi et al. |
| 2005/0038355 A1 | 2/2005 | Gellman et al. |
| 2005/0043640 A1 | 2/2005 | Chang |
| 2005/0049486 A1 | 3/2005 | Urquhart et al. |
| 2005/0049510 A1 | 3/2005 | Haldeman et al. |
| 2005/0063194 A1 | 3/2005 | Lys et al. |
| 2005/0070788 A1 | 3/2005 | Wilson et al. |
| 2005/0075561 A1 | 4/2005 | Golden |
| 2005/0085715 A1 | 4/2005 | Dukesherer et al. |
| 2005/0085716 A1 | 4/2005 | Hamm et al. |
| 2005/0085718 A1 | 4/2005 | Shahidi |
| 2005/0085720 A1 | 4/2005 | Jascob et al. |
| 2005/0090746 A1 | 4/2005 | Ohtake |
| 2005/0101868 A1 | 5/2005 | Ridley et al. |
| 2005/0101869 A1 | 5/2005 | Burba et al. |
| 2005/0105081 A1 | 5/2005 | Odell |
| 2005/0105101 A1 | 5/2005 | Duling et al. |
| 2005/0112135 A1 | 5/2005 | Cormier et al. |
| 2005/0113669 A1 | 5/2005 | Helfer et al. |
| 2005/0113676 A1 | 5/2005 | Weiner et al. |
| 2005/0113700 A1 | 5/2005 | Yanagihara et al. |
| 2005/0113873 A1 | 5/2005 | Weiner et al. |
| 2005/0113874 A1 | 5/2005 | Connelly et al. |
| 2005/0113876 A1 | 5/2005 | Weiner et al. |
| 2005/0143689 A1 | 6/2005 | Ramsey |
| 2005/0148836 A1 | 7/2005 | Kleen et al. |
| 2005/0148902 A1 | 7/2005 | Minar et al. |
| 2005/0149002 A1 | 7/2005 | Wang et al. |
| 2005/0151489 A1 | 7/2005 | Lys et al. |
| 2005/0154308 A1 | 7/2005 | Quistgaard et al. |
| 2005/0159644 A1 | 7/2005 | Takano |
| 2005/0159790 A1 | 7/2005 | Shalev |
| 2005/0165301 A1 | 7/2005 | Smith et al. |
| 2005/0165313 A1 | 7/2005 | Byron et al. |
| 2005/0175665 A1 | 8/2005 | Hunter et al. |
| 2005/0175703 A1 | 8/2005 | Hunter et al. |
| 2005/0178395 A1 | 8/2005 | Hunter et al. |
| 2005/0178396 A1 | 8/2005 | Hunter et al. |
| 2005/0182295 A1 | 8/2005 | Soper et al. |
| 2005/0182454 A1 | 8/2005 | Gharib et al. |
| 2005/0197674 A1 | 9/2005 | McCabe et al. |
| 2005/0203368 A1 | 9/2005 | Verin |
| 2005/0203396 A1 | 9/2005 | Angelsen et al. |
| 2005/0205081 A1 | 9/2005 | Barker et al. |
| 2005/0215901 A1 | 9/2005 | Anderson et al. |
| 2005/0215945 A1 | 9/2005 | Harris et al. |
| 2005/0222532 A1 | 10/2005 | Bertolero et al. |
| 2005/0240102 A1 | 10/2005 | Rachlin et al. |
| 2005/0245811 A1 | 11/2005 | Scheffler |
| 2005/0256398 A1 | 11/2005 | Hastings et al. |
| 2005/0256451 A1 | 11/2005 | Adams et al. |
| 2005/0256521 A1 | 11/2005 | Kozel |
| 2005/0256541 A1 | 11/2005 | Stypulkowski |
| 2005/0283210 A1 | 12/2005 | Blischak et al. |
| 2005/0283216 A1 | 12/2005 | Pyles |
| 2005/0288586 A1 | 12/2005 | Ferek-Petric |
| 2005/0288695 A1 | 12/2005 | Jenson et al. |
| 2006/0009759 A1 | 1/2006 | Chrisitian et al. |
| 2006/0015003 A1 | 1/2006 | Moaddes et al. |
| 2006/0015039 A1 | 1/2006 | Cassidy et al. |
| 2006/0025677 A1 | 2/2006 | Verard et al. |
| 2006/0025697 A1 | 2/2006 | Kurzweil et al. |
| 2006/0058633 A1 | 3/2006 | Hoshino et al. |
| 2006/0065275 A1 | 3/2006 | Lamprich et al. |
| 2006/0068074 A1 | 3/2006 | Stefandl |
| 2006/0084867 A1 | 4/2006 | Tremblay et al. |
| 2006/0106306 A1 | 5/2006 | Essner et al. |
| 2006/0116571 A1 | 6/2006 | Maschke et al. |
| 2006/0116576 A1 | 6/2006 | McGee et al. |
| 2006/0116578 A1 | 6/2006 | Grunwald et al. |
| 2006/0122514 A1 | 6/2006 | Byrd et al. |
| 2006/0142656 A1 | 6/2006 | Malackowski et al. |
| 2006/0149134 A1 | 7/2006 | Soper et al. |
| 2006/0173251 A1 | 8/2006 | Govari et al. |
| 2006/0173329 A1 | 8/2006 | Irioka et al. |
| 2006/0173407 A1 | 8/2006 | Shaughnessy et al. |
| 2006/0176242 A1 | 8/2006 | Jaramaz et al. |
| 2006/0184029 A1 | 8/2006 | Haim et al. |
| 2006/0184074 A1 | 8/2006 | Vaezy et al. |

(56) References Cited

U.S. PATENT DOCUMENTS

| | | |
|---|---|---|
| 2006/0206037 A1 | 9/2006 | Braxton |
| 2006/0211944 A1 | 9/2006 | Mauge et al. |
| 2006/0217655 A1 | 9/2006 | Vitullo et al. |
| 2006/0217755 A1 | 9/2006 | Eversull et al. |
| 2006/0224188 A1 | 10/2006 | Libbus et al. |
| 2006/0241432 A1 | 10/2006 | Herline et al. |
| 2006/0247746 A1 | 11/2006 | Danek et al. |
| 2006/0253029 A1 | 11/2006 | Altmann et al. |
| 2006/0253115 A1 | 11/2006 | Avitall et al. |
| 2006/0258895 A1 | 11/2006 | Maschke |
| 2006/0276867 A1 | 12/2006 | Viswanathan |
| 2006/0287595 A1 | 12/2006 | Maschke |
| 2007/0010753 A1 | 1/2007 | MacAdam |
| 2007/0015960 A1 | 1/2007 | Gomert et al. |
| 2007/0016007 A1 | 1/2007 | Govari et al. |
| 2007/0016013 A1 | 1/2007 | Camus |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0032746 A1 | 2/2007 | Sell |
| 2007/0038113 A1 | 2/2007 | Oonuki et al. |
| 2007/0049817 A1 | 3/2007 | Preiss et al. |
| 2007/0049822 A1 | 3/2007 | Bunce et al. |
| 2007/0049846 A1 | 3/2007 | Bown et al. |
| 2007/0055141 A1 | 3/2007 | Kruger et al. |
| 2007/0055142 A1 | 3/2007 | Webler |
| 2007/0055294 A1 | 3/2007 | Giap |
| 2007/0060992 A1 | 3/2007 | Pappone |
| 2007/0062544 A1 | 3/2007 | Rauk Bergstrom et al. |
| 2007/0066888 A1 | 3/2007 | Maschke |
| 2007/0073155 A1 | 3/2007 | Park et al. |
| 2007/0078343 A1 | 4/2007 | Kawashima et al. |
| 2007/0087038 A1 | 4/2007 | Richardson et al. |
| 2007/0093710 A1 | 4/2007 | Maschke |
| 2007/0100236 A1 | 5/2007 | McMorrow et al. |
| 2007/0100285 A1 | 5/2007 | Griffin et al. |
| 2007/0112282 A1 | 5/2007 | Skujins et al. |
| 2007/0123805 A1 | 5/2007 | Shireman et al. |
| 2007/0129770 A1 | 6/2007 | Younis |
| 2007/0135803 A1 | 6/2007 | Belson |
| 2007/0135886 A1 | 6/2007 | Maschke |
| 2007/0156205 A1 | 7/2007 | Larson et al. |
| 2007/0161853 A1 | 7/2007 | Yagi et al. |
| 2007/0161914 A1 | 7/2007 | Zdeblick et al. |
| 2007/0161915 A1 | 7/2007 | Desai |
| 2007/0167738 A1 | 7/2007 | Timinger et al. |
| 2007/0167743 A1 | 7/2007 | Honda et al. |
| 2007/0167762 A1 | 7/2007 | Kim et al. |
| 2007/0167769 A1 | 7/2007 | Ikuma et al. |
| 2007/0167801 A1 | 7/2007 | Webler et al. |
| 2007/0167997 A1 | 7/2007 | Forsberg et al. |
| 2007/0197891 A1 | 8/2007 | Shachar et al. |
| 2007/0197905 A1 | 8/2007 | Timinger et al. |
| 2007/0197926 A1 | 8/2007 | Danehorn et al. |
| 2007/0199848 A1 | 8/2007 | Ellswood et al. |
| 2007/0208255 A1 | 9/2007 | Ridley et al. |
| 2007/0219453 A1 | 9/2007 | Kremliovsky et al. |
| 2007/0225589 A1 | 9/2007 | Viswanathan |
| 2007/0225610 A1 | 9/2007 | Mickley et al. |
| 2007/0232882 A1 | 10/2007 | Glossop et al. |
| 2007/0232896 A1 | 10/2007 | Gilboa et al. |
| 2007/0238984 A1 | 10/2007 | Maschke et al. |
| 2007/0239004 A1 | 10/2007 | Kakee et al. |
| 2007/0239018 A1 | 10/2007 | Fetzer et al. |
| 2007/0244413 A1 | 10/2007 | Biggins |
| 2007/0247454 A1 | 10/2007 | Rahn et al. |
| 2007/0249911 A1 | 10/2007 | Simon |
| 2007/0250150 A1 | 10/2007 | Pal et al. |
| 2007/0255270 A1 | 11/2007 | Carney |
| 2007/0265526 A1 | 11/2007 | Govari et al. |
| 2007/0280974 A1 | 12/2007 | Son et al. |
| 2007/0282196 A1 | 12/2007 | Birk et al. |
| 2007/0282197 A1 | 12/2007 | Bill et al. |
| 2007/0299352 A1 | 12/2007 | Harlev et al. |
| 2007/0299353 A1 | 12/2007 | Harlev et al. |
| 2008/0004652 A1 | 1/2008 | Abboud et al. |
| 2008/0008745 A1 | 1/2008 | Stinchcomb et al. |
| 2008/0009720 A1 | 1/2008 | Schefelker et al. |
| 2008/0015442 A1 | 1/2008 | Watson et al. |
| 2008/0021283 A1 | 1/2008 | Kuranda |
| 2008/0027320 A1 | 1/2008 | Bolorforosh et al. |
| 2008/0033282 A1 | 2/2008 | Bar-Tal et al. |
| 2008/0033283 A1 | 2/2008 | Dellaca et al. |
| 2008/0033316 A1 | 2/2008 | Kassab et al. |
| 2008/0033350 A1 | 2/2008 | Wilson et al. |
| 2008/0033759 A1 | 2/2008 | Finlay |
| 2008/0045908 A1 | 2/2008 | Gould et al. |
| 2008/0051626 A1 | 2/2008 | Sato et al. |
| 2008/0077158 A1 | 3/2008 | Haider et al. |
| 2008/0081958 A1 | 4/2008 | Denison et al. |
| 2008/0082136 A1 | 4/2008 | Gaudiani |
| 2008/0097232 A1 | 4/2008 | Rothenberg |
| 2008/0108949 A1 | 5/2008 | Beasley et al. |
| 2008/0114095 A1 | 5/2008 | Peppmoller et al. |
| 2008/0119697 A1 | 5/2008 | Vadodaria et al. |
| 2008/0125772 A1 | 5/2008 | Stone et al. |
| 2008/0137927 A1 | 6/2008 | Altmann et al. |
| 2008/0139944 A1 | 6/2008 | Weymer et al. |
| 2008/0146939 A1 | 6/2008 | McMorrow et al. |
| 2008/0146940 A1 | 6/2008 | Jenkins et al. |
| 2008/0146941 A1 | 6/2008 | Dala-Krishna |
| 2008/0146942 A1 | 6/2008 | Dala-Krishna |
| 2008/0154100 A1 | 6/2008 | Thalmeier et al. |
| 2008/0166453 A1 | 7/2008 | Steele et al. |
| 2008/0171934 A1 | 7/2008 | Greenan et al. |
| 2008/0183075 A1 | 7/2008 | Govari et al. |
| 2008/0188830 A1 | 8/2008 | Rosenblatt et al. |
| 2008/0190438 A1 | 8/2008 | Harlev et al. |
| 2008/0195169 A1 | 8/2008 | Pinter et al. |
| 2008/0200754 A1 | 8/2008 | Buchalter |
| 2008/0200801 A1 | 8/2008 | Wildes et al. |
| 2008/0200913 A1 | 8/2008 | Viswanathan |
| 2008/0228082 A1 | 9/2008 | Scheirer et al. |
| 2008/0236598 A1 | 10/2008 | Gobel |
| 2008/0255404 A1 | 10/2008 | Nogawa et al. |
| 2008/0255475 A1 | 10/2008 | Kondrosky et al. |
| 2008/0269581 A1 | 10/2008 | Wood et al. |
| 2008/0269611 A1 | 10/2008 | Pedrizzetti et al. |
| 2008/0275465 A1 | 11/2008 | Paul et al. |
| 2008/0275765 A1 | 11/2008 | Kuchar |
| 2008/0288038 A1 | 11/2008 | Paul et al. |
| 2008/0294041 A1 | 11/2008 | Kassab |
| 2008/0319350 A1 | 12/2008 | Wallace et al. |
| 2009/0005674 A1 | 1/2009 | Saadat et al. |
| 2009/0005675 A1 | 1/2009 | Grunwald et al. |
| 2009/0005679 A1 | 1/2009 | Dala-Krishna |
| 2009/0018497 A1 | 1/2009 | Birchard et al. |
| 2009/0024018 A1 | 1/2009 | Boyden et al. |
| 2009/0030380 A1 | 1/2009 | Binmoeller |
| 2009/0043205 A1 | 2/2009 | Pelissier et al. |
| 2009/0062646 A1 | 3/2009 | Creighton, IV et al. |
| 2009/0062684 A1 | 3/2009 | Gregersen et al. |
| 2009/0062772 A1 | 3/2009 | Wakeford et al. |
| 2009/0080738 A1 | 3/2009 | Zur et al. |
| 2009/0082661 A1 | 3/2009 | Saladin et al. |
| 2009/0084382 A1 | 4/2009 | Jalde et al. |
| 2009/0099468 A1 | 4/2009 | Thiagalingam et al. |
| 2009/0101577 A1 | 4/2009 | Fulkerson et al. |
| 2009/0115406 A1 | 5/2009 | Anderson et al. |
| 2009/0118612 A1 | 5/2009 | Grunwald et al. |
| 2009/0118637 A1 | 5/2009 | Kassab et al. |
| 2009/0118706 A1 | 5/2009 | Schweikert et al. |
| 2009/0124901 A1 | 5/2009 | Fink et al. |
| 2009/0143672 A1 | 6/2009 | Harms et al. |
| 2009/0143736 A1 | 6/2009 | Mittermeyer et al. |
| 2009/0156926 A1* | 6/2009 | Messerly ............... A61B 46/00 600/409 |
| 2009/0163810 A1 | 6/2009 | Kanade et al. |
| 2009/0171217 A1 | 7/2009 | Kim et al. |
| 2009/0177083 A1 | 7/2009 | Matsumura |
| 2009/0177090 A1 | 7/2009 | Grunwald et al. |
| 2009/0182224 A1 | 7/2009 | Shmarak et al. |
| 2009/0203989 A1 | 8/2009 | Burnside et al. |

(56) References Cited

U.S. PATENT DOCUMENTS

| | | |
|---|---|---|
| 2009/0204113 A1 | 8/2009 | MacAdam et al. |
| 2009/0209872 A1 | 8/2009 | Pop |
| 2009/0209950 A1 | 8/2009 | Starksen |
| 2009/0221908 A1 | 9/2009 | Glossop |
| 2009/0227952 A1 | 9/2009 | Blakstvedt et al. |
| 2009/0234328 A1 | 9/2009 | Cox et al. |
| 2009/0247835 A1* | 10/2009 | Voipio .............. A61B 5/04004 600/301 |
| 2009/0253976 A1 | 10/2009 | Harlev et al. |
| 2009/0258171 A1 | 10/2009 | Uang |
| 2009/0259124 A1 | 10/2009 | Rothenberg |
| 2009/0262982 A1 | 10/2009 | Markowitz et al. |
| 2009/0270729 A1 | 10/2009 | Corbucci et al. |
| 2009/0270746 A1 | 10/2009 | Min |
| 2009/0275828 A1 | 11/2009 | Shachar et al. |
| 2009/0281419 A1 | 11/2009 | Troesken et al. |
| 2009/0297441 A1 | 12/2009 | Canham et al. |
| 2009/0312629 A1 | 12/2009 | Razzaque et al. |
| 2010/0004543 A1 | 1/2010 | Ahlund et al. |
| 2010/0004547 A1 | 1/2010 | Scholz et al. |
| 2010/0010355 A1 | 1/2010 | Kassab |
| 2010/0010444 A1 | 1/2010 | Bettuchi |
| 2010/0010612 A1 | 1/2010 | Gelbart et al. |
| 2010/0016726 A1 | 1/2010 | Meier |
| 2010/0036227 A1 | 2/2010 | Cox et al. |
| 2010/0036284 A1 | 2/2010 | Laynes et al. |
| 2010/0041973 A1 | 2/2010 | Vu et al. |
| 2010/0041984 A1 | 2/2010 | Shapland et al. |
| 2010/0049062 A1 | 2/2010 | Ziv |
| 2010/0055153 A1 | 3/2010 | Majmudar |
| 2010/0055184 A1 | 3/2010 | Zeitels et al. |
| 2010/0057157 A1 | 3/2010 | Govari et al. |
| 2010/0060472 A1 | 3/2010 | Kimura et al. |
| 2010/0063401 A1 | 3/2010 | Nishina et al. |
| 2010/0076305 A1 | 3/2010 | Maier-Hein et al. |
| 2010/0076328 A1 | 3/2010 | Matsumura et al. |
| 2010/0081934 A1 | 4/2010 | Soltani et al. |
| 2010/0083719 A1 | 4/2010 | Peppmoller et al. |
| 2010/0094116 A1 | 4/2010 | Silverstein |
| 2010/0106011 A1 | 4/2010 | Byrd et al. |
| 2010/0113917 A1 | 5/2010 | Anderson |
| 2010/0114573 A1 | 5/2010 | Huang et al. |
| 2010/0117659 A1 | 5/2010 | Osadchy et al. |
| 2010/0130858 A1 | 5/2010 | Arai et al. |
| 2010/0143119 A1 | 6/2010 | Kooijman et al. |
| 2010/0152596 A1 | 6/2010 | Griffiths et al. |
| 2010/0152604 A1 | 6/2010 | Kaula et al. |
| 2010/0160772 A1 | 6/2010 | Gardeski et al. |
| 2010/0168557 A1 | 7/2010 | Deno et al. |
| 2010/0185097 A1 | 7/2010 | Hall |
| 2010/0198048 A1 | 8/2010 | Togawa |
| 2010/0198346 A1 | 8/2010 | Keogh et al. |
| 2010/0204569 A1 | 8/2010 | Burnside et al. |
| 2010/0204614 A1 | 8/2010 | Lindquist et al. |
| 2010/0210938 A1 | 8/2010 | Verard et al. |
| 2010/0210950 A1 | 8/2010 | Dunbar et al. |
| 2010/0217116 A1 | 8/2010 | Eck et al. |
| 2010/0222664 A1 | 9/2010 | Lemon et al. |
| 2010/0222786 A1 | 9/2010 | Kassab |
| 2010/0234724 A1 | 9/2010 | Jacobsen et al. |
| 2010/0234733 A1 | 9/2010 | Wahlheim |
| 2010/0249598 A1 | 9/2010 | Smith et al. |
| 2010/0258033 A1 | 10/2010 | Yang et al. |
| 2010/0268059 A1 | 10/2010 | Ryu et al. |
| 2010/0273895 A1 | 10/2010 | Stinchcomb et al. |
| 2010/0274150 A1 | 10/2010 | Harlev et al. |
| 2010/0291521 A1 | 11/2010 | Simon |
| 2010/0298702 A1 | 11/2010 | Rogers et al. |
| 2010/0298704 A1 | 11/2010 | Pelissier et al. |
| 2010/0298705 A1 | 11/2010 | Pelissier et al. |
| 2010/0298712 A1 | 11/2010 | Pelissier et al. |
| 2010/0312086 A9 | 12/2010 | Beatty et al. |
| 2010/0317981 A1 | 12/2010 | Grunwald |
| 2010/0318026 A1 | 12/2010 | Grunwald |
| 2010/0331712 A1 | 12/2010 | Rothenberg |
| 2011/0015496 A1 | 1/2011 | Sherman et al. |
| 2011/0015527 A1 | 1/2011 | Heasty et al. |
| 2011/0015533 A1 | 1/2011 | Cox et al. |
| 2011/0034823 A1 | 2/2011 | Gelbart et al. |
| 2011/0034940 A1 | 2/2011 | Payner |
| 2011/0040212 A1 | 2/2011 | Dietz et al. |
| 2011/0052694 A1 | 3/2011 | Stinchcomb et al. |
| 2011/0087105 A1 | 4/2011 | Ridley et al. |
| 2011/0087106 A1 | 4/2011 | Ridley et al. |
| 2011/0087107 A1 | 4/2011 | Lindekugel et al. |
| 2011/0106101 A1 | 5/2011 | Tortonese et al. |
| 2011/0112396 A1 | 5/2011 | Shachar et al. |
| 2011/0136242 A1 | 6/2011 | Marx et al. |
| 2011/0137156 A1 | 6/2011 | Razzaque et al. |
| 2011/0196235 A1 | 8/2011 | Dunbar et al. |
| 2011/0196248 A1 | 8/2011 | Grunwald |
| 2011/0196255 A1 | 8/2011 | Kassab |
| 2011/0224564 A1* | 9/2011 | Moon ..................... A61B 5/00 600/509 |
| 2011/0237935 A1 | 9/2011 | Kalpin et al. |
| 2011/0245659 A1 | 10/2011 | Ma et al. |
| 2011/0282187 A1 | 11/2011 | Harlev et al. |
| 2011/0282188 A1 | 11/2011 | Burnside et al. |
| 2011/0282285 A1 | 11/2011 | Blanchard et al. |
| 2011/0282686 A1 | 11/2011 | Venon et al. |
| 2011/0295108 A1 | 12/2011 | Cox et al. |
| 2011/0306859 A1 | 12/2011 | Saldivar et al. |
| 2011/0306867 A1 | 12/2011 | Gopinathan et al. |
| 2011/0313293 A1 | 12/2011 | Lindekugel et al. |
| 2012/0004564 A1 | 1/2012 | Dobak, III |
| 2012/0035460 A1 | 2/2012 | Stangenes et al. |
| 2012/0035539 A1 | 2/2012 | Tegg |
| 2012/0046562 A1 | 2/2012 | Powers et al. |
| 2012/0059249 A1 | 3/2012 | Verard et al. |
| 2012/0059270 A1 | 3/2012 | Grunwald |
| 2012/0059271 A1 | 3/2012 | Amitai et al. |
| 2012/0071751 A1 | 3/2012 | Sra et al. |
| 2012/0071759 A1 | 3/2012 | Hagy et al. |
| 2012/0071782 A1 | 3/2012 | Patil et al. |
| 2012/0078342 A1 | 3/2012 | Vollkron et al. |
| 2012/0095319 A1 | 4/2012 | Kondrosky et al. |
| 2012/0108950 A1 | 5/2012 | He et al. |
| 2012/0115007 A1 | 5/2012 | Felder et al. |
| 2012/0136242 A1 | 5/2012 | Qi et al. |
| 2012/0143029 A1 | 6/2012 | Silverstein et al. |
| 2012/0143078 A1 | 6/2012 | Kassab et al. |
| 2012/0172727 A1 | 7/2012 | Hastings et al. |
| 2012/0220854 A1 | 8/2012 | Messerly et al. |
| 2012/0265084 A1 | 10/2012 | Stewart et al. |
| 2012/0283582 A1 | 11/2012 | Mahapatra et al. |
| 2012/0296200 A1 | 11/2012 | Shachar et al. |
| 2012/0296213 A1 | 11/2012 | Mauldin, Jr. et al. |
| 2012/0310052 A1 | 12/2012 | Mahapatra et al. |
| 2012/0310066 A1 | 12/2012 | Shachar et al. |
| 2012/0310660 A1 | 12/2012 | Liu et al. |
| 2012/0316440 A1 | 12/2012 | Munrow et al. |
| 2013/0006100 A1 | 1/2013 | Shachar et al. |
| 2013/0006102 A1 | 1/2013 | Wilkes et al. |
| 2013/0018248 A1 | 1/2013 | Hurezan |
| 2013/0035590 A1 | 2/2013 | Ma et al. |
| 2013/0041254 A1 | 2/2013 | Hagy et al. |
| 2013/0041269 A1 | 2/2013 | Stahmann et al. |
| 2013/0060116 A1 | 3/2013 | Messerly et al. |
| 2013/0079628 A1 | 3/2013 | Groszmann et al. |
| 2013/0085416 A1 | 4/2013 | Mest |
| 2013/0090938 A1 | 4/2013 | Fishman et al. |
| 2013/0102890 A1 | 4/2013 | Dib |
| 2013/0102967 A1 | 4/2013 | Hanlon et al. |
| 2013/0123597 A1 | 5/2013 | Rothenberg |
| 2013/0131503 A1 | 5/2013 | Schneider et al. |
| 2013/0169272 A1 | 7/2013 | Eichler et al. |
| 2013/0213147 A1* | 8/2013 | Rice ..................... A43B 7/088 73/862.046 |
| 2013/0217999 A1 | 8/2013 | Burnside et al. |
| 2013/0223702 A1 | 8/2013 | Holsing et al. |
| 2013/0245434 A1 | 9/2013 | Messerly et al. |
| 2013/0281837 A1 | 10/2013 | Ridley et al. |
| 2013/0289417 A1 | 10/2013 | Grunwald et al. |
| 2013/0296691 A1 | 11/2013 | Ashe |

(56) References Cited

U.S. PATENT DOCUMENTS

| | | |
|---|---|---|
| 2013/0296693 A1 | 11/2013 | Wenzel et al. |
| 2013/0303878 A1 | 11/2013 | Nevo et al. |
| 2013/0303896 A1 | 11/2013 | Kalpin et al. |
| 2013/0303945 A1 | 11/2013 | Blumenkranz et al. |
| 2013/0317338 A1 | 11/2013 | Silverstein |
| 2013/0324841 A1 | 12/2013 | Kamen et al. |
| 2013/0338503 A1 | 12/2013 | Cohen et al. |
| 2013/0338517 A1 | 12/2013 | Rothenberg |
| 2013/0345555 A1 | 12/2013 | Kanade et al. |
| 2014/0005530 A1 | 1/2014 | Liu et al. |
| 2014/0031674 A1 | 1/2014 | Newman et al. |
| 2014/0046261 A1 | 2/2014 | Newman et al. |
| 2014/0066798 A1* | 3/2014 | Albert ............... A61B 5/0452 600/513 |
| 2014/0089836 A1 | 3/2014 | Damani et al. |
| 2014/0094694 A1 | 4/2014 | Moctezuma de la Barrera |
| 2014/0094768 A1 | 4/2014 | Stangenes et al. |
| 2014/0107475 A1 | 4/2014 | Cox et al. |
| 2014/0128712 A1 | 5/2014 | Banet et al. |
| 2014/0163356 A2 | 6/2014 | Burnside et al. |
| 2014/0180074 A1 | 6/2014 | Green et al. |
| 2014/0187917 A1 | 7/2014 | Clark et al. |
| 2014/0187990 A1 | 7/2014 | Banet et al. |
| 2014/0188133 A1 | 7/2014 | Misener |
| 2014/0221862 A1 | 8/2014 | Tambe |
| 2014/0228689 A1 | 8/2014 | Ishikawa et al. |
| 2014/0243659 A1 | 8/2014 | Rothenberg |
| 2014/0249428 A1 | 9/2014 | Ingold, Jr. et al. |
| 2014/0249505 A1 | 9/2014 | Bukhman |
| 2014/0253270 A1 | 9/2014 | Nicholls et al. |
| 2014/0257080 A1 | 9/2014 | Dunbar et al. |
| 2014/0275957 A1 | 9/2014 | Lupotti |
| 2014/0275990 A1 | 9/2014 | Hagy et al. |
| 2014/0276010 A1 | 9/2014 | Anderson |
| 2014/0303492 A1 | 10/2014 | Burnside et al. |
| 2014/0309624 A1 | 10/2014 | Bown et al. |
| 2014/0343398 A1 | 11/2014 | He et al. |
| 2015/0005621 A1 | 1/2015 | Liu |
| 2015/0018701 A1 | 1/2015 | Cox et al. |
| 2015/0025365 A1 | 1/2015 | Esguerra Wilczynski et al. |
| 2015/0025402 A1 | 1/2015 | Rothenberg |
| 2015/0051489 A1 | 2/2015 | Caluser et al. |
| 2015/0073285 A1 | 3/2015 | Albert et al. |
| 2015/0080716 A1 | 3/2015 | Powers et al. |
| 2015/0173723 A1 | 6/2015 | Bates et al. |
| 2015/0209008 A1 | 7/2015 | Ridley et al. |
| 2015/0209113 A1 | 7/2015 | Burkholz et al. |
| 2015/0216445 A1 | 8/2015 | Carmeli et al. |
| 2015/0216446 A1 | 8/2015 | Bukhman et al. |
| 2015/0223775 A1 | 8/2015 | Hamilton, Jr. |
| 2015/0245809 A1 | 9/2015 | Hagy et al. |
| 2015/0245872 A1 | 9/2015 | Hagy et al. |
| 2015/0246247 A1 | 9/2015 | Binnekamp et al. |
| 2015/0282734 A1 | 10/2015 | Schweikert et al. |
| 2015/0289781 A1 | 10/2015 | Grunwald et al. |
| 2015/0297114 A1 | 10/2015 | Cox et al. |
| 2015/0317810 A1 | 11/2015 | Grunwald et al. |
| 2015/0335310 A1 | 11/2015 | Bernstein et al. |
| 2015/0335383 A9 | 11/2015 | Cohen |
| 2016/0067449 A1 | 3/2016 | Misener et al. |
| 2016/0278869 A1 | 9/2016 | Grunwald |
| 2016/0374589 A1 | 12/2016 | Misener et al. |
| 2017/0000367 A1 | 1/2017 | Grunwald |
| 2017/0020561 A1 | 1/2017 | Cox et al. |
| 2017/0079548 A1 | 3/2017 | Silverstein et al. |
| 2017/0079552 A1 | 3/2017 | Grunwald |
| 2017/0079615 A1 | 3/2017 | Burnside et al. |
| 2017/0079681 A1 | 3/2017 | Burnside et al. |
| 2017/0086782 A1 | 3/2017 | Hagy et al. |
| 2017/0151022 A1 | 6/2017 | Jascob et al. |
| 2017/0215762 A1 | 8/2017 | Burnside et al. |
| 2017/0231700 A1 | 8/2017 | Cox et al. |
| 2017/0281029 A1 | 10/2017 | Messerly et al. |
| 2017/0348510 A1 | 12/2017 | Shevgoor et al. |
| 2017/0348511 A1 | 12/2017 | Burkholz et al. |
| 2018/0070856 A1 | 3/2018 | Grunwald |
| 2018/0103869 A1 | 4/2018 | Bukhman et al. |
| 2018/0116551 A1 | 5/2018 | Newman et al. |
| 2018/0145443 A1 | 5/2018 | Andreason et al. |
| 2018/0169389 A1 | 6/2018 | Lemon et al. |
| 2018/0296122 A1 | 10/2018 | Messerly et al. |
| 2018/0310955 A1 | 11/2018 | Lindekugel et al. |
| 2019/0069877 A1 | 3/2019 | Burnside et al. |
| 2019/0099108 A1 | 4/2019 | Messerly et al. |
| 2019/0246945 A1 | 8/2019 | Grunwald |
| 2019/0290208 A1 | 9/2019 | Toth et al. |
| 2020/0054858 A1 | 2/2020 | Newman et al. |
| 2020/0119488 A1 | 4/2020 | Stats et al. |
| 2020/0138332 A1 | 5/2020 | Newman et al. |
| 2020/0237255 A1 | 7/2020 | Silverstein et al. |
| 2020/0237403 A1 | 7/2020 | Southard et al. |
| 2020/0345983 A1 | 11/2020 | Misener |

FOREIGN PATENT DOCUMENTS

| | | |
|---|---|---|
| AU | 20009592 | 9/2000 |
| AU | 20015250 | 6/2001 |
| AU | 768362 B2 | 12/2003 |
| AU | 2001229024 B2 | 9/2005 |
| AU | 2001283703 B2 | 5/2006 |
| AU | 2006904933 | 9/2006 |
| AU | 2006202149 B2 | 3/2009 |
| AU | 2006283022 B2 | 2/2012 |
| CA | 1197745 A | 12/1985 |
| CA | 2420676 C | 7/2010 |
| CA | 2619909 C | 1/2014 |
| CN | 2031655 U | 2/1989 |
| CN | 1672649 A | 9/2005 |
| CN | 1913833 A | 2/2007 |
| CN | 101854853 A | 10/2010 |
| CN | 102209490 A | 10/2011 |
| CN | 102802514 A | 11/2012 |
| CN | 102821679 A | 12/2012 |
| CN | 103037761 A | 4/2013 |
| CN | 103037762 A | 4/2013 |
| CN | 103118591 A | 5/2013 |
| CN | 103189009 A | 7/2013 |
| DE | 4319033 C1 | 6/1994 |
| EP | 0362821 A1 | 4/1990 |
| EP | 0399536 A1 | 11/1990 |
| EP | 0359697 B1 | 11/1994 |
| EP | 0823261 A2 | 2/1998 |
| EP | 0928976 A2 | 7/1999 |
| EP | 1025805 A1 | 8/2000 |
| EP | 1015967 B1 | 4/2002 |
| EP | 1311226 A1 | 5/2003 |
| EP | 1504713 A1 | 2/2005 |
| EP | 1117331 B1 | 5/2005 |
| EP | 1117332 B1 | 8/2005 |
| EP | 1118019 B1 | 5/2006 |
| EP | 1717601 A2 | 11/2006 |
| EP | 1887940 A2 | 2/2008 |
| EP | 1932477 A1 | 6/2008 |
| EP | 2337491 A1 | 6/2011 |
| EP | 2440122 A1 | 4/2012 |
| EP | 2464407 A2 | 6/2012 |
| EP | 2482719 A1 | 8/2012 |
| EP | 2531098 A1 | 12/2012 |
| EP | 2575610 A1 | 4/2013 |
| EP | 2575611 A1 | 4/2013 |
| EP | 2603145 A2 | 6/2013 |
| EP | 2605699 A2 | 6/2013 |
| EP | 2474268 B1 | 7/2013 |
| EP | 2618727 A1 | 7/2013 |
| EP | 2632360 A1 | 9/2013 |
| EP | 2219526 B1 | 3/2014 |
| EP | 2712547 A1 | 4/2014 |
| EP | 2313143 B1 | 9/2014 |
| EP | 2992825 B1 | 5/2017 |
| EP | 2170162 B1 | 8/2017 |
| EP | 2265175 B1 | 8/2017 |
| FR | 2545349 B1 | 9/1986 |
| JP | 01097440 | 4/1989 |
| JP | 03173542 A | 7/1991 |

(56) References Cited

FOREIGN PATENT DOCUMENTS

| | | |
|---|---|---|
| JP | 9-503054 | 3/1997 |
| JP | 09-094298 A | 4/1997 |
| JP | 10043310 | 2/1998 |
| JP | 10290839 A | 11/1998 |
| JP | 11128237 A | 5/1999 |
| JP | 2001-145630 A | 5/2001 |
| JP | 2001161683 A | 6/2001 |
| JP | 2001-514533 A | 9/2001 |
| JP | 2001-524339 A | 12/2001 |
| JP | 2001340334 A | 12/2001 |
| JP | 2002520893 A | 7/2002 |
| JP | 2002-224069 A | 8/2002 |
| JP | 2002-529133 A | 9/2002 |
| JP | 2002-541947 A | 12/2002 |
| JP | 2003-010138 A | 1/2003 |
| JP | 2003501127 A | 1/2003 |
| JP | 2003061752 A | 3/2003 |
| JP | 2003299654 A | 10/2003 |
| JP | 2003334191 A | 11/2003 |
| JP | 2004505748 T | 2/2004 |
| JP | 2004515298 A | 5/2004 |
| JP | 2006508744 A | 3/2006 |
| JP | 2006-338526 A | 12/2006 |
| JP | 2007-000226 A | 1/2007 |
| JP | 2007-068989 A | 3/2007 |
| JP | 2007-105450 A | 4/2007 |
| JP | 2007-313122 A | 12/2007 |
| JP | 4090741 B2 | 5/2008 |
| JP | 2009/271123 A | 11/2009 |
| JP | 5010604 B2 | 8/2012 |
| JP | 2012-529929 A | 11/2012 |
| JP | 2013-518676 A | 5/2013 |
| JP | 2013-526959 A | 6/2013 |
| JP | 2013-526961 A | 6/2013 |
| RU | 2009101949 A | 7/2010 |
| WO | 1980002376 A1 | 11/1980 |
| WO | 1991012836 A1 | 9/1991 |
| WO | 1992003090 A1 | 3/1992 |
| WO | 1994003159 A1 | 2/1994 |
| WO | 1994004938 A1 | 3/1994 |
| WO | 1996005768 A1 | 2/1996 |
| WO | 1996007352 A1 | 3/1996 |
| WO | 1996041119 A1 | 12/1996 |
| WO | 1997/22395 A1 | 6/1997 |
| WO | 1997029683 A1 | 8/1997 |
| WO | 1997043989 A1 | 11/1997 |
| WO | 97/48438 A2 | 12/1997 |
| WO | 1998025159 A1 | 6/1998 |
| WO | 98/29032 A1 | 7/1998 |
| WO | 1998035611 A1 | 8/1998 |
| WO | 1999016495 A1 | 4/1999 |
| WO | 1999027837 A2 | 6/1999 |
| WO | 1999049407 A1 | 9/1999 |
| WO | 2000019906 A1 | 4/2000 |
| WO | 2000027281 A1 | 5/2000 |
| WO | 2000040155 A1 | 7/2000 |
| WO | 2000063658 A2 | 10/2000 |
| WO | 2000074775 A1 | 12/2000 |
| WO | 2001013792 A1 | 3/2001 |
| WO | 2001039683 A1 | 6/2001 |
| WO | 2001076479 A1 | 10/2001 |
| WO | 02/07794 A2 | 1/2002 |
| WO | 2002015973 A1 | 2/2002 |
| WO | 2002019905 A1 | 3/2002 |
| WO | 2002025277 A1 | 3/2002 |
| WO | 2002085442 A1 | 10/2002 |
| WO | 2003061752 A1 | 7/2003 |
| WO | 2003077759 A1 | 9/2003 |
| WO | 03/088833 A1 | 10/2003 |
| WO | 2003091495 A1 | 11/2003 |
| WO | 2004002303 A1 | 1/2004 |
| WO | 2004049970 A2 | 6/2004 |
| WO | 2005033524 A1 | 4/2005 |
| WO | 2005033574 A1 | 4/2005 |
| WO | 2005/089851 A1 | 9/2005 |
| WO | 2005117690 A1 | 12/2005 |
| WO | 2005117733 A2 | 12/2005 |
| WO | 2006074509 A1 | 7/2006 |
| WO | 2006074510 A1 | 7/2006 |
| WO | 2006078677 A2 | 7/2006 |
| WO | 2006103661 A2 | 10/2006 |
| WO | 2006111056 A1 | 10/2006 |
| WO | 2007002541 A2 | 1/2007 |
| WO | 2007005976 A1 | 1/2007 |
| WO | 2007014447 A1 | 2/2007 |
| WO | 2007034196 A2 | 3/2007 |
| WO | 2007067324 A1 | 6/2007 |
| WO | 2007069168 A2 | 6/2007 |
| WO | 2007109123 A2 | 9/2007 |
| WO | 2007126536 A2 | 11/2007 |
| WO | 2007144894 A1 | 12/2007 |
| WO | 2008005480 A1 | 1/2008 |
| WO | 2008024596 A2 | 2/2008 |
| WO | 2008028253 A1 | 3/2008 |
| WO | 2008083111 A1 | 7/2008 |
| WO | 2008097767 A2 | 8/2008 |
| WO | 2008118992 A1 | 10/2008 |
| WO | 2008126074 A2 | 10/2008 |
| WO | 2008129326 A1 | 10/2008 |
| WO | 2008131017 A2 | 10/2008 |
| WO | 2008136008 A2 | 11/2008 |
| WO | 2009000439 A1 | 12/2008 |
| WO | 2009002514 A2 | 12/2008 |
| WO | 2009003138 A1 | 12/2008 |
| WO | 2009009064 A1 | 1/2009 |
| WO | 2009057774 A1 | 5/2009 |
| WO | 2009063166 A1 | 5/2009 |
| WO | 2009067654 A1 | 5/2009 |
| WO | 2009070616 A2 | 6/2009 |
| WO | 2009100158 A1 | 8/2009 |
| WO | 2009123819 A2 | 10/2009 |
| WO | 2009126340 A1 | 10/2009 |
| WO | 2009129475 A1 | 10/2009 |
| WO | 2009129477 A1 | 10/2009 |
| WO | 2009134605 A2 | 11/2009 |
| WO | 2009137262 A2 | 11/2009 |
| WO | 2010002313 A1 | 1/2010 |
| WO | 2010018500 A1 | 2/2010 |
| WO | 2010022370 A1 | 2/2010 |
| WO | 2010027349 A1 | 3/2010 |
| WO | 2010027471 A2 | 3/2010 |
| WO | 2010029906 A1 | 3/2010 |
| WO | 2010030820 A1 | 3/2010 |
| WO | 2010132857 A1 | 11/2010 |
| WO | 2010132985 A1 | 11/2010 |
| WO | 2010/144922 A1 | 12/2010 |
| WO | 2010143196 A1 | 12/2010 |
| WO | 2011019760 A2 | 2/2011 |
| WO | 2011041450 A1 | 4/2011 |
| WO | 2011044421 A1 | 4/2011 |
| WO | 2011057289 A2 | 5/2011 |
| WO | 2011064209 A1 | 6/2011 |
| WO | 2011084593 A2 | 7/2011 |
| WO | 2011097312 A1 | 8/2011 |
| WO | 2011128052 A2 | 10/2011 |
| WO | 2011150358 A1 | 12/2011 |
| WO | 2011150376 A1 | 12/2011 |
| WO | 2012021542 A2 | 2/2012 |
| WO | 2012024577 A2 | 2/2012 |
| WO | 2012039866 A1 | 3/2012 |
| WO | 2012040487 A1 | 3/2012 |
| WO | 2012058461 A1 | 5/2012 |
| WO | 2012083245 A1 | 6/2012 |
| WO | 2012088535 A1 | 6/2012 |
| WO | 2012110955 A1 | 8/2012 |
| WO | 2012173697 A1 | 12/2012 |
| WO | 2013006713 A1 | 1/2013 |
| WO | 2013006817 A1 | 1/2013 |
| WO | 2013034175 A1 | 3/2013 |
| WO | 2014042329 A1 | 3/2014 |
| WO | 2014052894 A2 | 4/2014 |
| WO | 2014062728 A1 | 4/2014 |
| WO | 2014072238 A1 | 5/2014 |
| WO | 2014137977 A1 | 9/2014 |

(56) References Cited

FOREIGN PATENT DOCUMENTS

| WO | 2014138652 A1 | 9/2014 |
|---|---|---|
| WO | 2014138918 A1 | 9/2014 |
| WO | 2015/055797 A1 | 4/2015 |
| WO | 2015048514 A1 | 4/2015 |
| WO | 2015073962 A1 | 5/2015 |
| WO | 2015/120256 A2 | 8/2015 |
| WO | 2016/210325 A1 | 12/2016 |
| WO | 2017096487 A1 | 6/2017 |
| WO | 2017214428 A1 | 12/2017 |
| WO | 2018/112252 A1 | 6/2018 |
| WO | 2018134726 A1 | 7/2018 |
| WO | 2020/160315 A1 | 8/2020 |

OTHER PUBLICATIONS

U.S. Appl. No. 15/365,698, filed Nov. 30, 2016 Non-Final Office Action dated Dec. 14, 2017.
U.S. Appl. No. 15/365,734, filed Nov. 30, 2016 Non-Final Office Action dated Feb. 23, 2018.
U.S. Appl. No. 15/365,734, filed Nov. 30, 2016 Notice of Allowance dated Jun. 4, 2018.
U.S. Appl. No. 15/365,752, filed Nov. 30, 2016 Final Office Action dated Jul. 12, 2018.
U.S. Appl. No. 15/365,752, filed Nov. 30, 2016 Non-Final Office Action dated Dec. 13, 2017.
U.S. Appl. No. 15/365,752, filed Nov. 30, 2016 Notice of Allowance dated Nov. 6, 2018.
U.S. Appl. No. 15/365,872, filed Nov. 30, 2016 Non-Final Office Action dated Aug. 27, 2018.
U.S. Appl. No. 15/365,872, filed Nov. 30, 2016 Notice of Allowance dated Dec. 21, 2018.
U.S. Appl. No. 15/365,872, filed Nov. 30, 2016 Restriction Requirement dated Apr. 5, 2018.
U.S. Appl. No. 15/418,475, filed Jan. 27, 2017 Restriction Requirement dated Jul. 23, 2019.
U.S. Appl. No. 15/585,051, filed May 2, 2017 Examiner's Answer dated May 2, 2019.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.
U.S. Appl. No. 15/585,051, filed May 2, 2017 Non-Final Office Action dated Jul. 14, 2017.
U.S. Appl. No. 15/816,932, filed Nov. 17, 2017 Non-Final Office Action dated Aug. 22, 2019.
U.S. Appl. No. 15/900,623, filed Feb. 20, 2018 Final Office Action dated Sep. 20, 2018.
U.S. Appl. No. 15/900,623, filed Feb. 20, 2018 Non-Final Office Action dated Jul. 16, 2019.
U.S. Appl. No. 15/900,623, filed Feb. 20, 2018 Non-Final Office Action dated May 3, 2018.
U.S. Appl. No. 29/428,649, filed Aug. 1, 2012 Notice of Allowance dated Jul. 5, 2013.
Valdivieso, J.R. Perez, et al., Evaluation of a formula for optimal positioning of a central venous catheter inserted through the right internal jugular vein, Rev. Esp. Anestesiol. Reanim. 2003; 50: 77-79.
VasoNova Inc, Vascular navigation system for accurate placement of PICCs, Start-Up Emerging Medical Ventures, pp. 44-45, vol. 14 No. 7, Jul.-Aug. 2009.
Vesely, Thomas M. et al., Central Venous Catheter Tip Position: A Continuing Controversy, J Vasc Intery Radiol 2003; 14:527-534.
VIASYS Health Care Inc. Cortrak © Fact Sheet, 2005.
VIASYS Healthcare MedSystems, Navigator® Benefits, 2008.
VIASYS Healthcare MedSystems, Navigator® Research in Cost Justification, 2008.
VIASYS MedSystems, Cortrak™ Systems Brochure, 2005.
Volcano ComboMap Features and Benefits/Technical Specifications, 2 pages, 2011.

Watters, et al. "Use of Electrocardiogram to Position Right Atrial Catheters During Surgery." Annals of Surgery, vol. 225, No. 2, pp. 165-171, 1997.
Welch Allyn Cardioperfect® PC-Based Resting ECG, 2003.
Wilson, R. G. et al, Right Atrial Electrocardiography in Placement of Central Venous Catheters, The Lancet, pp. 462-463, Feb. 27, 1988.
Wong, Jeffrey J. et al., Azygos Tip Placement for Hemodialysis Catheters in Patients with Superior Vena Cava Occlusion, Cardiovasc Intervent Radiol (2006) 29:143-146.
Worley, Seth J. "Use of a Real-Time Three-Dimensional Magenetic Navigation System for Radiofrequency Ablation of Accessory Pathways." PACE, vol. 21 pp. 1636-1643, Aug. 1998.
Yilmazlar A et al, Complications of 1303 Central Venous Cannulations, J R Soc Med, pp. 319-321, vol. 90 No. 6, Jun. 1997 (Abstract only).
Yoon, SZ et al, Usefulness of the Carina as a Radiographic Landmark for Central Venous Catheter Placement in Paediatric Patients, Br J Anaesth, Jul. 2005.
Yoshida, Teruhisa et al, Detection of Concealed Left Sided Accessory Atrioventricular Pathway by P Wave Signal Averaged Electrocardiogram, J Am Coll Cardiol, pp. 55-62, 1999.
Zaaroor, et al. "Novel Magnetic Technology for Intraoperative Intracranial Frameless Navigation: In Vivo and in Vitro Results." Neurosurgery, vol. 48, No. 5. pp. 1100-1107, May 2001.
Zachariou, Zacharias et al., Intra-atrial ECG recording: a new and safe method for implantation of Broviac catheters in children, Pediatr Surg Int (1994) 9: 457-458.
Zaidi, Naveed A., et al. "Room temperature magnetic order in an organic magnet derived from polyaniline." 2004, Polymer, vol. 45, pp. 5683-5689.
U.S. Appl. No. 14/201,300, filed Mar. 7, 2014 Final Office Action dated May 5, 2016.
U.S. Appl. No. 14/201,300, filed Mar. 7, 2014 Non-Final Office Action dated Aug. 24, 2016.
U.S. Appl. No. 14/201,300, filed Mar. 7, 2014 Non-Final Office Action dated Jan. 6, 2016.
U.S. Appl. No. 14/201,300, filed Mar. 7, 2014 Non-Final Office Action dated Mar. 30, 2017.
U.S. Appl. No. 14/270,241, filed May 5, 2014 Non-Final Office Action dated Apr. 23, 2015.
U.S. Appl. No. 14/270,241, filed May 5, 2014 Notice of Allowance dated Oct. 7, 2015.
U.S. Appl. No. 14/309,511, filed Jun. 19, 2014 Non-Final Office Action, dated Sep. 24, 2015.
U.S. Appl. No. 14/309,511, filed Jun. 19, 2014 Notice of Allowance, dated Jul. 26, 2016.
U.S. Appl. No. 14/317,501, filed Jun. 27, 2014 Advisory Action dated Sep. 16, 2015.
U.S. Appl. No. 14/317,501, filed Jun. 27, 2014 Decision on Appeal dated Nov. 17, 2017.
U.S. Appl. No. 14/317,501, filed Jun. 27, 2014 Examiners Answer dated Jun. 30, 2016.
U.S. Appl. No. 14/317,501, filed Jun. 27, 2014 Final Office Action dated Jul. 1, 2015.
U.S. Appl. No. 14/317,501, filed Jun. 27, 2014 Non-Final Office Action dated Mar. 3, 2015.
U.S. Appl. No. 14/317,501, filed Jun. 27, 2014 Non-Final Office Action dated Sep. 12, 2014.
U.S. Appl. No. 14/317,501, filed Jun. 27, 2014 Notice of Allowance dated Feb. 9, 2018.
U.S. Appl. No. 14/449,061, filed Jul. 31, 2014 Final Office Action dated Nov. 6, 2015.
U.S. Appl. No. 14/449,061, filed Jul. 31, 2014 Non-Final Office Action dated Apr. 27, 2015.
U.S. Appl. No. 14/449,061, filed Jul. 31, 2014 Notice of Allowance dated Apr. 13, 2016.
U.S. Appl. No. 14/498,887, filed Sep. 26, 2014 Advisory Action dated Aug. 22, 2016.
U.S. Appl. No. 14/498,887, filed Sep. 26, 2014 Final Office Action dated Jun. 15, 2016.
U.S. Appl. No. 14/498,887, filed Sep. 26, 2014 Non-Final Office Action dated Feb. 19, 2016.

(56) References Cited

OTHER PUBLICATIONS

U.S. Appl. No. 14/506,552, filed Oct. 3, 2014 Non-Final Office Action dated Oct. 1, 2015.
U.S. Appl. No. 14/548,151, filed Nov. 19, 2014 Advisory Action dated Aug. 1, 2017.
U.S. Appl. No. 14/548,151, filed Nov. 19, 2014 Advisory Action dated Jul. 22, 2016.
U.S. Appl. No. 14/548,151, filed Nov. 19, 2014 Final Office Action dated Apr. 19, 2017.
U.S. Appl. No. 14/548,151, filed Nov. 19, 2014 Non-Final Office Action dated Jun. 5, 2015.
U.S. Appl. No. 14/548,151, filed Nov. 19, 2014 Non-Final Office Action dated Sep. 21, 2017.
U.S. Appl. No. 14/548,151, filed Nov. 19, 2014 Non-Final Office Action dated Sep. 28, 2016.
U.S. Appl. No. 14/615,932, filed Feb. 6, 2015 Non-Final Office dated Dec. 29, 2016.
U.S. Appl. No. 14/788,305, filed Jun. 30, 2015 Advisory Action dated Oct. 19, 2018.
U.S. Appl. No. 14/788,305, filed Jun. 30, 2015 Final Office Action dated Jul. 27, 2018.
U.S. Appl. No. 14/788,305, filed Jun. 30, 2015 Non-Final Office Action dated Jan. 10, 2018.
U.S. Appl. No. 41/788,305, filed Jun. 30, 2015 Notice of Allowance dated Nov. 15, 2018.
U.S. Appl. No. 14/788,305, filed Jun. 30, 2015 Restriction Requirement dated Aug. 25, 2017.
U.S. Appl. No. 14/846,496, filed Sep. 4, 2015 Non-Final Office Action dated Nov. 25, 2016.
U.S. Appl. No. 14/996,247, filed Jan. 15, 2016 Non-Final Office Action dated Jul. 18, 2019.
U.S. Appl. No. 14/996,247, filed Jan. 15, 2016 Restriction Requirement dated Mar. 22, 2019.
U.S. Appl. No. 15/160,958, filed May 20, 2016 Advisory Action dated Jul. 10, 2017.
U.S. Appl. No. 15/160,958, filed May 20, 2016 Final Office Action dated Apr. 21, 2017.
U.S. Appl. No. 15/160,958, filed May 20, 2016 Non-Final Office Action dated Dec. 15, 2016.
U.S. Appl. No. 15/160,958, filed May 20, 2016 Notice of Allowance dated Jul. 26, 2017.
U.S. Appl. No. 15/192,561, filed Jun. 24, 2016 Final Office Action dated Nov. 1, 2018.
U.S. Appl. No. 15/192,561, filed Jun. 24, 2016 Non-Final Office Action dated Apr. 6, 2018.
U.S. Appl. No. 15/266,977, filed Sep. 15, 2016 Non-Final Office Action dated Oct. 30, 2018.
U.S. Appl. No. 15/284,355, filed Oct. 3, 2016 Advisory Action dated Aug. 13, 2018.
U.S. Appl. No. 15/284,355, filed Oct. 3, 2016 Final Office Action dated May 24, 2018.
U.S. Appl. No. 15/284,355, filed Oct. 3, 2016 Non-Final Office Action dated Apr. 24, 2017.
U.S. Appl. No. 15/284,355, filed Oct. 3, 2016 Non-Final Office Action dated Nov. 17, 2017.
U.S. Appl. No. 15/284,355, filed Oct. 3, 2016 Notice of Allowance dated Feb. 21, 2019.
U.S. Appl. No. 15/365,698, filed Nov. 30, 2016 Final Office Action dated Jul. 12, 2018.
EP 10786978.6 filed Dec. 19, 2011 Office Action dated Jan. 16, 2019.
EP 10821193.9 filed Mar. 27 2012 Partial European Search Report dated Oct. 9, 2015.
EP 11 818 828.3 filed Mar. 18, 2013 Extended European Search Report dated Dec. 10, 2014.
EP 11740309.7 filed Aug. 23, 2012 Extended European Search Report dated Aug. 3, 2015.
EP 11787515.3 filed Dec. 12, 2012 partial European search report dated Jun. 23, 2015.
EP 11787515.3 filed Dec. 12, 2012 partial European search report dated Oct. 27, 2015.
EP 11787527.8 filed Dec. 19 2012 Extended European Search Report dated Oct. 9, 2015.
EP 11787527.8 filed Dec. 19, 2012 partial European search report dated May 26, 2015.
EP 11827551.0 filed Feb. 7, 2013 Extended European Search Report dated Sep. 19, 2017.
EP 11837113.7 filed May 28, 2013 Extended European Search Report dated Apr. 24, 2014.
EP 11850625.2 filed Jul. 22, 2013 Extended European Search Report dated Jun. 21, 2017.
EP 11850625.2 filed Jul. 22, 2013 Office Action dated Feb. 25, 2019.
EP 11850625.2 filed Jul. 22, 2013 Office Action dated Sep. 24, 2018.
EP 12177438.4 filed Jul. 23, 2012 Communication dated Jan. 13, 2014.
EP 12177438.4 filed Jul. 23, 2012 European Search Report dated Dec. 4, 2012.
EP 12177438.4 filed Jul. 23, 2012 European Search Report dated Jun. 7, 2015.
EP 12177438.4 filed Jul. 23, 2012 Examination Report dated Dec. 5, 2014.
EP 12177438.4 filed Jul. 23, 2012 extended European Search Report dated Mar. 25, 2013.
EP 12807886.2 filed Jan. 15, 2014 Extended European Search Report dated Feb. 6, 2015.
EP 13194818.4 filed Nov. 28, 2013 extended European search report dated Feb. 28, 2014.
EP 13840356.3 filed Apr. 27, 2015 Extended European Search Report dated Mar. 22, 2017.
EP 13840356.3 filed Apr. 27, 2015 Partial European Search Report dated Oct. 19, 2016.
EP 13846380.7 filed May 15, 2015 Extended European Search Report dated Sep. 30, 2016.
EP 13846380.7 filed May 15, 2015 Partial European Search Report dated Sep. 30, 2016.
EP 14151268.1 filed Jan. 15, 2014 European Search Report dated Feb. 21, 2014.
EP 14197137.4 filed Dec. 10, 2014 Extended European Search Report dated Nov. 4, 2015.
EP 14197137.4 filed Dec. 10, 2014 Office Action dated Apr. 5, 2018.
EP 14197137.4 filed Dec. 10, 2014 Office Action dated, Sep. 20, 2017.
EP 14197137.4 filed Dec. 10, 2014, Office Action dated Nov. 21, 2018.
EP 14197137.4 filed Dec. 10, 2014, Partial European Search Report dated May 29, 2015.
EP 14761249.3 Filed Sep. 3, 2015 Extended European Search Report dated Sep. 19, 2016.
EP 14761249.3 Filed Sep. 3, 2015 Office Action dated Sep. 28, 2017.
EP 15179061.5 filed Jul. 30, 2015 Extended European Search Report dated Jan. 14, 2016.
EP 15179061.5 filed Jul. 30, 2015 Partial European Search Report dated Jan. 17, 2018.
EP 15746326.6 filed Jul. 1, 2016 Extended European Search Report dated Jun. 9, 2017.
EP 15746326.6 filed Jul. 1, 2016 Office Action dated Jan. 29, 2019.
EP 17157118.5 filed Feb. 21, 2017 Extended European Search Report dated Jun. 8, 2017.
EP 17186624.7 filed Aug. 17, 2017 Extended European Search Report dated Jan. 17, 2018.
EP 17186624.7 filed Aug. 17, 2017 Partial European Search Report dated Jan. 17, 2018.
EP14197136.6 filed Dec. 10, 2014 Extended European Search Report dated May 26, 2015.
EP14197136.6 filed Dec. 10, 2014 Office Action dated Nov. 21, 2018.
Fearon, William F et al, Evaluating Intermediate Coronary Lesions in the Cardiac Catheterization Laboratory, vol. 4, No. 1, 7 pages, Reviews in Cardiovascular Medicine, 2003.

(56) References Cited

OTHER PUBLICATIONS

Felleiter P et al, Use of Electrocardiographic Placement Control of Central Venous Catheters in Austria, Acta Med Austriaca, pp. 109-113, vol. 26 No. 3, 1999 (Abstract only).
Forauer, AR et al, Change in Peripherally Inserted Central Catheter Tip Location with Abduction and Adduction of the Upper Extremity, J Vasc Interv Radiol, pp. 1315-1318, vol. 11 No. 10, Nov.-Dec. 2000.
Frassinelli, P et al, Utility of Chest Radiographs after Guidewire Exchanges of Central Venous Catheters, Crit Care Med, pp. 611-615, vol. 26 No. 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
GB Application 0800474.9 filed Aug. 24, 2006 Office Action dated Mar. 17, 2010.
Gebauer, B et al, Ultrasound and Fluoroscopy-guided Implantation of Peripherally Inserted Central Venous Catheters (PICCs), ROFO, pp. 386-391, vol. 176 No. 3, Mar. 2004 (Abstract only).
U.S. Appl. No. 11/552,094, filed Oct. 23, 2006 Notice of Allowance dated May 20, 2010.
U.S. Appl. No. 12/104,253, filed Apr. 16, 2008 Final Office Action dated Jul. 27, 2011.
U.S. Appl. No. 12/104,253, filed Apr. 16, 2008 Non-Final Office Action dated Nov. 29, 2010.
U.S. Appl. No. 12/323,273, filed Nov. 25, 2008 Non-Final Office Action dated Jun. 8, 2012.
U.S. Appl. No. 12/369,625, filed Feb. 11, 2009 Final Office Action dated Feb. 23, 2012.
U.S. Appl. No. 12/369,625, filed Feb. 11, 2009 Notice of Allowance dated Oct. 5, 2012.
U.S. Appl. No. 12/369,625, filed Feb. 11, 2009 Notice of Panel Decision dated Aug. 1, 2012.
U.S. Appl. No. 12/369,625, filed Feb. 11, 2009 Non-Final Office Action dated Jul. 20, 2011.
U.S. Appl. No. 12/426,175, filed Apr. 17, 2009 Advisory Action dated Nov. 26, 2013.
U.S. Appl. No. 12/426,175, filed Apr. 17, 2009 Decision on Appeal dated Nov. 7, 2016.
U.S. Appl. No. 12/426,175, filed Apr. 17, 2009 Examinees Answer dated Oct. 7, 2014.
U.S. Appl. No. 12/426,175, filed Apr. 17, 2009 Final Office Action dated Aug. 2, 2013.
U.S. Appl. No. 12/426,175, filed Apr. 17, 2009 Final Office Action dated Jan. 31, 2014.
U.S. Appl. No. 12/426,175, filed Apr. 17, 2009 Non-Final Office Action dated Dec. 3, 2012.
U.S. Appl. No. 12/426,175, filed Apr. 17, 2009 Notice of Allowance dated Dec. 13, 2016.
U.S. Appl. No. 12/427,244, filed Apr. 21, 2009 Non-Final Office Action dated Jan. 19, 2012.
U.S. Appl. No. 12/545,762, filed Aug. 21, 2009 Final Office Action dated Apr. 10, 2017.
U.S. Appl. No. 12/545,762, filed Aug. 21, 2009 Final Office Action dated Mar. 7, 2013.
U.S. Appl. No. 12/545,762, filed Aug. 21, 2009 Non-Final Office Action dated Aug. 1, 2012.
U.S. Appl. No. 12/545,762, filed Aug. 21, 2009 Non-Final Office Action dated Dec. 13, 2013.
U.S. Appl. No. 12/545,762, filed Aug. 21, 2009 Non-Final Office Action dated Feb. 16, 2016.
U.S. Appl. No. 12/545,762, filed Aug. 21, 2009 Non-Final Office Action dated Nov. 7, 2014.
U.S. Appl. No. 12/545,762, filed Aug. 21, 2009 Non-Final Office Action dated Sep. 11, 2015.
U.S. Appl. No. 12/545,762, filed Aug. 21, 2009 Non-Final Office Action dated Sep. 26, 2016.
U.S. Appl. No. 12/545,762, filed Aug. 21, 2009 Notice of Panel Decision dated Jul. 14, 2017.
U.S. Appl. No. 12/557,401, filed Sep. 10, 2009 Non-Final Office Action dated Apr. 24, 2012.
U.S. Appl. No. 12/557,401, filed Sep. 10, 2009 Non-Final Office Action dated Jan. 6, 2014.
U.S. Appl. No. 12/575,456, filed Oct. 7, 2009 Non-Final Office Action dated Oct. 5, 2012.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 12/815,331, filed Jun. 14, 2010 Advisory Action dated Mar. 5, 2015.
U.S. Appl. No. 12/815,331, filed Jun. 14, 2010 Advisory Action dated Oct. 4, 2013.
U.S. Appl. No. 12/815,331, filed Jun. 14, 2010 Final Office Action dated Dec. 23, 2014.
U.S. Appl. No. 12/815,331, filed Jun. 14, 2010 Final Office Action dated Jul. 26, 2013.
U.S. Appl. No. 12/815,331, filed Jun. 14, 2010 Final Office Action dated Nov. 4, 2015.
U.S. Appl. No. 12/815,331, filed Jun. 14, 2010 Non-Final Office Action dated Jan. 22, 2013.
U.S. Appl. No. 12/815,331, filed Jun. 14, 2010 Non-Final Office Action dated Jul. 2, 2014.
U.S. Appl. No. 12/815,331, filed Jun. 14, 2010 Non-Final Office Action dated Jun. 1, 2015.
U.S. Appl. No. 12/854,083, filed Aug. 10, 2010 Advisory Action dated Sep. 8, 2014.
U.S. Appl. No. 12/854,083, filed Aug. 10, 2010 Final Office Action dated Aug. 15, 2013.
U.S. Appl. No. 12/854,083, filed Aug. 10, 2010 Final Office Action dated Aug. 21, 2015.
U.S. Appl. No. 12/854,083, filed Aug. 10, 2010 Final Office Action dated Jul. 1, 2014.
U.S. Appl. No. 12/854,083, filed Aug. 10, 2010 Non-Final Office Action dated Feb. 1, 2016.
U.S. Appl. No. 12/854,083, filed Aug. 10, 2010 Non-Final Office Action dated Jan. 29, 2013.
U.S. Appl. No. 12/854,083, filed Aug. 10, 2010 Non-Final Office Action dated Jan. 29, 2014.
U.S. Appl. No. 12/854,083, filed Aug. 10, 2010 Non-Final Office Action dated Mar. 16, 2015.
U.S. Appl. No. 12/878,915, filed Sep. 9, 2010 Final Office Action dated Sep. 26, 2012.
U.S. Appl. No. 12/878,915, filed Sep. 9, 2010 Non-Final Office Action dated Mar. 15, 2012.
U.S. Appl. No. 12/878,915, filed Sep. 9, 2010 Notice of Allowance dated Jan. 8, 2013.
U.S. Appl. No. 12/893,916, filed Sep. 29, 2010 Advisory Action dated Aug. 15, 2014.
EP 11827551.0 filed Feb. 7, 2013 Office Action dated Mar. 13, 2020.
EP 20154593.6 filed Jan. 30, 2020 Extended European Search Report dated Jun. 2, 2020.
U.S. Appl. No. 14/201,300, filed Mar. 7, 2014 Notice of Allowance dated May 8, 2020.
U.S. Appl. No. 15/418,475, filed Jan. 27, 2017 Advisory Action dated May 28, 2020.
U.S. Appl. No. 15/585,051, filed May 2, 2017 Board Decision dated Apr. 21, 2020.
U.S. Appl. No. 15/625,842, filed Jun. 16, 2017 Non-Final Office Action dated Mar. 18, 2020.
U.S. Appl. No. 15/816,932, filed Nov. 17, 2017 Advisory Action dated Jun. 18, 2020.
U.S. Appl. No. 15/836,741, filed Jan. 8, 2017 Non-Final Office Action dated Jun. 12, 2020.
U.S. Appl. No. 15/900,623, filed Feb. 20, 2018 Final Office Action dated Jun. 12, 2020.
PCT/US2019/055716 filed Oct. 10, 2019 International Search Report and Written Opinion dated Feb. 4, 2020.
U.S. Appl. No. 14/141,046, filed Dec. 26, 2013 Board Decision dated Nov. 26, 2019.

(56) References Cited

OTHER PUBLICATIONS

U.S. Appl. No. 14/201,300, filed Mar. 7, 2014 Final Office Action dated Mar. 9, 2020.
U.S. Appl. No. 14/201,300, filed Mar. 7, 2014 Non-Final Office Action dated Nov. 27, 2019.
U.S. Appl. No. 14/996,247, filed Jan. 15, 2016 Advisory Action dated Feb. 20, 2020.
U.S. Appl. No. 14/996,247, filed Jan. 15, 2016 Final Office Action dated Dec. 11, 2019.
U.S. Appl. No. 15/365,698, filed Nov. 30, 2016 Notice of Allowance dated Nov. 4, 2019.
U.S. Appl. No. 15/418,475, filed Jan. 27, 2017 Final Office Action dated Apr. 2, 2020.
U.S. Appl. No. 15/418,475, filed Jan. 27, 2017 Non-Final Office Action dated Oct. 18, 2019.
U.S. Appl. No. 15/816,932, filed Nov. 17, 2017 Final Office Action dated Feb. 28, 2020.
U.S. Appl. No. 15/836,741, filed Jan. 8, 2017 Restriction Requirement dated Mar. 3, 2020.
U.S. Appl. No. 15/900,623, filed Feb. 20, 2018 Non-Final Office Action dated Dec. 30, 2019.
CN 201180052587.5 filed Apr. 28, 2013 Office Action dated Feb. 24, 2016.
CN 201180052587.5 filed Apr. 28, 2013 Second Office Action dated Aug. 19, 2015.
CN 201180068309.9 filed Aug. 22, 2013 First Office Action dated Oct. 16, 2014.
CN 201180068309.9 filed Aug. 22, 2013 Second Office Action dated May 6, 2015.
CN 201180068309.9 filed Aug. 22, 2013 Third Office Action dated Sep. 2, 2015.
CN 201280033189.3 filed Jan. 3, 2014 First Office Action dated Apr. 3, 2014.
CN 201280033189.3 filed Jan. 3, 2014 Second Office Action dated Sep. 14, 2015.
CN 201380051172.5 filed Mar. 30, 2015 Office Action dated Jan. 16, 2018.
CN 201380051172.5 filed Mar. 30, 2015 Office Action dated Jul. 30, 2018.
CN 201380051172.5 filed Mar. 30, 2015 Office Action dated May 2, 2017.
CN 201380065663.5 filed Jun. 15, 2015 Office Action dated Mar. 15, 2017.
CN 201380065663.5 filed Jun. 15, 2015 Office Action dated Oct. 10, 2017.
CN 201410009216.4 filed Jan. 8, 2014 Office Action dated Jun. 15, 2016.
CN 201410009216.4 filed Jan. 8, 2014 Second Office Action dated Sep. 25, 2015.
CN 201480010988.8 filed Aug. 27, 2015 Office Action dated Aug. 17, 2018.
CN 201480010988.8 filed Aug. 27, 2015 Office Action dated Dec. 13, 2017.
CN 201510144728.6 filed Apr. 17, 2015 Office Action dated Aug. 29, 2017.
CN 201510144728.6 filed Apr. 17, 2015 Office Action dated Jan. 23, 2017.
CN 201580007645.0 filed Aug. 8, 2016 Office Action dated Sep. 12, 2018.
CN 201610127217.8 filed Mar. 7, 2016 Office Action dated Dec. 28, 2017.
CN 201610127217.8 filed Mar. 7, 2016 Office Action dated Jun. 11, 2018.
CN 201610127217.8 filed Mar. 7, 2016 Office Action dated Nov. 19, 2018.
CN 201610166569.4 filed Dec. 23, 2010, Office Action dated Nov. 1, 2017.
CO 15110530 filed May 14, 2015 Office Action dated May 8, 2017.
CO 15110530 filed May 14, 2015 Office Action dated Nov. 25, 2016.
Colley, Peter S et al, ECG-Guided Placement of Sorenson CVP Catheters via Arm Veins, Anesthesia and Analgesia, pp. 953-956, vol. 63, 1984.
Collier, PE et al, Cardiac Tamponade from Central Venous Catheters, Am J Surg, pp. 212-214, vol. 176 No. 2, Aug. 1998.
ComboWire® Pressure/Flow Guide Wire Ref 9500 Series, Instructions for Use, Apr. 2011.
Corsten, et al., "Central Placement Catheter Placement Using the ECG-Guided Cavax-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Cullinane, DC et al, The Futility of Chest Roentgenograms Following Routine Central Venous Line Changes, Am J Surg, pp. 283-285, vol. 176 No. 3, Sep. 1998.
Curet, Myriam J. et al., University and Practice-based Physicians' Input on the Content of a Surgical Curriculum, The American Journal of SURGERY® vol. 178 Jul. 1999, 78-84.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.
DELTEC Cath-Finder® Tracking System Operation Manual, 1994.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No. 9, Sep. 1989 (Abstract only).
Enrique Company-Bosch, "ECG Front-End Design is Simplified with MicroConverter." Analog Dialogue 37-11, (dated Nov. 2003).
EP 08855396.1 filed Jun. 15, 2010 European Search Report dated Jul. 31, 2012.
EP 08855396.1 filed Jun. 15, 2010 Intent to Grant dated Jul. 5, 2013.
EP 09707467.8 supplemental European search report dated Jun. 18, 2013.
EP 09743249.6 filed Oct. 18, 2010 Extended European Search Report dated Jan. 13, 2016.
EP 09743249.6 filed Oct. 18, 2010 Intention to Grant dated Mar. 2, 2017.
EP 09808901.4 filed Aug. 21, 2009 European Search Report dated May 23, 2012.
EP 09808901.4 filed Aug. 21, 2009 Examination Report dated May 10, 2013.
EP 09813632.8 filed Apr. 5, 2011 European Search Report dated Jul. 4, 2012.
EP 09813632.8 filed Apr. 5, 2011 Office Action dated Apr. 30, 2013.
EP 09813632.8 filed Apr. 5, 2011 Summons to Attend Oral Proceedings dated Apr. 16, 2014.
EP 10 808 660.4 filed Feb. 15, 2012 Extended European Search Report dated Mar. 4, 2014.
EP 10786978.6 filed Dec. 19, 2011 Extended European Search Report dated Mar. 7, 2014.
EP 10786978.6 filed Dec. 19, 2011 Office Action dated Aug. 11, 2017.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
Chang, Thomas C. et al., Are Routine Ch Ladiographs Necessary After Image-Guided Placement of Internal Jugular Central Venous Access Devices?, AJR Feb. 1998;170:335-337.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.

(56) References Cited

OTHER PUBLICATIONS

Cheng, KI et al, A Novel Approach of Intravenous Electrocardiograph Technique in Correct Position the Long-Term Central Venous Catheter, Kaohsiung J Med Sci, pp. 241-247, vol. 16 No. 5, May 2000 (Abstract only).
Cheung, P., et al., The Effect of a Disposable Probe Cover on Pulse Oximetry, Anaesth Intensive Care 2002; 30: 211-214.
Chu, et al., "Accurate Central Venous Port-A Catheter Placement: Intravenous Electrocardiography and Surface Landmark Techniques Compared by Using Transesophageal Echocardiography." The International Anesthesia Research Society, vol. 98, pp. 910-914, 2004.
Claasz, Antonia et al, A Study of the Relationship of the Superior Vena Cava to the Bony Landmarks of the Sternum in the Supine Adult: Implications for Magnetic Guidance Systems, Journal, vol. 12 No. 3, Java, Jul. 24, 2007.
Clifford, et al. "Assessment of Hepatic Motion Secondary to Respiration for Computer Assisted Interventions." Computer Aided Surgery, vol. 7, pp. 291-299, 2002.
CN 200880012117.4 filed Apr. 16, 2008 First Office Action dated Dec. 23, 2011.
CN 200880012117.4 filed Apr. 16, 2008 Fourth Office Action dated Sep. 4, 2013.
CN 200880012117.4 filed Apr. 16, 2008 Second Office Action dated Oct. 8, 2012.
CN 200880012117.4 filed Apr. 16, 2008 Third Office Action dated Apr. 27, 2013.
CN 200880125528.4 filed Nov. 25, 2008 First Office Action dated Jun. 5, 2012.
CN 200880125528.4 filed Nov. 25, 2008 Second Office Action dated Mar. 6, 2013.
CN 200880125528.4 filed Nov. 25, 2008 Third Office Action dated Jul. 1, 2013.
CN 200980123021.X filed Dec. 17, 2010 First Office Action dated Nov. 19, 2012.
CN 200980123021.X filed Dec. 17, 2010 Second Office Action dated Aug. 13, 2011.
CN 200980123021.X filed Dec. 17, 2010 Third Office Action dated Apr. 22, 2014.
CN 200980144663.8 filed May 9, 2011 Decision of Re-Examination dated Feb. 21, 2017.
CN 200980144663.8 filed May 9, 2011 Fifth Office Action dated May 26, 2015.
CN 200980144663.8 filed May 9, 2011 First Office Action dated Dec. 5, 2012.
CN 200980144663.8 filed May 9, 2011 Fourth Office Action dated Nov. 15, 2014.
CN 200980144663.8 filed May 9, 2011 Notice of Reexamination dated Aug. 5, 2016.
CN 200980144663.8 filed May 9, 2011 Second Office Action dated Aug. 22, 2013.
CN 200980144663.8 filed May 9, 2011 Third Office Action dated May 4, 2014.
CN 201080035659.0 filed Feb. 10, 2012 First Office Action dated Jan. 26, 2014.
CN 201080035659.0 filed Feb. 10, 2012 Second Office Action dated Oct. 9, 2014.
CN 201080035659.0 filed Feb. 10, 2012 Third Office Action dated Mar. 19, 2015.
CN 201080053838.7 filed May 28, 2012 First Office Action dated Jan. 6, 2014.
CN 201080053838.7 filed May 28, 2012 Fourth Office Action dated Jun. 2, 2015.
CN 201080053838.7 filed May 28, 2012 Second Office Action dated Jun. 17, 2014.
CN 201080053838.7 filed May 28, 2012 Third Office Action dated Dec. 4, 2014.
CN 201180016462.7 filed Sep. 27, 2012 First Office Action dated Mar. 21, 2014.
CN 201180016462.7 filed Sep. 27, 2012 Second Office Action dated Dec. 9, 2014.
CN 201180016462.7 filed Sep. 27, 2012 Third Office Action dated Jun. 10, 2015.
CN 201180037065.8 filed Jan. 28, 2013 First Office Action dated Sep. 28, 2014.
CN 201180037065.8 filed Jan. 28, 2013 Fourth Office Action dated May 5, 2016.
CN 201180037065.8 filed Jan. 28, 2013 Notice of Grant dated Aug. 30, 2016.
CN 201180037065.8 filed Jan. 28, 2013 Second Office Action dated Jun. 2, 2015.
CN 201180037065.8 filed Jan. 28, 2013 Third Office Action dated Nov. 24, 2015.
CN 201180037068.1 filed Jan. 28, 2013 First Office Action dated Apr. 20, 2015.
CN 201180037068.1 filed Jan. 28, 2013 First Office Action dated Sep. 9, 2014.
CN 201180037068.1 filed Jan. 28, 2013 Third Office Action dated Oct. 19, 2015.
CN 201180040151.4 filed Feb. 19, 2013 First Office Action dated Oct. 28, 2014.
CN 201180040151.4 filed Feb. 19, 2013 Office Action dated Dec. 10, 2015.
CN 201180040151.4 filed Feb. 19, 2013 Second Office Action dated Jun. 19, 2015.
CN 201180043512.0 filed Mar. 8, 2013 First Office Action dated Jul. 31, 2014.
CN 201180043512.0 filed Mar. 8, 2013 Second Office Action dated Apr. 14, 2015.
CN 201180052587.5 filed Apr. 28, 2013 First Office Action dated Jan. 26, 2015.
Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.
Liu , Ji-Bin et al, Catheter-Based Intraluminal Sonography, J Ultrasound Med, pp. 145-160, vol. 23, 2004.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No. 5, Sep.-Oct. 1999.
Lum Phillip, A New Formula-Based Measurement Guide for Optimal Positioning of Central Venous Catheters, JAVA, vol. 9, No. 2, pp. 80-85, 2004.
Lynch, Re et al, A Procedure for Placing Pediatric Femoral Venous Catheter Tips near the Right Atrium, Pediatr Emerg Care, pp. 130-132, vol. 18 No. 2, Apr. 2002.
Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.
Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, CHEST, 2003.
Markovich, Mary B., Central Venous Catheter Tip Placement: Determination of Posterior Malposition—A Case Study, JAVA, vol. 11, No. 2, pp. 85-89, 2006.
Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.
McDonnall, "Intra-Atrial Electrocardiography (ECG) for Catheter Placement." Literature review prepared for Bard Access Systems, Oct. 2007.
McGee et al., "Accurate Placement of Central Venous Catheters: A Prospective, Randomize, Multicenter Trail." Critical Care Medicine, vol. 21 No. 8, Aug. 1993.
MedGraphics, CardioPerfect® Resting/Stress ECG System, 3 pages, 2001.

(56) References Cited

OTHER PUBLICATIONS

Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.
Michenfelder, John et al, Air Embolism During Neurosurgery. A New Method of Treatment, Anesthesia and Analgesia. Current Researches, pp. 390-395, vol. 45, No. 4, Jul.-Aug. 1966.
MICROBIRD™ Miniaturized DC Magnetic Sensors for Intra-body Navigation and Localization, Specifications, 2005.
MICRONIX CathRite™ Cardiac Access Device Brochure. Jun. 2004.
Micronix Pty Ltd "CathRite" Guiding Styled Core Manufacturing, Jun. 15, 2006.
Moureau, Nancy L. et al., "Electrocardiogram (EKG) Guided Peripherally Inserted Central Catheter Placement and Tip Position: Results of a Trial to Replace Radiological Confirmation," Journal of the Association for Vascular Access, pp. 8-14, vol. 15, No. 1, 2010.
Murthy, Vrudhula et al, Analysis of Power Spectral Densities of Electrocardiograms, Mathematical Biosciences, pp. 41-51, vol. 12 No. 1-2, Oct. 1971.
MX/a/2012/013672 filed Nov. 23, 2012 First Office Action dated Aug. 10, 2015.
MX/a/2012/013858 filed Nov. 28, 2012 First Office Action dated Sep. 26, 2014.
MX/a/2012/013858 filed Nov. 28, 2012 Second Office Action dated Jun. 10, 2015.
MX/a/2013/001317 filed Jan. 31, 2013 First Office Action dated Nov. 26, 2015.
MX/a/2015/004864 filed Apr. 16, 2015 Office Action dated Apr. 24, 2018.
MX/a/2015/004864 filed Apr. 16, 2015 Office Action dated Dec. 18, 2017.
Nadroo, AM et al, Changes in Upper Extremity Position Cause Migration of Peripherally Inserted Central Catheters in Neonates, Pediatrics, pp. 131-136, vol. 110, Jul. 2002.
Nakatani, K et al, Accurate Placement of Central Venous Catheters—ECG-guided method vs Patient Height Method, MASUI, pp. 34-38, vol. 51 No. 1, Jan. 2002.
Nazarian, GK et al, Changes in Tunneled Catheter Tip Position when a patient is Upright, J Vasc Interv Radiol, pp. 437-441, vol. 8 No. 3, May-Jun. 1997.
NEUROMETER® CPT, Clinical Applications. Neurotron , Inc. website: www.neurotron.com/CLINAPS.html, last accessed Oct. 23, 2006.
NEUROMETER® CPT, Frequently Asked Questions. Neurotron , Inc. website: www.neurotron.com/CPTFAQ/html, last accessed Oct. 23, 2006.
NEUROMETER® CPT, Products Page. Neurotron , Inc. website: www.neurotron.com/products.html, last accessed Oct. 23, 2006.
NEUROMETER® Electrodiagnostic Neuroselective Sensory Nerve Evaluation: Charts, Tables, Documents & Downloads. Neurotron , Inc. website: www.neurotron.com/downloads.html, last accessed Oct. 23, 2006.
NOT Resource Center. Magnetic Permeability. Oct. 18, 2014. Last accessed Mar. 23, 2018. <URL:https://web.archive.org/web/20141018213902/https://www.nde-ed.org/EducationResources/CommunityCollege/Materials/Physical_Chemical/Permeability.htm>.
Odd, De et al, Does Radio-opaque Contrast Improve Radiographic localisation of Percutaneous Central Venous Lines?, Arch Dis Child Fetal Neonatal Ed, pp. 41-43, vol. 89 No. 1, Jan. 2004.
Palesty, JA et al, Routine Chest Radiographs Following Central Venous Recatherization over a Wire are not Justified, Am J Surg, pp. 618-621, vol. 176 No. 6, Dec. 1998.
Paliotti, Roberta P. et al, Intravascular Doppler Technique for Monitoring Renal Venous Blood Flow in Man, J Nephrol, pp. 57-62, 2003.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Pawlik, et al., "Central Venous Catheter Placement: Comparison of the Intravascular Guidewire and the Fluid Column Electrocardiograms." European Journal of Anaesthesiology, vol. 41, pp. 594-599, 2004.
PCT/US13/62409 filed Sep. 27, 2013 International Search Report and Written Opinion dated Feb. 24, 2014.
PCT/US2006/033079 filed Aug. 24, 2006 International Preliminary Report on Patentability dated Feb. 26, 2008.
PCT/US2006/033079 filed Aug. 24, 2006 Search Report dated Dec. 19, 2006.
PCT/US2006/033079 filed Aug. 24, 2006 Written Opinion dated Dec. 19, 2006.
PCT/US2008/060502 filed Apr. 16, 2008 International Search Report and Written Opinion dated Oct. 16, 2008.
PCT/US2008/084751 filed Nov. 25, 2008 International Preliminary Report on Patentability dated Jun. 1, 2010.
PCT/US2008/084751 filed Nov. 25, 2008 Search Report dated May 20, 2009.
PCT/US2008/084751 filed Nov. 25, 2008 Written Opinion dated May 20, 2009.
PCT/US2009/033116 filed Feb. 4, 2009 International Preliminary Report on Patentability dated Aug. 10, 2010.
PCT/US2009/033116 filed Feb. 4, 2009 Search Report dated Mar. 13, 2009.
PCT/US2009/033116 filed Feb. 4, 2009 Written Opinion dated Mar. 13, 2009.
PCT/US2009/041051 filed Apr. 17, 2009 International Preliminary Report on Patentability dated Apr. 8, 2014.
PCT/US2009/041051 filed Apr. 17, 2009 Search Report dated Jul. 28, 2009.
PCT/US2009/041051 filed Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.
PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/038391 filed May 27, 2011 International Preliminary Report on Patentability and Written Opinion dated Dec. 4, 2012.
PCT/US2011/038391 filed May 27, 2011 International Search Report dated Sep. 21, 2011.

(56) References Cited

OTHER PUBLICATIONS

PCT/US2011/038415 filed May 27, 2011 International Preliminary Report on Patentability dated Dec. 13, 2012.
PCT/US2011/038415 filed May 27, 2011 International Search Report dated Sep. 28, 2011.
PCT/US2011/038415 filed May 27, 2011 Written Opinion dated Sep. 28, 2011.
PCT/US2011/047127 filed Aug. 9, 2011 International Preliminary Report on Patentability dated Apr. 18, 2013.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/048403 filed Aug. 19, 2011 International Preliminary Report on Patentability dated Jul. 30, 2013.
PCT/US2011/048403 filed Aug. 19, 2011 International Search Report dated Dec. 15, 2011.
PCT/US2011/048403 filed Aug. 19, 2011 Written Opinion dated Dec. 15, 2011.
PCT/US2011/052793 filed Sep. 22, 2011 International Preliminary Report on Patentability dated Apr. 4, 2013.
PCT/US2011/052793 filed Sep. 22, 2011 International Search Report dated Jan. 6, 2012.
PCT/US2011/052793 filed Sep. 22, 2011 Written Opinion dated Jan. 6, 2012.
PCT/US2011/058138 filed Oct. 27, 2011 International Preliminary Report on Patentability dated May 10, 2013.
PCT/US2011/058138 filed Oct. 27, 2011 International Search Report dated Feb. 7, 2012.
PCT/US2011/058138 filed Oct. 27, 2011 Written Opinion dated Feb. 7, 2012.
PCT/US2011/067268 filed Dec. 23, 2011 International Preliminary Report on Patentability dated Jul. 4, 2013.
PCT/US2011/067268 filed Dec. 23, 2011 International Search Report and Written Opinion dated Apr. 27, 2012.
PCT/US2012/045814 filed Jul. 6, 2012 International Search Report and Written Opinion dated Oct. 1, 2012.
PCT/US2013/065121 filed Oct. 15, 2013 International Search Report and Written Opinion dated Jan. 16, 2014.
PCT/US2014/022019 filed Mar. 7, 2014 International Search Report and Written Opinion dated Jun. 11, 2014.
PCT/US2015/014795 filed Feb. 6, 2015 International Search Report and Written Opinion dated May 14, 2015.
PCT/US2016/039356 filed Jun. 24, 2016 International Search Report and Written Opinion dated Sep. 16, 2016.
PCT/US2017/066503 filed Dec. 14, 2017 International Search Report and Written Opinion dated Feb. 20, 2018.
Pennington, C.R., Right Atrial Thrombus: a Complication of Total Parenteral Nutrition, British Medical Journal, pp. 446-447, vol. 295, Aug. 15, 1987.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
Pittiruti, et al, "The intracavitary ECG method for positioning the tip of central venous catheters: results of an Italian multicenter study," J Vasc Access, pp. 1-9, Nov. 21, 2011.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Pittiruti, et al. "The electrocardiographic method for positioning the tip of central venous catheters" JAVA, pp. 1-12, Feb. 12, 2011.
Gebhard, et al., "The accuracy of Electrocardiogram-Controlled Central Line Placement." The International Anesthesia Research Society, vol. 104, No. 1 Jan. 2007.
Gjendemsjo, Anders, et al., Energy and Power, The Connexions Project, Version 1.2, Feb. 20, 2004.
Gladwin, MT et al, Cannulation of the Internal Jugular Vein: is postpocedural chest radiography always necessary?, Crit Care Med, 33 pages, Oct. 2000.
Gonzales, et al. "Peripherally Inserted Central Catheter Placement in Swine Using Magnet Detection." Journal of Intravenous Nursing, vol. 22, No. 3, May/Jun. 1999.
Greenall, M.J. et al, Cardiac Tamponade and Central Venous Catheters, British Medical Journal, pp. 595-597, Jun. 14, 1975.
Guillory, "Basic Principles of Technologies for Catheter Localization." C.R. Bard internal paper, Oct. 20, 2004.
Guth, AA, Routine Chest X-rays after Insertion of Implantable Long-Term Venous Catheters: Necessary or Not?, Am Surg, pp. 26-29, vol. 67 No. 1, Jan. 2001 (Abstract only).
Hamza, N. et al. "Interference reduction in ECG signal acquisition: Ground electrode removal." 2013 International Conference on Computer Medical Applications (ICCMA), Jan. 2013.
Hill, Bradley et al, Abstract of article discussing Vasallova VPS as guide for placement of PICCs. 2009.
Hill, Bradley, Identifying the Caval-Atrial Junction Using Smart-Catheter Technology presentation, 22nd Annual Scientific Meeting of the AVA in Savannah, Georgia, Sep. 13, 2008.
Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.
Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.
Honeywell, "1, 2 and 3 Axis Magnetic Sensors HMC1051/HMC1052L/HMC1053" dated Jan. 2010.
Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.
Jeon, Yunseok et al., "Transesophageal Echocardiographic Evaluation of ECG-guided Central Venous Catheter Placement," Canadian Journal of Anesthesia, vol. 53, No. 10, Oct. 1, 2006, pp. 978-983.
Joosting, Jean-Pierre, "Dual-interface RFID-compatible EEPROM enables remote access to electronic device parameters," EE Times, Mar. 8, 2010.
JP 2008-528151 filed Aug 24, 2006 Notice of Grant dated May 6, 2012.
JP 2010-504220 filed Sep. 3, 2009 Final Office Action dated Apr. 18, 2013.
JP 2010-504220 filed Sep. 3, 2009 Office Action dated Apr. 1, 2014.
JP 2010-504220 filed Sep. 3, 2009 Office Action dated Apr. 18, 2013.
JP 2010-504220 filed Sep. 3, 2009 Office Action dated May 21, 2012.
JP 2010-535117 filed May 26, 2011 First Office Action dated Aug. 5, 2013.
JP 2012-515222 filed Dec. 9, 2011 Office Action dated Feb. 23, 2015.
JP 2012-515222 filed Dec. 9, 2011 Office Action dated Mar. 24, 2014.
JP 2012-552060 filed Aug. 1, 2012 Office Action dated Nov. 12, 2014.
JP 2012-552060 filed Aug. 1, 2012 Second Office Action dated Nov. 6, 2015.
JP 2013-512046 filed Nov. 26, 2012 First Office Action dated Mar. 23, 2015.
JP 2013-512046 filed Nov. 26, 2012 Office Action dated Dec. 8, 2015.
JP 2013-512046 filed Nov. 26, 2012 Office Action dated May 16, 2016.
JP 2013-512051 filed Nov. 26, 2012 First Office Action dated Mar. 23, 2015.
JP 2013-524999 filed Jan. 22, 2013 First Office Action dated Jun. 1, 2015.

(56) References Cited

OTHER PUBLICATIONS

JP 2013-530322 filed Mar. 18, 2013, Office Action dated Jul. 6, 2018.
JP 2013-530322 filed Mar. 18, 2013, Office Action dated Mar. 2, 2017.
JP 2013-530322 filed Mar. 18, 2013, Office Action dated Nov. 6, 2017.
JP 2014-519081 filed Dec. 27, 2013 First Office Action dated Apr. 26, 2016.
JP 2015-534770 filed Mar. 26, 2015 Office Action dated Feb. 21, 2018.
JP 2015-534770 filed Mar. 26, 2015 Office Action dated Jun. 12, 2017.
JP2013-530322 filed Mar. 18, 2013, Office Action dated May 2, 2016.
JP2013-530322 filed Mar. 18, 2013, First Office Action dated Jul. 31, 2015.
Kim, Ko et al, Positioning Internal Jugular Venous Catheters using the Right Third Intercostal Space in Children, Acta Anaesthesiol Scand, pp. 1284-1286, vol. 47 No. 10, Nov. 2003.
Kjelstrup Tet al, Positioning of Central Venous Catheters using ECG, Tidssk Nor Laegeforen, pp. 599-601, vol. 111 No. 5, Feb. 1999 (Abstract only).
Kofler, Julia, et al., Epinephrine application via an endotracheal airway and via the Combitube in esophageal position, Critical Care Medicine: May 2000, vol. 28: Issue 5, pp. 1445-1449.
Konings, MK, et al., Development of an intravascular impedance catheter for detection of fatty lesions in arteries, IEEE Trans Med Imaging Aug. 1997; 16(4):439-46.
Kowalski, CM et al, Migration of Central Venous Catheters: Implications for Initial Catheter Tip Positioning, J Vasc Interv Radiol, pp. 443-447, vol. 8 No. 3, May-Jun. 1997.
KR 10-2012-7000866 filed Jan. 11, 2012 First Office Action dated Jun. 16, 2016.
KR 10-2012-7000866 filed Jan. 11, 2012 Second Office Action dated Nov. 3, 2016.
KR 10-2013-7006933 filed Mar. 19, 2013 Office Action dated Aug. 7, 2017.
KR 10-2014-7002789 filed Feb. 3, 2014 Office Action dated Feb. 22, 2019.
KR 10-2014-7002789 filed Feb. 3, 2014 Office Action dated Jun. 21, 2018.
Leowenthal, MR et al, The Peripherally Inserted Central Catheter (PICC): A Prospective Study of its Natural History after Fossa Insertion, Anaesth Intensive Care, pp. 21-24; vol. 30 No. 1, Feb. 2002.
"ASCENSION to Launch New 3D Guidance™ Tracker at TCT 2006." Press Releases from Ascension website: www.ascension-tech.com/news/press_101106.php, last accessed Dec. 1, 2006.
Acuson—The Value of Vision, AcuNav Diagnostic Ultrasound Catheter, 2000.
Advertising flyer for Gavecelt—The Italian Group for Long Term Venous Access Devices, for program on International Meeting on PICC's, Midline Catheters and Long Term Venous Access Devices in Catholic University, Rome, Italy on Dec. 3, 4, 5, 2008.
Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.
Allan, P.L. et al, Role of Ultrsound in the Assessment of Chronic Venous Insufficiency, Ultrasound Quarterly, vol. 17, No. 1, pp. 3-10, 2001.
Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.
Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.
Arai, J et al, Detection of Peripherally Inserted Central Catheter Occlusion by in-line Pressure Monitoring, Paediatr Anaesth, pp. 621-624, vol. 12 No. 7, Sep. 2002.
Arrow International, Inc., The Arrow-Johans Raecg Adapter-Making Proper Central Venous Catheter Placement More Reliable (Modle No. EG-04900), Technical Report 1987, USA.
Aslamy, et al. "MRI of Central Venous Anatomy: Implications for Central Venous Catheter Insertion." American College of Chest Physicians, Jun. 8, 2009.
AU 2006283022 filed Aug. 24, 2006 Office Action dated Dec. 22, 2010.
AU 2008329807 exam requested Aug. 13, 2012 Examination Report No. 1 dated Feb. 15, 2013.
AU 2008329807 exam requested Aug. 13, 2012 Notice of Acceptance dated Feb. 14, 2014.
AU 2010300677 filed Mar. 12, 2012 First Examination Report dated Mar. 9, 2014.
AU 2011289513 filed Jan. 21, 2013 Examiner's Report dated Jul. 5, 2013.
AU 2012202293 filed Apr. 19, 2012 Examination Report No. 1 dated Apr. 24, 2013.
AU 2012278809 filed Nov. 12, 2013 Notice of Acceptance dated Sep. 13, 2016.
AU 2013201648 filed Mar. 19, 2013 Examiner's Report dated Mar. 5, 2014.
AU 2013201648 filed Mar. 19, 2013 Examiner's Report dated Oct. 14, 2013.
AU 2013202824 filed Apr. 6, 2013 First Examiner's Report dated Mar. 10, 2014.
AU 2013204243 filed Apr. 12, 2013 Examiner's Report dated Jun. 5, 2013.
AURORA® System Technical Specifications, Oct. 2003.
AZoMaterials. Nickel-Based Super Alloy Inconel 625—Properties and Applications by United Performance Alloys. Oct. 27, 2015. Last accessed Mar. 23, 2018. <URL:https://web.archive.org/web/20151027202821/https://www.azom.com/article.aspx?ArticleID=4461>.
B. Braun Website, "The Optimal Position of the Central Venous Catheter." http://www.cvcpartner.com/index.cfm18F1BDEA1310466194960A39F4E90968 (2009).
B. Braun, Certofix Central Venous Catheter for Placement Using the Seldinger Technique with Simultaneous ECG Lead Option, Feb. 2010.
Bailey, SH et al, Is Immediate Chest Radiograph Necessary after Central Venous Catheter Placement in a Surgical Intensive Care Unit?, Am J Surg, pp. 517-522, vol. 180 No. 6, Dec. 2000.
Bankier, Alexander A., Azygos Arch Cannulation by Central Venous Catheters: Radiographic Detection of Malposition and Subsequent Complications, Journal of Thoracic Imaging 12:64-69 (1997).
Barber, JM et al, A Nurse led Peripherally Inserted Central Catheter Line Insertion Service is Effective with Radiological Support, Clin Radiol, pp. 352-354, vol. 57 No. 5, May 2002.
Bard Access Systems, Sherlock Tip Location System, 5 pages, 2006.
Bard Access Systems, Site Rite Vascular Acess Ultrasound System, 4 pages, 2005.
Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.
Benzadon, M. N. et al: "Comparison of the Amplitude of the P-Wave from Intracardiac Electrocardiogram Obtained by Means of a Central Venous Catheter Filled With Saline Solution to That Obtained via Esophageal Electrocardiogram", American Journal of Cardiology, Cahners Publishing Co., Newton, MA, US, vol. 98, No. 7, Oct. 1, 2006 (Oct. 1, 2006), pp. 978-981.
BioAdvance Lumen Vu, Greenhouse Fund Feb. 2004 Recipient, www.bioadvance.com <http://www.bioadvance.com>, 2005.

(56) References Cited

OTHER PUBLICATIONS

Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.
Buehrle, Douglas, PICC Placement in Humans using Electromagnetic Detection, <http://www.corpakmedsystems.com/supplement_material/supplementpages/navigator/navarticle.html>, 2008.
C.R. Bard, CathTrack™ Catheter Location System at www.bardaccess.com <http://www.bardaccess.com>, last accessed Apr. 28, 2011.
C.R. Bard, Inc., Bard Electrophysiology Product Catalogue, Bard Catheters, pp. 74-75 (2002), USA.
CA 2,619,909 filed Aug. 24, 2006 Examiner's Report dated Oct. 26, 2012.
CA 2,721,715 filed Apr. 17, 2009 Examiner's Report dated Aug. 18, 2015.
CA 2,721,715 filed Apr. 17, 2009 Examiner's Report dated Oct. 25, 2016.
CA 2800810 filed Nov. 26, 2012 Office Action dated Mar. 13, 2018.
CA 2800810 filed Nov. 26, 2012 Office Action dated Mar. 30, 2017.
CA 2800813 filed Nov. 26, 2012 Office Action dated Mar. 5, 2018.
Cadman, A et al, To Clot or Not to Clot? That is the question in Central Venous Catheters, Clinical Radiology, pp. 349-355, vol. 59 No. 4, Apr. 2004.
Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.
Cardella, John F. et al., Interventional Radiologic Placement of Peripherally Inserted Central Catheters, Journal of Vascular and Interventional Radiology 1993; 4:653-660.
Carlon, R et al, Secondary Migration of a Central Venous Catheter—A Case Report, Minerva Anestesiol, pp. 927-931, vol. 69 No. 12, Dec. 2003.
Caruso, LJ et al, A Better Landmark for Positioning a Central Venous Catheter, J Clinical Monitoring and Computing, pp. 331-334, vol. 17 No. 6, Aug. 2002.
Cavatorta, et al., "Central Venous Catheter Placement in Hemodialysis: Evaluation of Electrocardiography Using a Guidewire." The Journal of Vascular Access, vol. 2, pp. 45-50, 2001.
Chalkiadis, GA et al, Depth of Central Venous Catheter Insertion in Adults: An Audit and Assessment of a Technique to Improve Tip Position, Anaesth Intensive Care, pp. 61-66, vol. 26 No. 1, Feb. 1998.
U.S. Appl. No. 13/469,932, filed May 11, 2012 Final Office Action dated Apr. 7, 2016.
U.S. Appl. No. 13/665,420, filed Oct. 31, 2012 Final Office Action dated Apr. 8, 2016.
U.S. Appl. No. 13/665,420, filed Oct. 31, 2012 Non-Final Office Action dated Jan. 6, 2014.
U.S. Appl. No. 13/665,420, filed Oct. 31, 2012 Non-Final Office Action dated Jul. 9, 2015.
U.S. Appl. No. 13/665,420, filed Oct. 31, 2012 Non-Final Office Action dated Mar. 15, 2017.
U.S. Appl. No. 13/665,420, filed Oct. 31, 2012 Non-Final Office Action dated Oct. 9, 2014.
U.S. Appl. No. 13/665,420, filed Oct. 31, 2012 Notice of Allowance dated Feb. 7, 2018.
U.S. Appl. No. 131/37,806, filed Jan. 9, 2013 Notice of Allowance dated Oct. 31, 2013.
U.S. Appl. No. 13/858,782, filed Apr. 8, 2013 Notice of Allowance dated Oct. 9, 2014.
U.S. Appl. No. 13/887,166, filed May 3, 2013 Advisory Action dated Aug. 27, 2014.
U.S. Appl. No. 13/887,166, filed May 3, 2013 Appeal Decision dated Aug. 17, 2017.
U.S. Appl. No. 13/887,166, filed May 3, 2013 Examiner's Answer dated Jul. 16, 2015.
U.S. Appl. No. 13/887,166, filed May 3, 2013 Final Office Action dated Jun. 23, 2014.
U.S. Appl. No. 13/887,166, filed May 3, 2013 Non-Final Office Action dated Jan. 7, 2014.
U.S. Appl. No. 13/887,166, filed May 3, 2013 Notice of Allowance dated Nov. 6, 2017.
U.S. Appl. No. 13/890,158, filed May 8, 2013 Advisory Action dated Feb. 13, 2018.
U.S. Appl. No. 13/890,158, filed May 8, 2013 Advisory Action dated Jul. 26, 2016.
U.S. Appl. No. 13/890,158, filed May 8, 2013 Final Office Action dated Nov. 21, 2017.
U.S. Appl. No. 13/890,158, filed May 8, 2013 Non-Final Office Action dated Apr. 7, 2017.
U.S. Appl. No. 13/890,158, filed May 8, 2013 Non-Final Office Action dated Aug. 15, 2014.
U.S. Appl. No. 13/890,158, filed May 8, 2013 Non-Final Office Action dated Jul. 9, 2015.
U.S. Appl. No. 13/890,158, filed May 8, 2013 Notice of Allowance dated May 30, 2018.
U.S. Appl. No. 13/969,265, filed Aug. 16, 2013 Non-Final Office Action dated Dec. 19, 2013.
U.S. Appl. No. 13/969,265, filed Aug. 16, 2013 Notice of Allowance dated Jun. 23, 2014.
U.S. Appl. No. 14/040,205, filed Sep. 27, 2013 Advisory Action dated Dec. 15, 2016.
U.S. Appl. No. 14/040,205, filed Sep. 27, 2013 Board Decision dated May 1, 2019.
U.S. Appl. No. 14/040,205, filed Sep. 27, 2013 Examiner's Answer dated Jul. 20, 2017.
U.S. Appl. No. 14/040,205, filed Sep. 27, 2013 Final Office Action dated Oct. 19, 2016.
U.S. Appl. No. 14/040,205, filed Sep. 27, 2013 Non-Final Office Action dated Mar. 10, 2016.
U.S. Appl. No. 14/040,205, filed Sep. 27, 2013 Notice of Allowance dated Aug. 21, 2019.
U.S. Appl. No. 14/054,700, filed Oct. 15, 2013 Advisory Action dated Dec. 15, 2016.
U.S. Appl. No. 14/054,700, filed Oct. 15, 2013 Board Decision dated May 1, 2019.
U.S. Appl. No. 14/054,700, filed Oct. 15, 2013 Examiner's Answer dated Jul. 3, 2017.
U.S. Appl. No. 14/054,700, filed Oct. 15, 2013 Final Office Action dated Oct. 19, 2016.
U.S. Appl. No. 14/054,700, filed Oct. 15, 2013 Notice of Allowance dated Jun. 6, 2019.
U.S. Appl. No. 14/141,046, filed Dec. 26, 2013 Advisory Action dated Aug. 4, 2016.
U.S. Appl. No. 14/141,046, filed Dec. 26, 2013 Examiner's Answer dated Oct. 15, 2018.
U.S. Appl. No. 14/141,046, filed Dec. 26, 2013 Final Office Action dated Dec. 11, 2017.
U.S. Appl. No. 14/141,046, filed Dec. 26, 2013 Final Office Action dated May 11, 2016.
U.S. Appl. No. 14/141,046, filed Dec. 26, 2013 Non-Final Office Action dated Apr. 7, 2017.
U.S. Appl. No. 14/141,046, filed Dec. 26, 2013 Non-Final Office Action dated Feb. 11, 2015.
U.S. Appl. No. 14/141,046, filed Dec. 26, 2013 Non-Final Office Action dated Jun. 20, 2014.
U.S. Appl. No. 14/141,046, filed Dec. 26, 2013 Non-Final Office Action dated Nov. 5, 2015.
U.S. Appl. No. 14/201,300, filed Mar. 7, 2014 Advisory Action dated Jul. 18, 2016.
U.S. Appl. No. 14/201,300, filed Mar. 7, 2014 Advisory Action dated Mar. 2, 2017.
U.S. Appl. No. 14/201,300, filed Mar. 7, 2014 Board Decision dated Apr. 12, 2019.
U.S. Appl. No. 14/201,300, filed Mar. 7, 2014 Board Decision dated Jul. 23, 2019.
U.S. Appl. No. 14/201,300, filed Mar. 7, 2014 Examiner's Answer dated Apr. 19, 2018.
U.S. Appl. No. 14/201,300, filed Mar. 7, 2014 Final Office Action dated Dec. 19, 2016.

(56) References Cited

OTHER PUBLICATIONS

U.S. Appl. No. 14/201,300, filed Mar. 7, 2014 Final Office Action dated Jul. 10, 2017.
U.S. Appl. No. 12/893,916, filed Sep. 29, 2010 Advisory Action dated Jun. 2, 2016.
U.S. Appl. No. 12/893,916, filed Sep. 29, 2010 Final Office Action dated Jan. 15, 2015.
U.S. Appl. No. 12/893,916, filed Sep. 29, 2010 Final Office Action dated Jun. 18, 2014.
U.S. Appl. No. 12/893,916, filed Sep. 29, 2010 Final Office Action dated Mar. 25, 2016.
U.S. Appl. No. 12/893,916, filed Sep. 29, 2010 Non-Final Office Action dated Aug. 31, 2016.
U.S. Appl. No. 12/893,916, filed Sep. 29, 2010 Non-Final Office Action dated Dec. 24, 2013.
U.S. Appl. No. 12/893,916, filed Sep. 29, 2010 Non-Final Office Action dated Sep. 10, 2015.
U.S. Appl. No. 12/893,916, filed Sep. 29, 2010 Non-Final Office Action dated Sep. 25, 2014.
U.S. Appl. No. 12/900,750, filed Oct. 8, 2010 Non-Final Office Action dated Jun. 3, 2013.
U.S. Appl. No. 13/019,939, filed Feb. 2, 2011 Final Office Action dated Apr. 2, 2014.
U.S. Appl. No. 13/019,939, filed Feb. 2, 2011 Non-Final Office Action dated Feb. 9, 2015.
U.S. Appl. No. 13/019,939, filed Feb. 2, 2011 Non-Final Office Action dated Oct. 11, 2013.
U.S. Appl. No. 13/118,033, filed May 27, 2011 Final Office Action dated Apr. 1, 2016.
U.S. Appl. No. 13/118,033, filed May 27, 2011 Non-Final Office Action dated Aug. 1, 2013.
U.S. Appl. No. 13/118,033, filed May 27, 2011 Non-Final Office Action dated Feb. 3, 2015.
U.S. Appl. No. 13/118,033, filed May 27, 2011 Non-Final Office Action dated Jul. 8, 2015.
U.S. Appl. No. 13/118,033, filed May 27, 2011 Non-Final Office Action dated May 22, 2014.
U.S. Appl. No. 13/118,033, filed May 27, 2011 Notice of Allowance dated Sep. 2, 2016.
U.S. Appl. No. 13/118,138, filed May 27, 2011 Final Office Action dated Apr. 1, 2016.
U.S. Appl. No. 13/118,138, filed May 27, 2011 Final Office Action dated Apr. 3, 2013.
U.S. Appl. No. 13/118,138, filed May 27, 2011 Non-Final Office Action dated Jul. 15, 2015.
U.S. Appl. No. 13/118,138, filed May 27, 2011 Non-Final Office Action dated Oct. 3, 2012.
U.S. Appl. No. 13/118,138, filed May 27, 2011 Non-Final Office Action dated Oct. 9, 2014.
U.S. Appl. No. 13/213,622, filed Aug. 19, 2011 Final Office Action dated Feb. 19, 2013.
U.S. Appl. No. 13/213,622, filed Aug. 19, 2011 Non-Final Office Action dated Jul. 31, 2012.
U.S. Appl. No. 13/213,622, filed Aug. 19, 2011 Non-Final Office Action dated May 22, 2014.
U.S. Appl. No. 13/240,171, filed Sep. 22, 2011 Advisory Action dated Aug. 18, 2015.
U.S. Appl. No. 13/240,171, filed Sep. 22, 2011 Advisory Action dated Jul. 22, 2016.
U.S. Appl. No. 13/240,171, filed Sep. 22, 2011 Final Office Action dated Jun. 10, 2015.
U.S. Appl. No. 13/240,171, filed Sep. 22, 2011 Final Office Action dated May 6, 2016.
U.S. Appl. No. 13/240,171, filed Sep. 22, 2011 Non-Final Office Action dated Dec. 1, 2015.
U.S. Appl. No. 13/240,171, filed Sep. 22, 2011 Non-Final Office Action dated Dec. 26, 2014.
U.S. Appl. No. 13/283,395, filed Oct. 27, 2011 Advisory Action dated Jan. 28, 2014.
U.S. Appl. No. 13/283,395, filed Oct. 27, 2011 Final Office Action dated Nov. 14, 2013.
U.S. Appl. No. 13/283,395, filed Oct. 27, 2011 Non-Final Office Action dated Apr. 23, 2013.
U.S. Appl. No. 13/336,919, filed Dec. 23, 2011 Advisory Action dated May 23, 2013.
U.S. Appl. No. 13/336,919, filed Dec. 23, 2011 Final Office Action dated Dec. 19, 2014.
U.S. Appl. No. 13/336,919, filed Dec. 23, 2011 Final Office Action dated Mar. 1, 2013.
U.S. Appl. No. 13/336,919, filed Dec. 23, 2011 Non-Final Office Action dated Dec. 27, 2013.
U.S. Appl. No. 13/336,919, filed Dec. 23, 2011 Non-Final Office Action dated Jul. 9, 2015.
U.S. Appl. No. 13/336,919, filed Dec. 23, 2011 Non-Final Office Action dated Oct. 16, 2012.
U.S. Appl. No. 13/336,919, filed Dec. 23, 2011 Notice of Allowance dated Jul. 26, 2016.
U.S. Appl. No. 13/337,987, filed Dec. 27, 2011 Examiner's Answer dated Jul. 2, 2014.
U.S. Appl. No. 13/337,987, filed Dec. 27, 2011 Final Office Action dated Sep. 19, 2013.
U.S. Appl. No. 13/337,987, filed Dec. 27, 2011 Non-Final Office Action dated Mar. 15, 2013.
U.S. Appl. No. 13/469,932, filed May 11, 2012 Advisory Action dated Jun. 27, 2016.
U.S. Appl. No. 13/469,932, filed May 11, 2012 Non-Final Office Action dated Jan. 3, 2014.
U.S. Appl. No. 13/469,932, filed May 11, 2012 Non-Final Office Action dated Jul. 31, 2014.
U.S. Appl. No. 13/469,932, filed May 11, 2012 Non-Final Office Action dated Sep. 4, 2015.
U.S. Appl. No. 13/469,932, filed May 11, 2012 Notice of Allowance dated Jan. 31, 2017.
Polos, PG et al, Tips for Monitoring the Position of a Central Venous Catheter—How Placement can go awry—even when the anatomy is normal, J Crit Illn, pp. 660-674, vol. 8 No. 6, Jun. 1993 (Abstract only).
Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.
Popp, M. B. et al., Accuracy of implanted port placement with the use of the electromagnetic CathTrack® catheter locator system, The Journal of Vascular Access 2005; 6: 9-12.
Randolph AG et al, Ultrasound guidance for placement of central venous catheters: a meta-analysis of the literature, Critcal Care Medicine, pp. 2053-2058, vol. 24, Dec. 1996.
Reece, A et al, Posititioning Long Lines: Contrast Versus Plain Radiography, Arch Dis Child Fetal Neonatal Ed, pp. 129-130, vol. 84 No. 2, Mar. 2001.
Reynolds, N et al, Assessment of Distal Tip Position of Long Term Central Venous Feeding Catheters using Transesophageal Echocardiology, JPEN J Parenter Enteral Nutr, pp. 39-41, vol. 25 No. 1, Jan.-Feb. 2001.
RU 2011150917 filed Dec. 15, 2011 First Office Action dated Apr. 24, 2014.
RU 2011150917 filed Dec. 15, 2011 Second Office Action dated Aug. 28, 2014.
RU 2013158008 filed Dec. 26, 2013 First Office Action dated May 27, 2016.
RU 2015110633 filed Mar. 26, 2015 Office Action dated Oct. 25, 2018.
RU 2015111669 filed Apr. 1, 2015 Office Action dated Jan. 25, 2018.
RU 2015111669 filed Apr. 1, 2015 Office Action dated May 18, 2018.
RU 2015111669 filed Apr. 1, 2015 Office Action dated Sep. 5, 2017.
Ruschulte, Heiner et al, Prevention of Central Venous Catheter related infections with chlorhex idine gluconate impregnated wound dressings: A randomized controlled trial, presented as an abstract at

(56) References Cited

OTHER PUBLICATIONS the Annual meeting of the European Society of Anaesthesiologists (ESA) in Madrid, Spain in Jun. 2006, 12 pages, Annals of Hematology, Jul. 14, 2008.
Rutherford, J. S. et al., Depth of Central Venous Catheterization: An Audit of Practice in a Cardiac Surgical Unit, Anaesth Intens Care 1994; 22: 267-271.
Sacolick, et al. "Electromagnetically Tracked Placement of a Peripherally Inserted Central Catheter." SPIE Medical Imaging, 2004 Proceedings.
Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.
Savary, D et al, Intra-atrial Monitoring to Add Insertion of a Central Venous Line in Pre-Hospital Emergency Care Journal Europeen des Urgences, pp. 75-78, vol. 17 No. 2, 2004.
Schafer et al. "Incorrect placement of a vena cava catheter and its prevention by intra-atrial ECG." Anaesthesist. Jan. 1988;37(1):49-51.
Schummer, et al. "Central Venous Catheters—The inability of 'intra-atrial ECG' to prove adequate positioning." British Journal of Anaesthesia, vol. 93, No. 2, pp. 193-198, 2004.
Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—the Inability of "Intra-Atrial ECG" to prove Adequate Positioning, Br J Anaesth, pp. 193-198, vol. 93 No. 2, Aug. 2004.
Schuster, M. et al., The carina as a landmark in central venous catheter placement, British Journal of Anaesthesia 85 (2): 192-4 (2000).
Siela, Debra, Using Chest Radiography in the Intensive Care Unit, Crit Care Nurse Aug. 1, 2002 vol. 22 No. 4, pp. 18-27.
Simon, et al., "Central Venous Catheter Placement in Children: Evaluation of Electrocardiography Using J-Wire." Paediatric Anaesthesia vol. 9, pp. 501-504, 1999.
Smith, Brigham, et al., Intravenous electrocardiographic guidance for placement of peripherally inserted central catheters, Journal of Electrocardiology 43 (2010) 274-278.
Stark, DD et al, Radiographic Assessment of Venous Catheter Position in Children: Value of the Lateral View, Pediatric Radiology, pp. 76-80, vol. 14 No. 2, 1984.
Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.
Starkhammer, H et al, Central Venous Catheter Placement using Electromagnetic Position Sensing: A Clinical Evaluation, Biomed. Instrum Technol, vol. 30 No. 2, pp. 164-170; Mar.-Apr. 1996.
Starr, David S et al, EKG Guided Placement of Subclavian CVP Catheters Using J-Wire, pp. 673-676, Ann. Surg, Dec. 1986.
Stas, M et al, Peroperative Intravasal Electrographic Control of Catheter Tip Position in Access Ports Placed by Venous Cut-Down Technique, EJSO, pp. 316-320, vol. 27, 2001.
STEREOTAXIS Magetic Navigation System with Navigant™ User Interface, 2005 Brochure.
STEREOTAXIS, Expanding the Possibilites of Interventional Medicine: Remote Navigation and Automation, pp. 1-8, Apr. 2011.
Tepa® Health Innovation PC based ECG System Introduction and Technical Specifications, EKG Master USB, 2 pages, Nov. 2003.
Thakor, N. V., et al. "Ground-Free ECG Recording with Two Electrodes." IEEE Transactions on Biomedical Engineering, vol. BME-27, No. 12, Dec. 1980.
The FloWire Doppler Guide Wire located <http://www.volcanocorp.com/products/flowire-doppler-guide-wire.php>, 2011.
TRAXAL Technologies, Tracking Technology website overview: www.traxal.com/rd/rd_classroom_trackingtechnology.htm, last accessed Dec. 1, 2006.
UAB Health Systems, Arrhythmias, retrieved from http://www.health,uab.edu/14564/ on Nov. 15, 2007, 12 pages.
U.S. Appl. No. 11/466,602, filed Aug. 23, 2006 Advisory Action dated Jun. 22, 2009.
U.S. Appl. No. 11/466,602, filed Aug. 23, 2006 Appeal Board Decision dated Sep. 17, 2012.
U.S. Appl. No. 11/466,602, filed Aug. 23, 2006 Final Office Action dated Apr. 8, 2010.
U.S. Appl. No. 11/466,602, filed Aug. 23, 2006 Final Office Action dated Jan. 30, 2009.
U.S. Appl. No. 11/466,602, filed Aug. 23, 2006 Final Office Action dated Oct. 28, 2013.
U.S. Appl. No. 11/466,602, filed Aug. 23, 2006 Non-Final Office Action dated Mar. 28, 2013.
U.S. Appl. No. 11/466,602, filed Aug. 23, 2006 Non-Final Office Action dated Sep. 25, 2009.
U.S. Appl. No. 11/466,602, filed Aug. 23, 2006 Notice of Allowance dated Dec. 3, 2012.
U.S. Appl. No. 11/466,602, filed Aug. 23, 2006 Notice of Allowance dated Mar. 14, 2014.
U.S. Appl. No. 11/552,094, filed Oct. 23, 2006 Notice of Allowability dated Apr. 2, 2010.
U.S. Appl. No. 11/552,094, filed Oct. 23, 2006 Non-Final Office Action dated Apr. 27, 2009.
U.S. Appl. No. 14/996,247, filed Jan. 15, 2016 Non-Final Office Action dated Sep. 1, 2020.
U.S. Appl. No. 15/418,475, filed Jan. 27, 2017 Non-Final Office Action dated Sep. 1, 2020.
U.S. Appl. No. 15/585,051, filed May 2, 2017 Notice of Allowance dated Jul. 31, 2020.
U.S. Appl. No. 15/625,842, filed Jun. 16, 2017 Final Office Action dated Nov. 5, 2020.
U.S. Appl. No. 15/816,932, filed Nov. 17, 2017 Corrected Notice of Allowance dated Nov. 16, 2020.
U.S. Appl. No. 15/816,932, filed Nov. 17, 2017 Notice of Allowance dated Oct. 29, 2020.
U.S. Appl. No. 15/836,741, filed Jan. 8, 2017 Notice of Allowance dated Sep. 10, 2020.
U.S. Appl. No. 15/900,623, filed Feb. 20, 2018 Advisory Action dated Aug. 7, 2020.
U.S. Appl. No. 16/017,695, filed Jun. 25, 2018 Non-Final Office Action dated Jul. 20, 2020.
U.S. Appl. No. 15/418,475, filed Jan. 27, 2017 Notice of Allowance dated Jan. 28, 2021.
U.S. Appl. No. 15/842,685, filed Dec. 14, 2017 Non-Final Office Action dated Jan. 7, 2021.
U.S. Appl. No. 15/900,623, filed Feb. 20, 2018 Notice of Allowance dated Mar. 4, 2021.
U.S. Appl. No. 16/017,695, filed Jun. 25, 2018 Advisory Action dated Feb. 23, 2021.
U.S. Appl. No. 16/164,592, filed Oct. 18, 2018 Non-Final Office Action dated Feb. 19, 2021.
U.S. Appl. No. 16/598,952, filed Oct. 10, 2019 Notice of Allowance dated Dec. 23, 2020.
U.S. Appl. No. 16/598,952, filed Oct. 10, 2019 Supplemental Notice of Allowance dated Feb. 24, 2021.
U.S. Appl. No. 16/598,952, filed Oct. 10, 2019 Supplemental Notice of Allowance dated Jan. 25, 2021.
U.S. Appl. No. 16/598,952, filed Oct. 10, 2019 Supplemental Notice of Allowance dated Jan. 29, 2021.

* cited by examiner

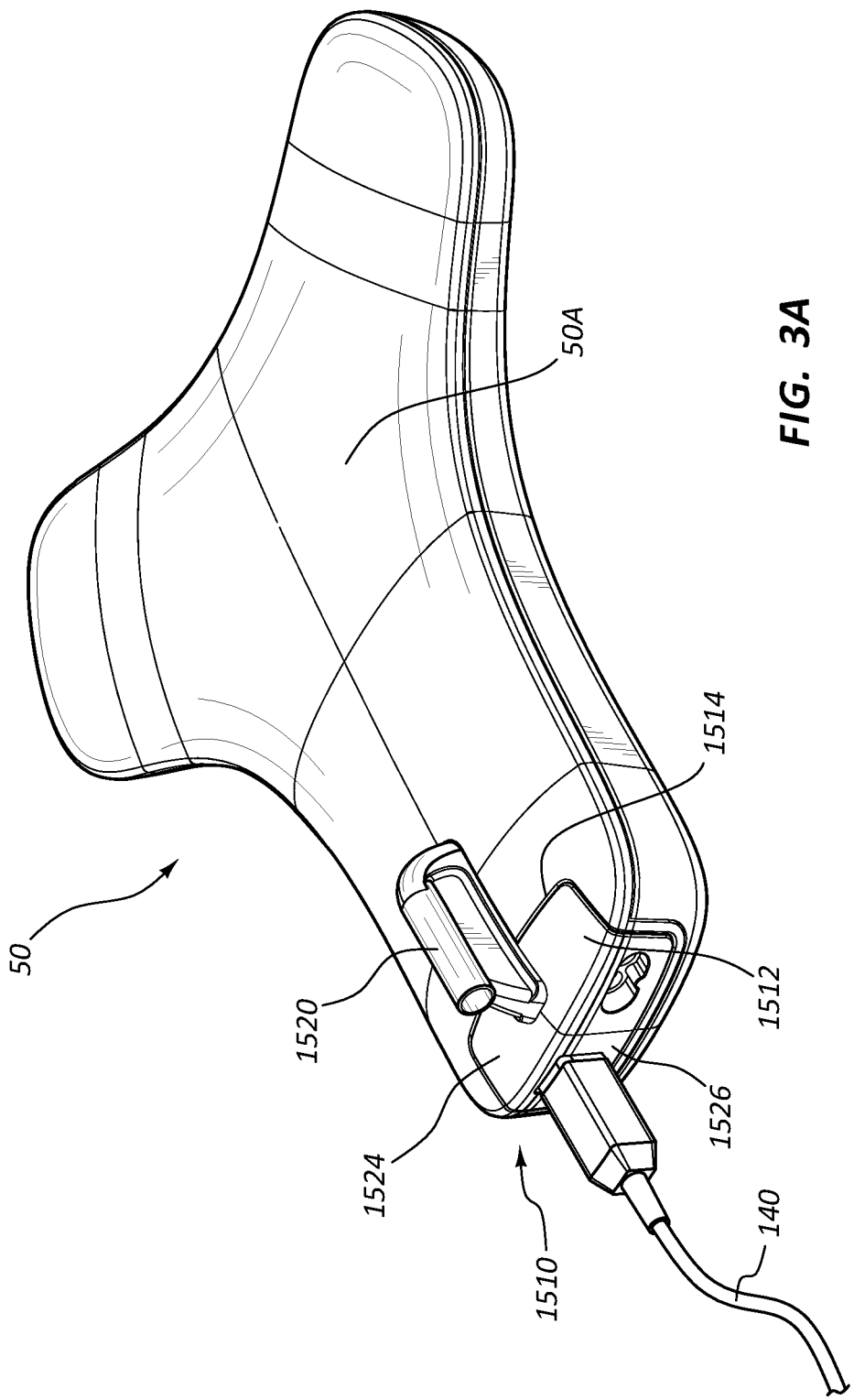

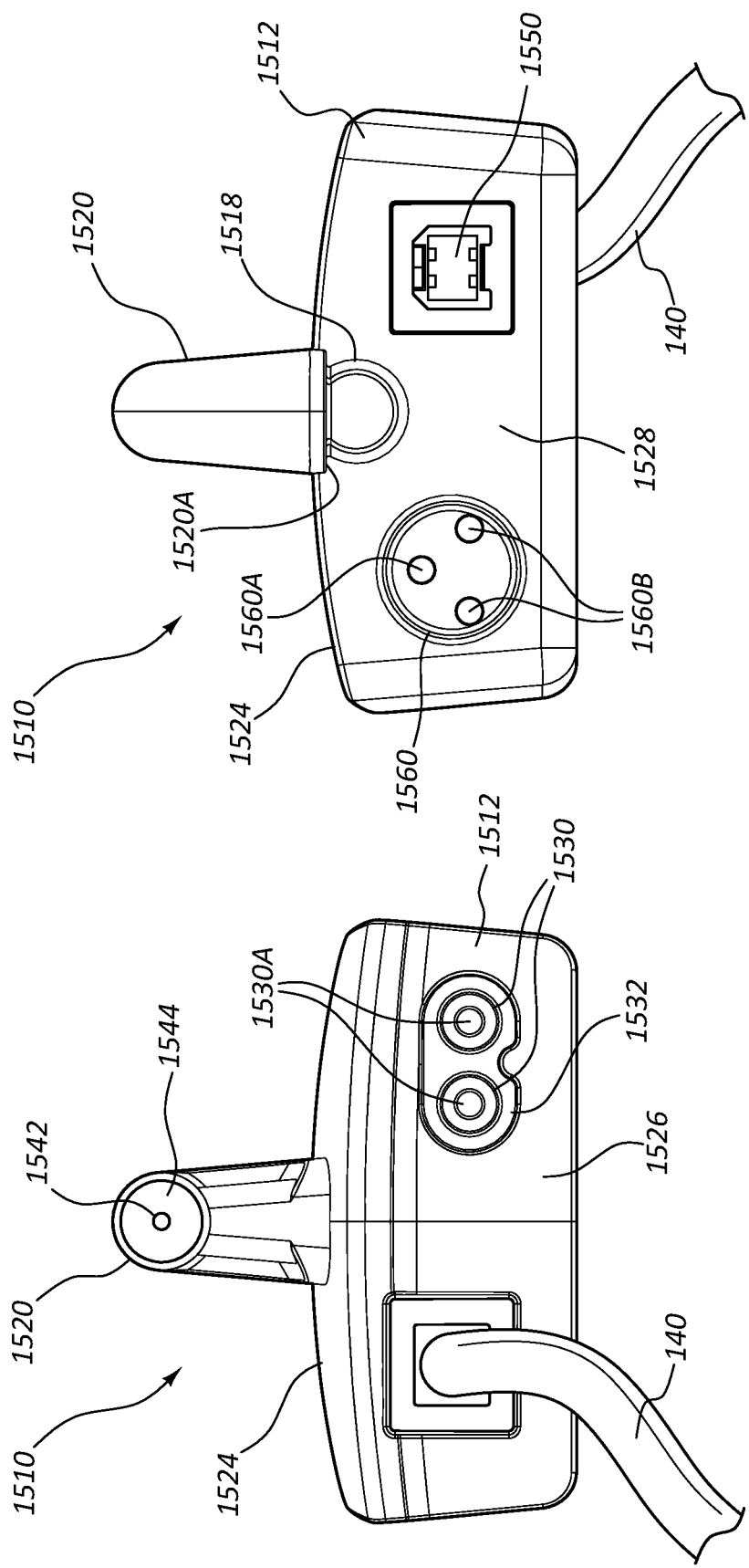

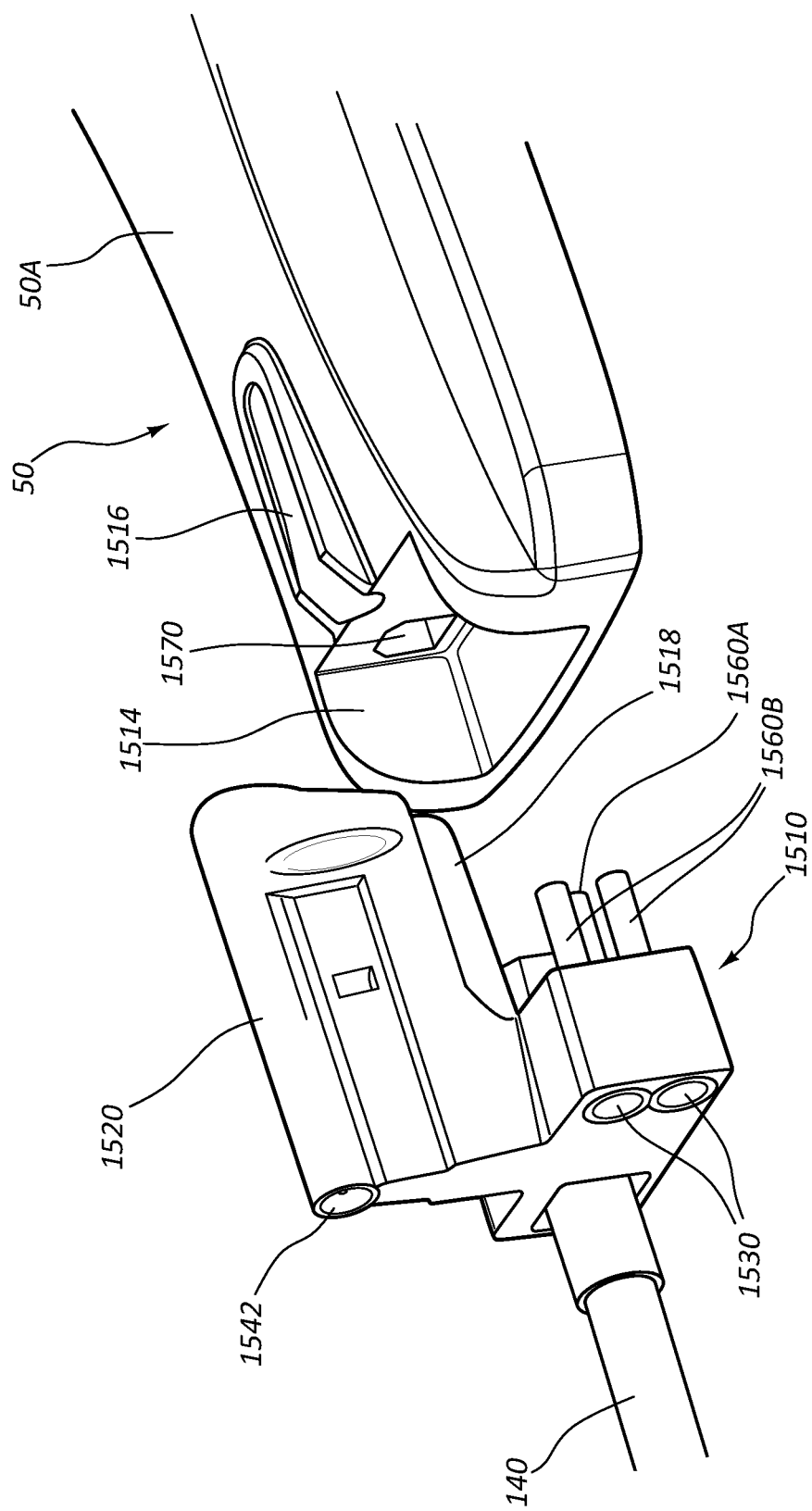

US 11,026,630 B2

CONNECTOR INTERFACE FOR ECG-BASED CATHETER POSITIONING SYSTEM

CROSS-REFERENCE TO RELATED APPLICATIONS

This application is a continuation of U.S. patent application Ser. No. 15/192,561, filed Jun. 24, 2016, now U.S. Pat. No. 10,349,890, which claims the benefit of U.S. Provisional Application No. 62/185,477, filed Jun. 26, 2015, and titled "Interface Connector for ECG-based Catheter Positioning System," each of which is incorporated herein by reference in its entirety.

BRIEF SUMMARY

Briefly summarized, embodiments of the present invention are directed to a connector interface that is configured to enable component interconnection with a location sensor of a catheter placement system. The catheter placement system is configured to assist a clinician in positioning a catheter in a desired location within a body of a patient, such as a lower $\frac{1}{3}^{rd}$ portion of the superior vena cava within the patient's vasculature.

In one embodiment, the location sensor assembly comprises a location sensor body for temporary placement on a portion of the patient body, and a connector interface. The connector interface is configured to removably attach to the location sensor and provide a plurality of electrically conductive pathways between the location sensor and additional components of the catheter placement system to enable the additional components to operably connect with the location sensor. The connector interface further includes a first connector configured to operably connect with a second connector of one of the additional components of the catheter placement system through a sterile barrier, such as a surgical drape, interposed between the first and second connectors.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 3A-3C depict various views of a location sensor of the catheter placement system of FIGS. 1 and 2;

FIGS. 4A-4C depict various views of a connector interface of the location sensor or FIGS. 3A-3C;

FIG. 11 depicts attachment of the connector interface of FIG. 10 with the location sensor of FIG. 9;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present disclosure are generally directed to a connector interface connector for use in interconnecting various elements of a catheter placement system. Use of the present interface connector enables various components of the catheter placement system to be replaced or interchanged while enabling other components to remain. This in turn reduces system cost and allows for a modular system design.

Figure 1:
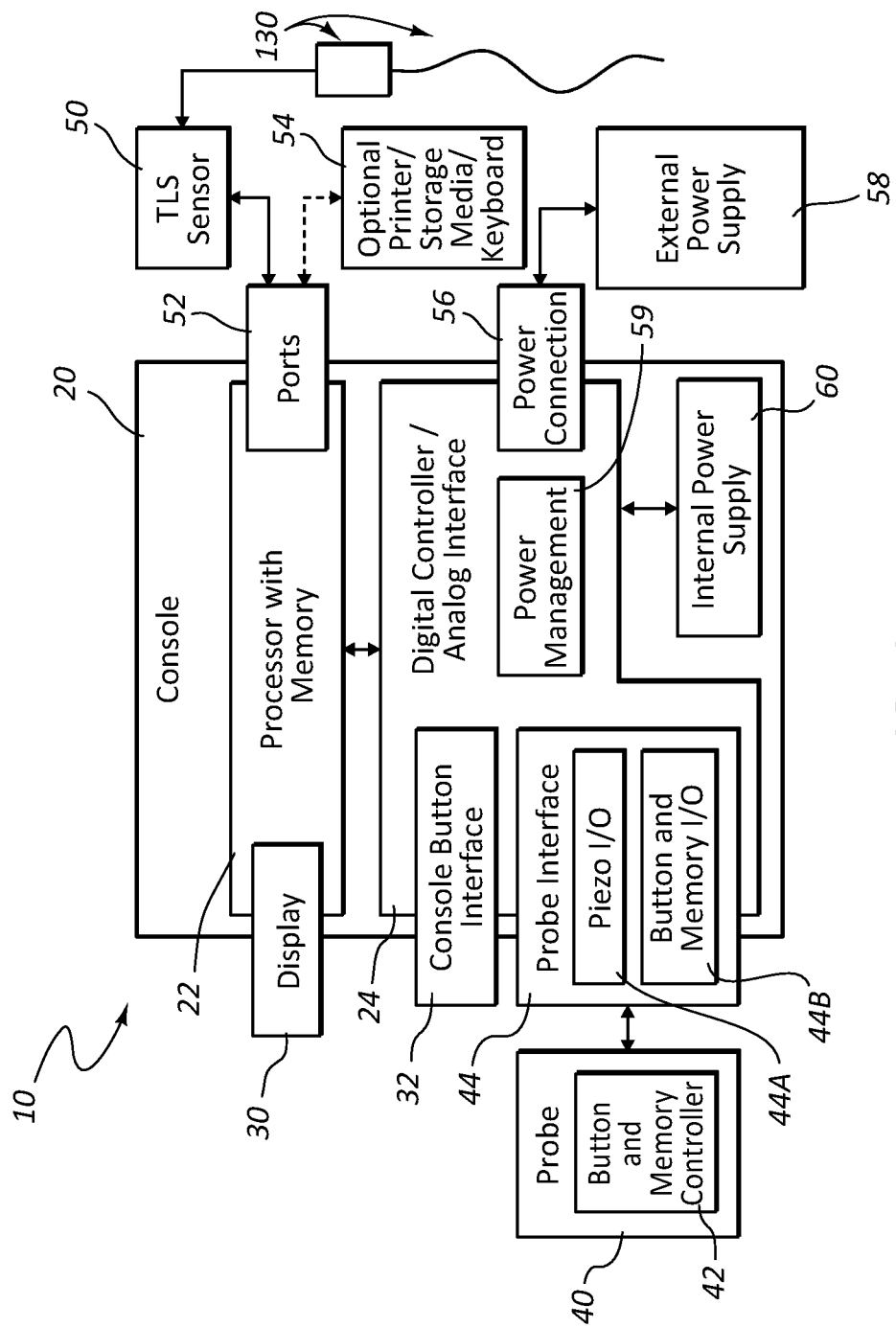
FIG. 1 is a block diagram of a catheter placement system according to one embodiment.
Figure 2:
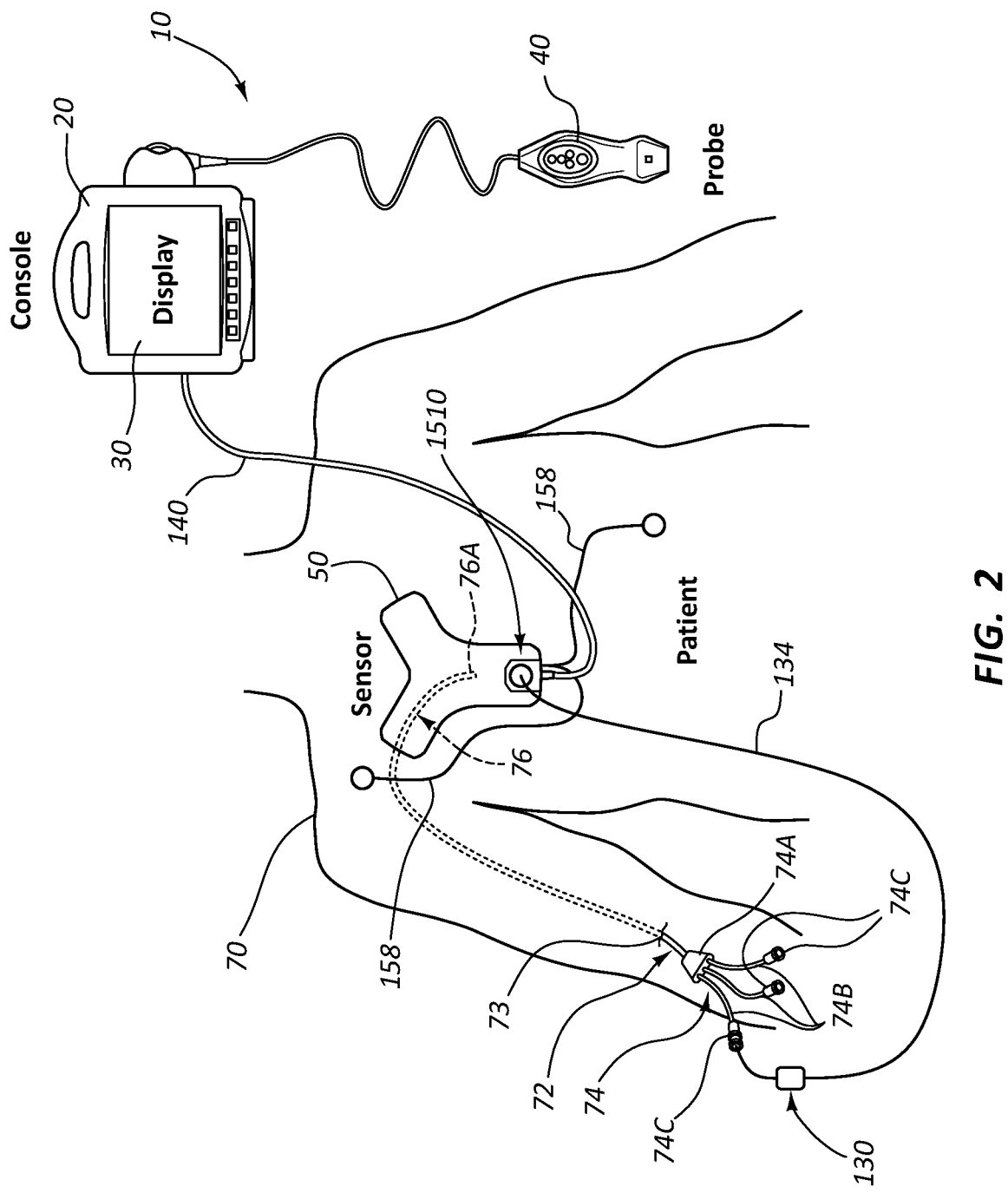
FIG. 2 is a simplified view of a patient and the catheter placement system of FIG. 1.

FIGS. 1 and 2 depict various details of a catheter placement system ("system" or "placement system"), generally designated at 10, which serves as one example environment wherein embodiments of the present disclosure can be practiced. The system 10 is employed to assist a clinician in the placement of a catheter or other medical device within the body of a patient, such as within the vasculature. In one embodiment, the system 10 enables a distal tip of a catheter to be placed within the patient vasculature in desired proximity to the heart using ECG signals produced by the patient's heart. In one embodiment, the medical device includes a catheter and the intended destination of the catheter within the patient body is such that the distal tip of the catheter is disposed in the lower $\frac{1}{3}^{rd}$ portion of the superior vena cava ("SVC"). The guidance and placement system analyzes the ECG signals of the patient to determine when the catheter has reached its intended destination within the vasculature, then notifies the clinician via a display, for instance. Thus, the system includes an ECG modality for assisting in medical device placement within the patient.

In one embodiment, the above-referenced ECG guidance modality of the system 10 is accompanied by an ultrasound ("US") modality to assist with initial insertion of the medical device into the body, and a magnetic element-based tracking, or tip location system ("TLS") modality to track the position and orientation of the medical device as it advances toward its intended destination.

As mentioned, FIGS. 1 and 2 depict various components of the system 10 in accordance with one example embodiment. As shown, the system 10 generally includes a console 20, display 30, probe 40, and sensor 50, each of which is described in further detail below.

FIG. 2 shows the general relation of these components to a patient 70 during a procedure to place a catheter 72 into the patient vasculature through a skin insertion site 73. FIG. 2 shows that the catheter 72 generally includes a proximal portion 74 that remains exterior to the patient and a distal portion 76 that resides within the patient vasculature after placement is complete. In the present embodiment, the system 10 is employed to ultimately position a distal tip 76A of the catheter 72 in a desired position within the patient vasculature. In one embodiment, the desired position for the catheter distal tip 76A is proximate the patient's heart, such as in the lower one-third ($\frac{1}{3}^{rd}$) portion of the Superior Vena Cava ("SVC"). Of course, the system 10 can be employed to place the catheter distal tip in other locations. The catheter proximal portion 74 further includes a bifurcation hub 74A that provides fluid communication between the one or more lumens of the catheter 72, one or more extension tubes 74B extending proximally from the hub, and corresponding connectors 74C for enabling connection to the catheter 72.

A processor 22, including non-volatile memory such as EEPROM for instance, is included in the console 20 for controlling system function during operation of the system 10, thus acting as a control processor. A digital controller/analog interface 24 is also included with the console 20 and is in communication with both the processor 22 and other system components to govern interfacing between the probe 40, sensor 50, and other system components.

The system 10 further includes ports 52 for connection with the sensor 50 and optional components 54 including a printer, storage media, keyboard, etc. The ports in one embodiment are USB ports, though other port types or a combination of port types can be used for this and the other interfaces connections described herein. A power connection 56 is included with the console 20 to enable operable connection to an external power supply 58. An internal battery 60 can also be employed, either with or exclusive of an external power supply. Power management circuitry 59 is included with the digital controller/analog interface 24 of the console to regulate power use and distribution.

The display 30 in the present embodiment is integrated into the console 20 and is used to display information to the clinician during the catheter placement procedure. In another embodiment, the display may be separate from the console. As will be seen, the content depicted by the display 30 changes according to which mode the catheter placement system is in: US, TLS, or in other embodiments, ECG tip confirmation. In one embodiment, a console button interface 32 and buttons included on the probe 40 can be used to immediately call up a desired mode to the display 30 by the clinician to assist in the placement procedure. In one embodiment, information from multiple modes, such as TLS and ECG, may be displayed simultaneously. Thus, the single display 30 of the system console 20 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In one embodiment, the display 30 is an LCD device.

The probe 40 is employed in connection with the first modality mentioned above, i.e., ultrasound ("US")-based visualization of a vessel, such as a vein, in preparation for insertion of the catheter 72 into the vasculature. Such visualization gives real time ultrasound guidance for introducing the catheter into the vasculature of the patient and assists in reducing complications typically associated with such introduction, including inadvertent arterial puncture, hematoma, pneumothorax, etc.

As such, in one embodiment a clinician employs the first, US, modality to determine a suitable insertion site and establish vascular access, such as with a needle and introducer, then with the catheter. The clinician can then seamlessly switch, via button pushes on the probe button pad, to the second, TLS, modality without having to reach out of the sterile field. The TLS mode can then be used to assist in advancement of the catheter 72 through the vasculature toward an intended destination.

FIG. 1 shows that the probe 40 further includes button and memory controller 42 for governing button and probe operation. The button and memory controller 42 can include non-volatile memory, such as EEPROM, in one embodiment. The button and memory controller 42 is in operable communication with a probe interface 44 of the console 20, which includes a piezo input/output component 44A for interfacing with the probe piezoelectric array and a button and memory input/output component 44B for interfacing with the button and memory controller 42.

Note that while a vein is typically depicted on the display 30 during use of the system 10 in the US modality, other body lumens or portions can be imaged in other embodiments. Note that the US mode can be simultaneously depicted on the display 30 with other modes, such as the TLS mode or ECG mode, if desired. In addition to the visual display 30, aural information, such as beeps, tones, etc., or vibratory/motion-based cues can also be employed by the system 10 to assist the clinician during catheter placement. Moreover, the buttons included on the probe 40 and the console button interface 32 can be configured in a variety of ways, including the use of user input controls in addition to buttons, such as slide switches, toggle switches, electronic or touch-sensitive pads, etc. Additionally, US, TLS, and ECG activities can occur simultaneously or exclusively during use of the system 10.

As just described, the handheld ultrasound probe 40 is employed as part of the integrated catheter placement system 10 to enable US visualization of the peripheral vasculature of a patient in preparation for transcutaneous introduction of the catheter. In the present example embodiment, however, the probe is also employed to control functionality of the TLS portion, or second modality, of the system 10 when navigating the catheter toward its desired destination within the vasculature as described below. Again, as the probe 40 is used within the sterile field of the patient, this feature enables TLS functionality to be controlled entirely from within the sterile field. Thus the probe 40 is a dual-purpose device, enabling convenient control of both US and TLS functionality of the system 10 from the sterile field. In one embodiment, the probe can also be employed to control some or all ECG-related functionality, or third modality, of the catheter placement system 10, as described further below.

The catheter placement system 10 further includes the second modality mentioned above, i.e., the magnetically-based catheter TLS, or tip location system. The TLS enables the clinician to quickly locate and confirm the position and/or orientation of the catheter 72, such as a peripherally-inserted central catheter ("PICC"), central venous catheter ("CVC"), or other suitable catheter or medical device, during initial placement into and advancement through the vasculature of the patient 70. Specifically, the TLS modality detects a magnetic field generated by a magnetic element-equipped tip location stylet, which is pre-loaded in one embodiment into a longitudinally defined lumen of the catheter 72, thus enabling the clinician to ascertain the general location and orientation of the catheter tip within the patient body. In one embodiment, the magnetic assembly can be tracked using the teachings of one or more of the following U.S. Pat. Nos. 5,775,322; 5,879,297; 6,129,668; 6,216,028; and 6,263,230. The contents of the afore-mentioned U.S. patents are incorporated herein by reference in their entireties. The TLS also displays the direction in which the catheter tip is pointing, thus further assisting accurate catheter placement. The TLS further assists the clinician in determining when a malposition of the catheter tip has occurred, such as in the case where the tip has deviated from a desired venous path into another vein.

Figure 6:
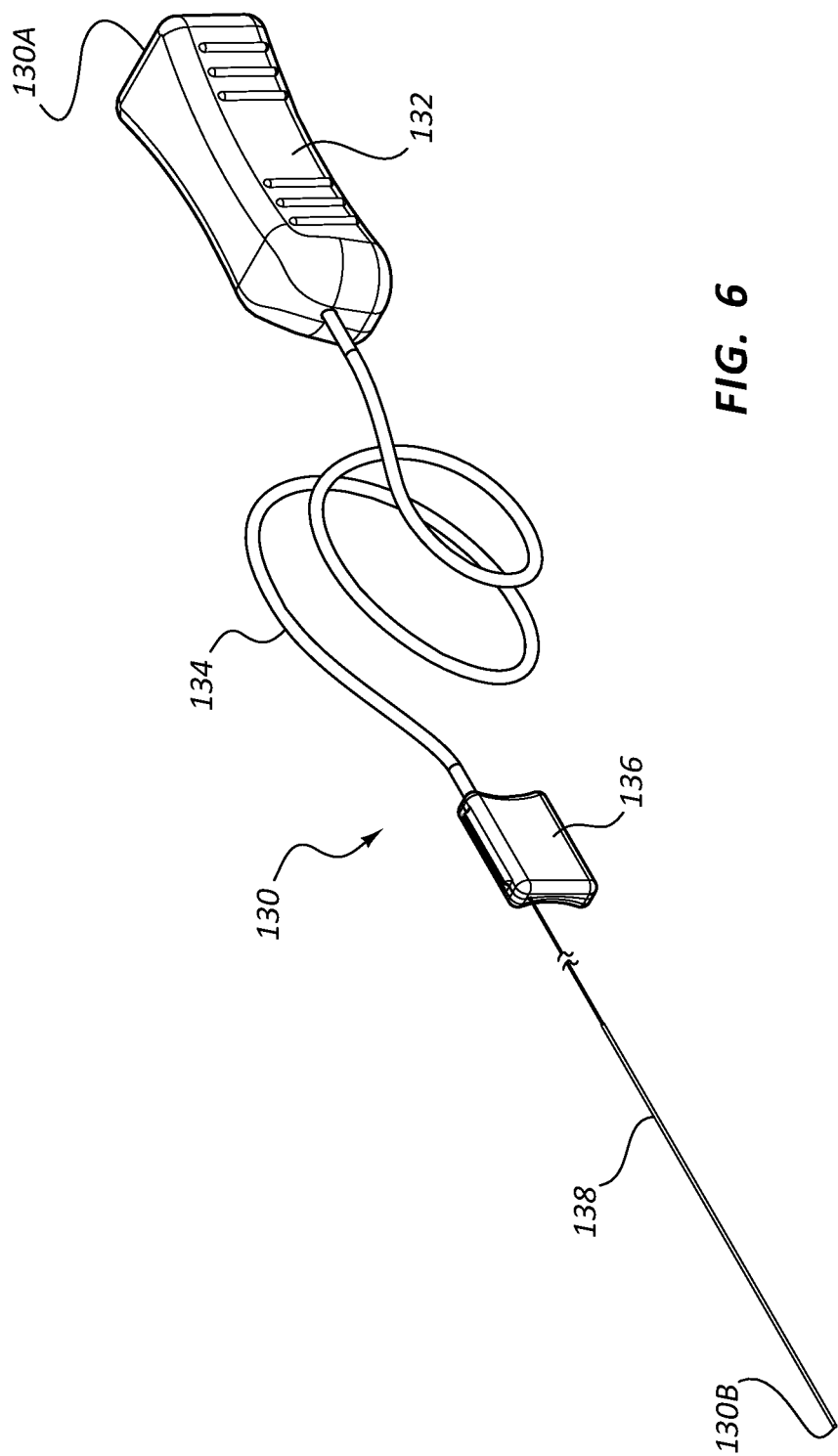
FIG. 6 is a perspective view of a stylet of the catheter placement system of FIGS. 1 and 2.

As mentioned, the TLS utilizes a stylet 130 to enable the distal end of the catheter 72 to be tracked during its advancement through the vasculature. In one embodiment and as shown in FIG. 6, the stylet 130 includes a proximal end 130A and a distal end 130B, with am included handle 136. A core wire 138 distally extends from the handle 136, and a tether 134 (for operably connecting the stylet 130 to the placement system 10) extends proximally from the handle. A magnetic assembly is disposed distally of the core wire 138. The magnetic assembly includes one or more magnetic elements disposed adjacent one another proximate the stylet distal end 130B and encapsulated by tubing. In the present embodiment, a plurality of magnetic elements is included, each element including a solid, cylindrically shaped ferromagnetic stacked end-to-end with the other magnetic elements. An adhesive tip can fill the distal tip of the tubing, distally to the magnetic elements.

Note that in other embodiments, the magnetic elements may vary from the design in not only shape, but also composition, number, size, magnetic type, and position in the stylet distal segment. For example, in one embodiment, the plurality of ferromagnetic magnetic elements is replaced with an electromagnetic assembly, such as an electromagnetic coil, which produces a magnetic field for detection by the sensor. Another example of an assembly usable here can be found in U.S. Pat. No. 5,099,845, entitled "Medical Instrument Location Means," which is incorporated herein by reference in its entirety. Yet other examples of stylets including magnetic elements that can be employed with the TLS modality can be found in U.S. Pat. No. 8,784,336, entitled "Stylet Apparatuses and Methods of Manufacture," which is incorporated herein by reference in its entirety. These and other variations are therefore contemplated by embodiments of the present invention. It should appreciated herein that "stylet" as used herein can include any one of a variety of devices configured for removable placement within a lumen of the catheter to assist in placing a distal end of the catheter in a desired location within the patient's vasculature. In one embodiment, the stylet includes a guidewire. As such, it is appreciated that stylets of other forms and configurations can also be acceptably used, in accordance with the present disclosure.

FIG. 2 shows disposal of the stylet 130 substantially within a lumen in the catheter 72 such that the proximal portion thereof extends proximally from the catheter lumen, through the bifurcation hub 74A and out through a selected one of the extension tubes 74B. So disposed within a lumen of the catheter, the distal end 130B of the stylet 130 in the present embodiment is substantially co-terminal with the distal catheter end 76A such that detection by the TLS of the stylet distal end correspondingly indicates the location of the catheter distal end. In other embodiments, other positional relationships between the distal ends of the stylet and catheter or medical device are possible.

The TLS sensor 50 (also referred to herein as a "location sensor") is employed by the system 10 during TLS operation to detect the magnetic field produced by the magnetic elements of the stylet 130. As seen in FIG. 2, the TLS sensor 50 is placed on the chest of the patient during catheter insertion. The TLS sensor 50 is positioned on the chest of the patient in a predetermined location, such as through the use of external body landmarks, to enable the magnetic field of the stylet magnetic elements, disposed in the catheter 72 as described above, to be detected during catheter transit through the patient vasculature. Again, as the magnetic elements of the stylet magnetic assembly are co-terminal with the distal end 76A of the catheter 72 in one embodiment (FIG. 2), detection by the TLS sensor 50 of the magnetic field of the magnetic elements provides information to the clinician as to the position and orientation of the catheter distal end during its transit.

In greater detail, the TLS sensor 50 is operably connected to the console 20 of the system 10 via a connection of a console cable 140 with one or more of the ports 52 of the console, as shown in FIG. 1. The console cable 140 attaches to the TLS sensor 50 in a manner to be described further below. Note that other connection schemes between the TLS sensor and the system console can also be used, without limitation. As just described, the magnetic elements are employed in the stylet 130 to enable the position of the catheter distal end 76A (FIG. 2) to be observable relative to the TLS sensor 50 placed on the patient's chest. Detection by the TLS sensor 50 of the stylet magnetic elements is graphically displayed on the display 30 of the console 20 during TLS mode. In this way, a clinician placing the catheter is able to generally determine the location of the catheter distal end 76A within the patient vasculature relative to the TLS sensor 50 and detect when catheter malposition, such as advancement of the catheter along an undesired vein, is occurring.

As discussed above, the system 10 includes additional functionality in the present embodiment wherein determination of the proximity of the catheter distal tip 76A relative to a sino-atrial ("SA") or other electrical impulse-emitting node of the heart of the patient 70 can be determined, thus providing enhanced ability to accurately place the catheter distal tip in a desired location proximate the node. Also referred to herein as "ECG" or "ECG-based tip confirmation," this third modality of the system 10 enables detection of ECG signals from the SA node in order to place the catheter distal tip in a desired location within the patient vasculature. Note that the US, TLS, and ECG modalities are seamlessly combined in the present system 10, but can be employed in concert or individually to assist in catheter placement. In one embodiment, it is understood that the ECG modality as described herein can be included in a stand-alone system without the inclusion of the US and TLS modalities. Thus, the environments in which the embodiments herein are described are understood as merely example environments and are not considered limiting of the present disclosure.

As described, the catheter stylet 130 is removably pre-disposed within the lumen of the catheter 72 being inserted into the patient 70 via the insertion site 73. The stylet 130, in addition to including a magnetic assembly for the magnetically-based TLS modality, includes a sensing component, i.e., an internal, intravascular ECG sensor assembly, proximate its distal end and including a portion that is co-terminal with the distal end of the catheter tip for intravascularly sensing ECG signals produced by the SA node, in the present embodiment when the catheter 72 and accompanying stylet 130 are disposed within the patient vasculature. The intravascular ECG sensor assembly is also referred to herein as an internal or "intravascular ECG sensor component," and the stylet 130 as an "ECG stylet."

As mentioned, the stylet 130 includes the tether 134 extending from its proximal end 130A that operably connects to the TLS sensor 50 in a manner to be described below, though other connection schemes to the system 10 are contemplated. As will be described in further detail, the stylet tether 134 permits ECG signals detected by the ECG sensor assembly included on a distal portion of the stylet 130 to be conveyed to the TLS sensor 50 during confirmation of the catheter tip location as part of the ECG signal-based tip confirmation modality.

External reference and ground ECG electrodes 158 attach to the body of the patient 70 in the present embodiment and are operably attached to the TLS sensor 50 to provide an external baseline ECG signal to the system 10 and to enable the system to filter out high level electrical activity unrelated to the electrical activity of the SA node of the heart, thus enabling the ECG-based tip confirmation functionality. As shown, in the present embodiment, one external electrode 158 is placed on the patient skin proximate the upper right shoulder ("right arm" placement) while another external electrode is placed proximate the lower left abdomen ("left leg" placement). This electrode arrangement provides a lead II configuration according to Einthoven's triangle of electrocardiography. Operable attachment of the external electrodes 158 with the sensor 50 in a manner to be described below enables the ECG signals detected by the external electrodes to be conveyed to the console 20 of the system 10 or to another suitable destination. As such, the external electrodes 158 serve as one example of an external ECG sensor component. Other external sensors for detecting a baseline ECG signal external to the patient body can also be employed in other embodiments. In addition, other electrode locations are also possible.

Together with the external ECG signal received from the external ECG sensor component (i.e., the external ECG electrodes 158 placed on the patient's skin), an internal, intravascular ECG signal sensed by the internal ECG sensor component (i.e., the stylet ECG sensor assembly of the stylet 130), is received by the TLS sensor 50 positioned on the patient's chest (FIG. 10) or other designated component of the system 10. The TLS sensor 50 and/or console processor 22 can process the external and internal ECG signal data to produce one or more electrocardiogram traces, including a series of discrete ECG complexes, on the display 30, as will be described. In the case where the TLS sensor 50 processes the external and internal ECG signal data, a processor is included therein to perform the intended functionality. If the console 20 processes the ECG signal data, the processor 22, controller 24, or other processor can be utilized in the console to process the data.

Figure 10:
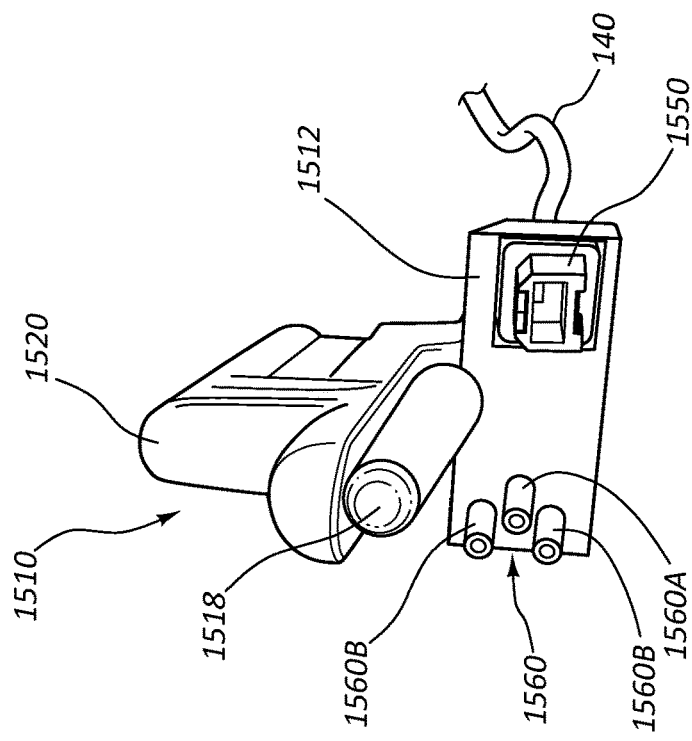
FIG. 10 is a perspective view of a connector interface for attachment to the location sensor of FIG. 9.

Thus, as it is advanced through the patient vasculature, the catheter 72 equipped with the stylet 130 as described above can advance under the TLS sensor 50, which is positioned on the chest of the patient as shown in FIG. 10. This enables the TLS sensor 50 to detect the position of the magnetic assembly of the stylet 130 (described further above), which is substantially co-terminal with the distal tip 76A of the catheter as located within the patient's vasculature. The detection by the TLS sensor 50 of the stylet magnetic assembly is depicted on the display 30 during ECG mode.

The display 30 can further depict during ECG mode one or more ECG electrocardiogram traces produced as a result of patient heart's electrical activity as detected by the external and internal ECG sensor components described above. In greater detail, the ECG electrical activity of the SA node, including the P-wave of the trace, is detected by the external and internal sensor components and forwarded to the TLS sensor 50 and console 20. The ECG electrical activity is then processed for depiction on the display 30, as will be described further below.

A clinician placing the catheter can then observe the ECG data, which assists in determining optimum placement of the distal tip 76A of the catheter 72, such as proximate the SA node, for instance. In one embodiment, the console 20 includes the electronic components, such as the processor 22 (FIG. 1), necessary to receive and process the signals detected by the external and internal sensor components. In another embodiment, the TLS sensor 50 can include the necessary electronic components processing the ECG signals.

As already discussed, the display 30 is used to display information to the clinician during the catheter placement procedure. The content of the display 30 changes according to which mode the catheter placement system is in: US, TLS, or ECG. Any of the three modes can be immediately called up to the display 30 by the clinician, and in some cases information from multiple modes, such as TLS and ECG, may be displayed simultaneously. In one embodiment, as before, the mode the system is in may be controlled by the control buttons included on the handheld probe 40, thus eliminating the need for the clinician to reach out of the sterile field (such as touching the button interface 32 of the console 20) to change modes. Thus, in the present embodiment the probe 40 is employed to also control some or all ECG-related functionality of the system 10. Note that the button interface 32 or other input configurations can also be used to control system functionality. Also, in addition to the visual display 30, aural information, such as beeps, tones, etc., can also be employed by the system to assist the clinician during catheter placement.

Note that further details regarding the system 10 can be found in U.S. Pat. No. 8,848,382, issued Sep. 30, 2014, and entitled "Apparatus and Display Methods Relating to Intravascular Placement of a Catheter," which is incorporated herein by reference in its entirety. It is further noted that the above-described catheter placement system is but example of a variety of placement systems that can benefit from the principles of the embodiments described herein.

Figure 3B:
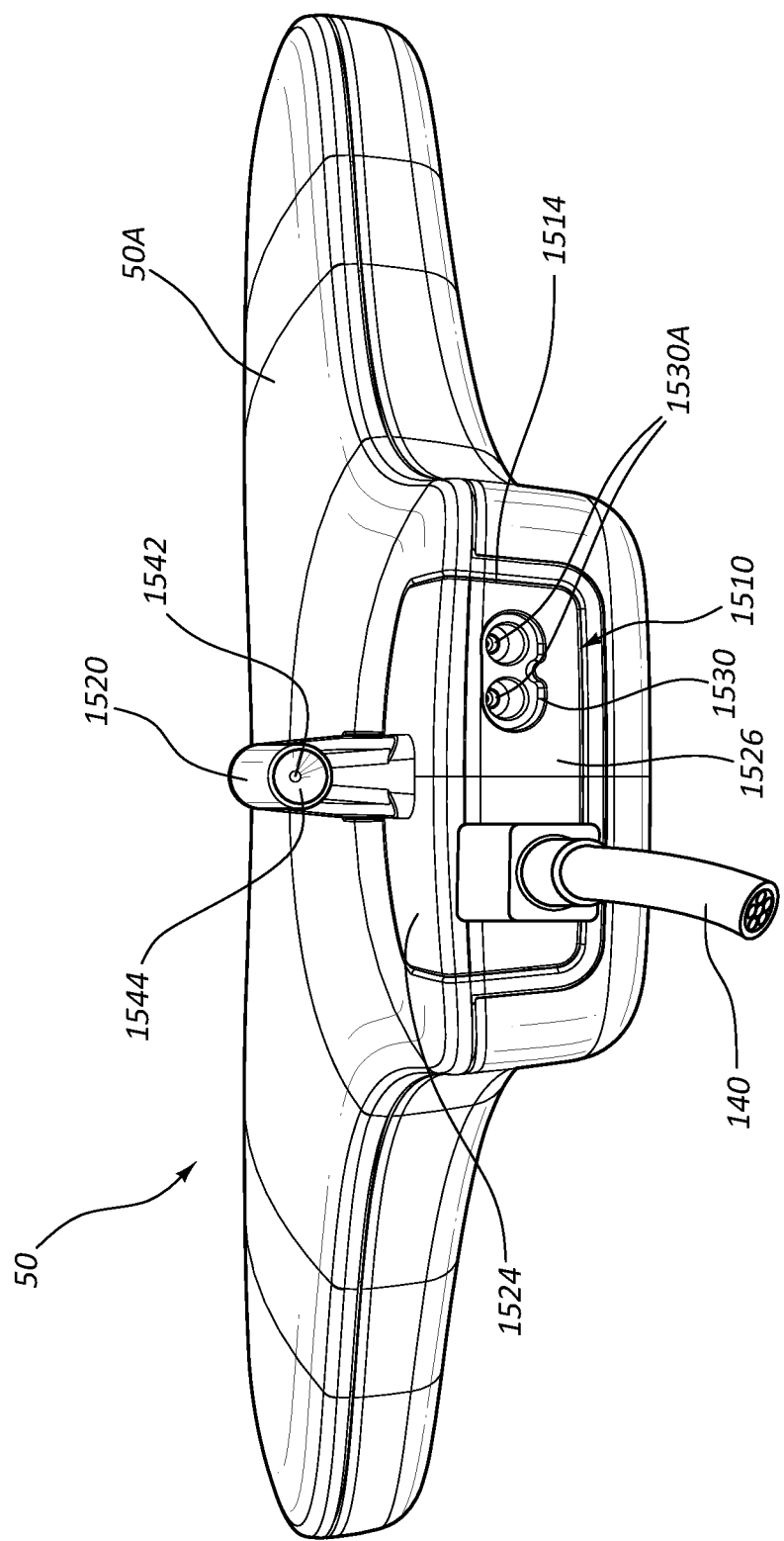
Figure 3C:
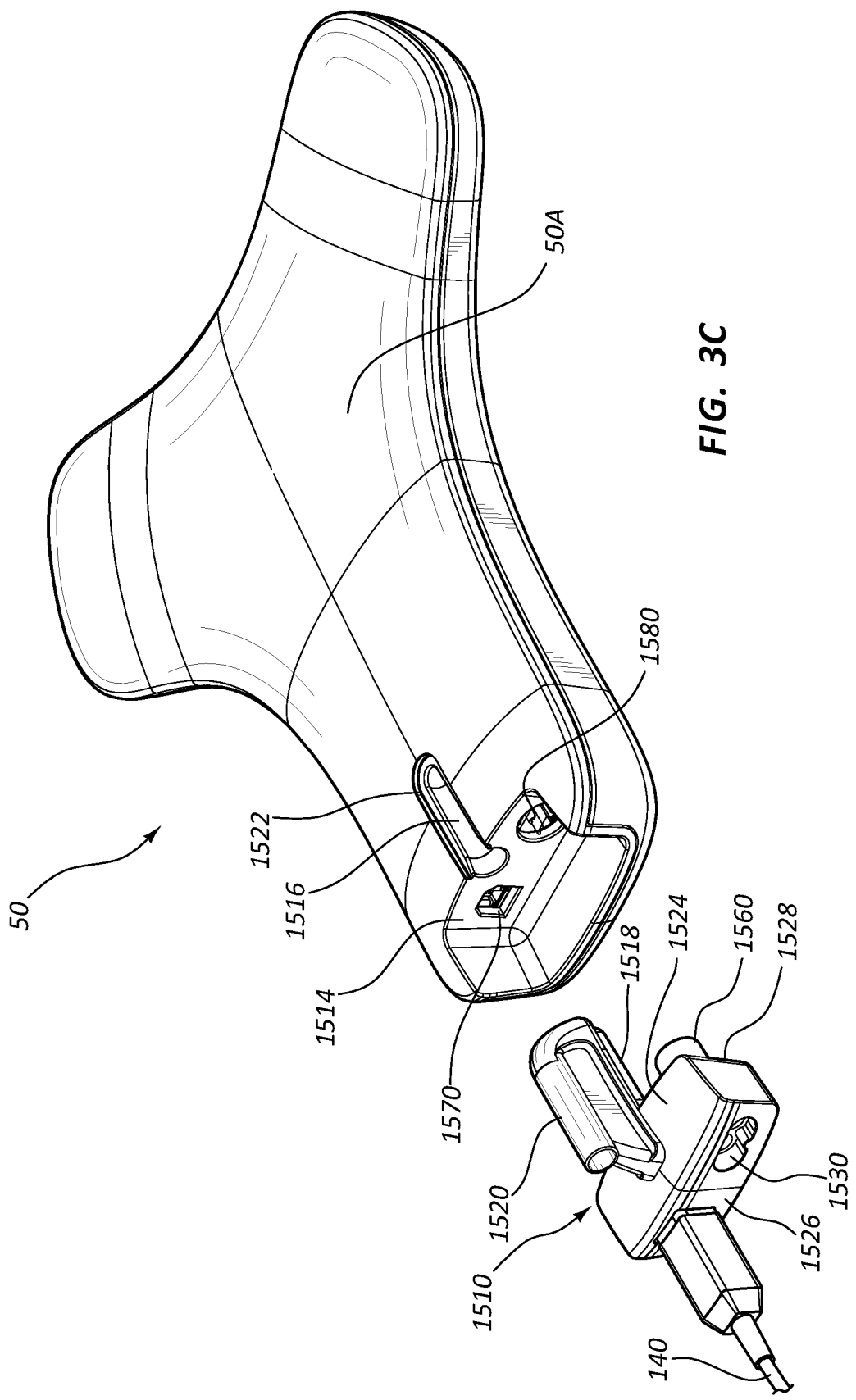

In view of the above discussion, reference is now made to FIGS. 3A-3C, which depict various details of the above-described TLS sensor 50, also referred to herein as a "location sensor." In particular, the location sensor 50 includes a connector interface ("interface") 1510 that is configured according to one embodiment. The interface 1510 is configured to enable interconnection of the location sensor 50 with various other catheter placement system components, including the ECG signal-sensing stylet 130 via the tether 134 (FIG. 6), the external ECG electrodes 158 (FIG. 2) via their respective lead wires ("leads"), and the console cable 140 that operably connects the location sensor with the console 20 of the system 10.

As shown, the interface 1510 includes a body 1512 that is configured to removably connect to the location sensor 50 within a pocket 1514 defined on a lower portion of the location sensor 50, from the perspective shown in FIG. 3A. The interface body 1512 includes a rail 1518 defined on a fin 1520 that is configured to be slidably received within a corresponding track 1516 defined on an outer surface 50A of the location sensor 50 proximate the pocket 1514, as shown in FIG. 3C. Other connective schemes can be employed in other embodiments. Also, the particular size, shape, and configuration of the interface 1510 can vary. A bottom portion 1520A of the fin 1520 is configured to be slidably received within a track perimeter 1522 defined about the track 1516 in order to secure the connection between the location sensor 50 and the interface 1510.

The interface body 1512 defines an outer surface 1524 that is shaped and configured so as to match the outer surface 50A of the location sensor 50 when the interface 1510 is attached to the location sensor. Of course, the particular shape and configuration of both the location sensor and the interface can vary from what is shown and described. Also, the particular connection point of the interface with the location sensor can vary. The interface body 1512 further defines an end surface 1528 that remains externally accessible when the interface 1510 is operably attached to the location sensor (FIGS. 3A, 3B), as well as an inner surface 1528 (FIGS. 3C, 4B, 4C) that is inaccessible when the interface is attached to the location sensor. As will be described, various connection points are included on both the end surface 1526 and the inner surface 1528 to enable various components of the catheter placement system 10 to operably connect with the location sensor 50. The size, shape, type, and number of connection points can vary from the below discussion.

Figure 4C:
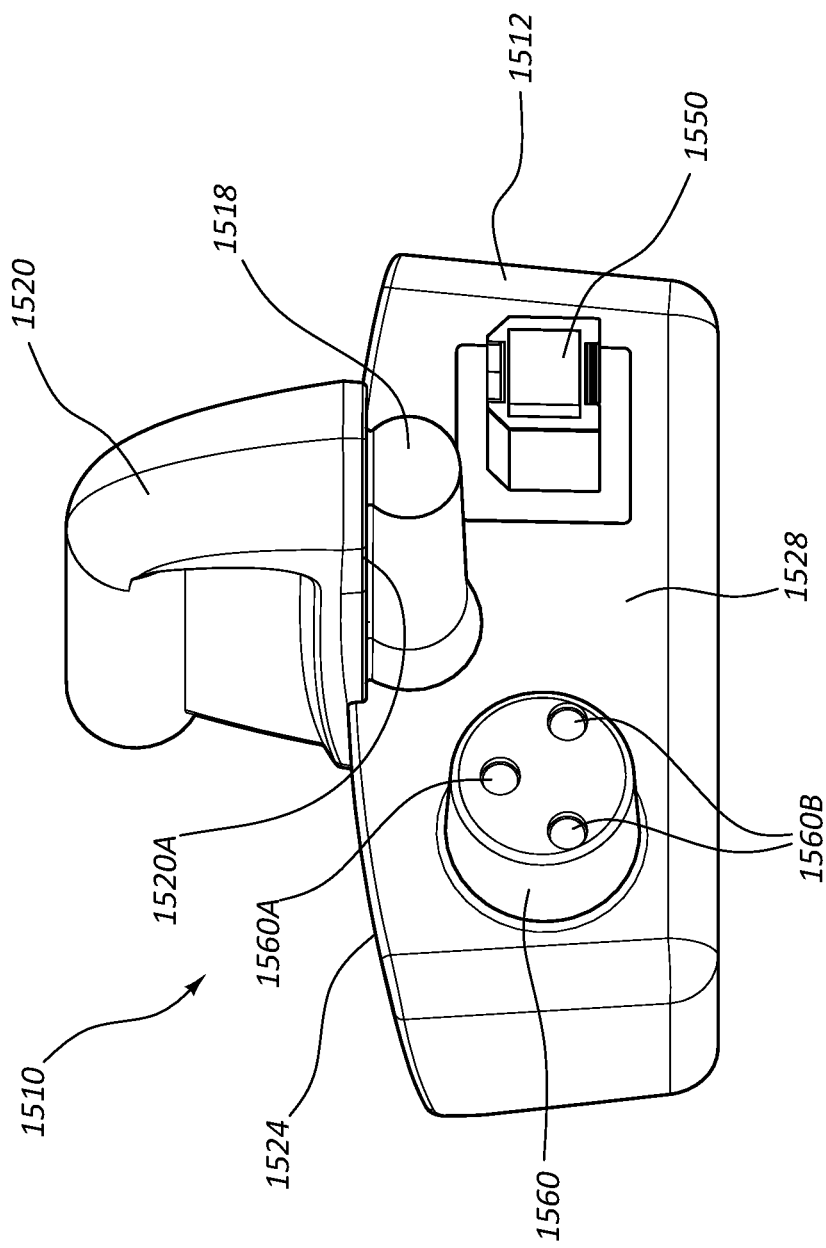

FIGS. 4A-4C depict further details regarding the interface 1510. As shown, the end surface 1526 includes various connection points for enabling interconnection with components of the catheter placement system 10. Specifically, the end surface 1526 includes a pair of ECG lead connector receptacles 1530 disposed in a recess 1532. The ECG lead connector receptacles 1530 each include a female contact 1530A sized and configured to receive therein a male connector end of the leads of the ECG electrodes 158. In the present embodiment, the recess 1532 is shaped so as to receive a dual connector that includes both male connector ends of the ECG electrodes 158 in a single plug, though other configurations are also possible for the ECG lead connection scheme.

FIG. 4A shows that the fin 1520 includes an ECG stylet wire receptacle 1542, surrounded by a centering cone 1544, for removably receiving therein a pin contact 170 (FIG. 7) of a tether connector 132 of the ECG stylet 130 (FIG. 6). Further details regarding connection of the ECG stylet 130 to the interface 1510 and the location sensor 50 are given further below.

FIG. 4A further shows that the console cable 140 is permanently attached so as to extend from the interface 1510, as shown. The length of the console cable 140 can vary according to need, but is sufficient in the present embodiment to extend between the location sensor 50 and the console 20, as shown in FIG. 2.

The inner surface 1528 of the interface 1510 includes various connection points for enabling interconnection of the aforementioned components with the location sensor. As shown, in FIGS. 4B and 4C, a USB type B plug 1550 of the console cable 140 extends from the interface inner surface 1528 to operably connect with a corresponding USB type B receptacle 1570 (FIG. 5) disposed in the pocket 1514 when the interface 1510 mates with the location sensor 50. Similarly, a rounded, cylindrical ECG plug 1560 extends from the interface inner surface 1528 to operably connect with a corresponding, cylindrically shaped ECG receptacle 1580 defined in the pocket 1514 when the interface 1510 mates with the location sensor 50.

Figure 8A:
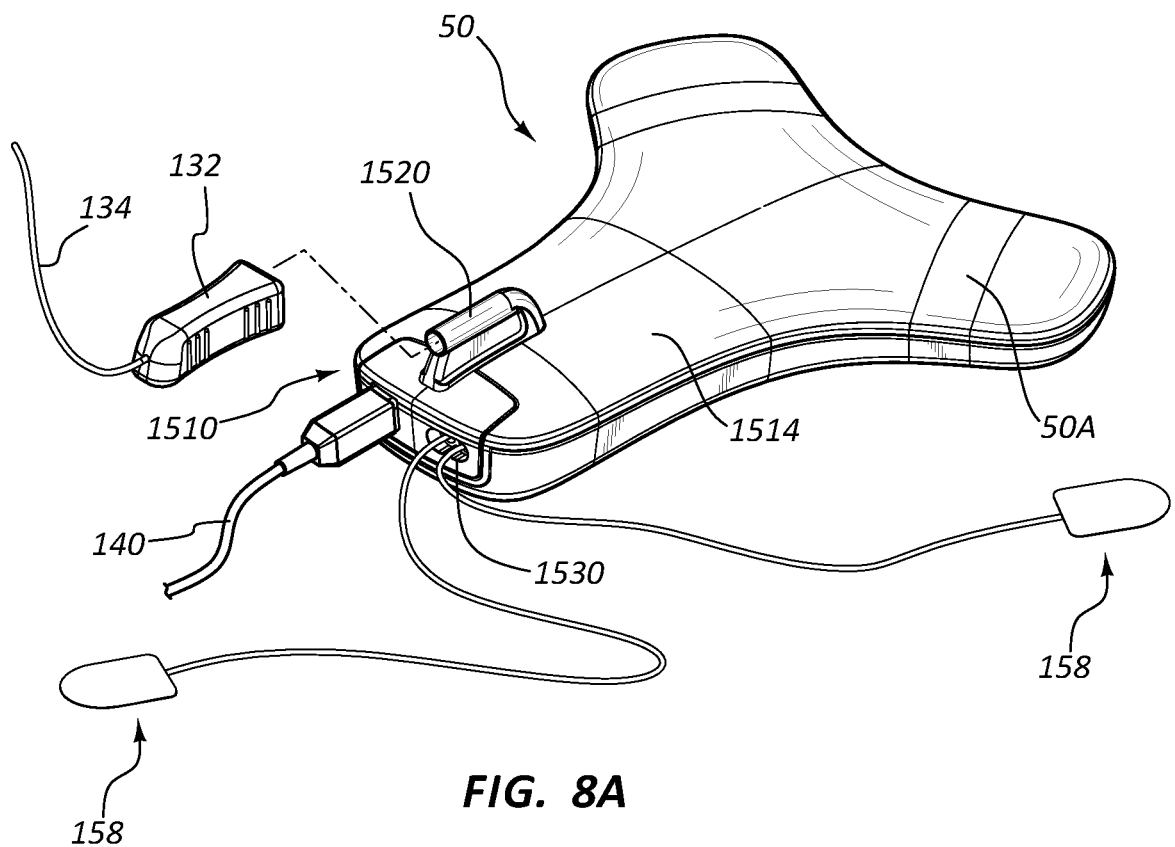
FIGS. 8A and 8B depict various views of the connection of the tether connector of FIG. 6 with the location sensor of FIGS. 3A-3C.
Figure 8B:
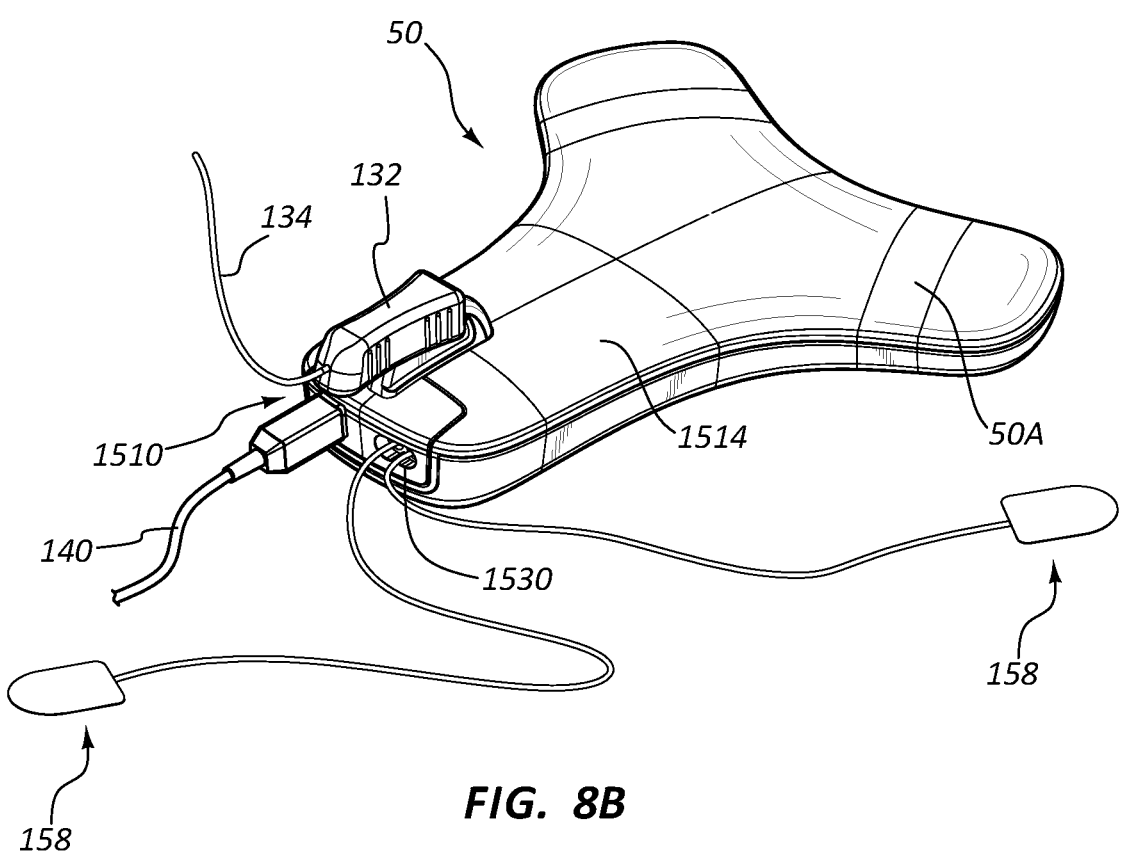

Specifically, the ECG plug 1560 includes an ECG stylet wire contact 1560A that is operably connected with the ECG stylet wire receptacle 1542 on the fin 1520, as well as two ECG lead contacts 1560B that are operably connected with the ECG lead electrical contacts 1530A in the ECG lead receptacle 1530 included on the interface end surface 1526. In the present embodiment, the ECG lead contacts 1560B are integrally formed with the ECG lead contacts 1530A and are formed as sleeves so as to receive corresponding ECG lead pins 1580B disposed in the ECG receptacle 1580. The ECG receptacle 1580 further includes an ECG stylet pin 1580A for operably connecting with the sleeve-type ECG stylet wire contact 1560A of the ECG plug 1560. FIGS. 3A, 8A, and 8B show the manner of attachment of the interface 1510 within the pocket 1514 of the location sensor 50.

Figure 7:
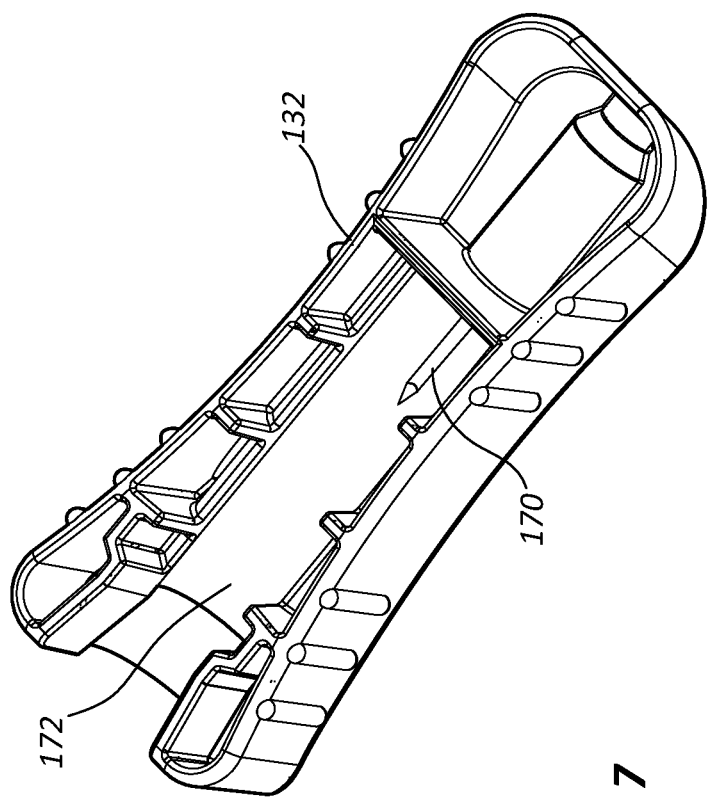
FIG. 7 is a perspective view of a tether connector of the stylet of FIG. 6.

FIGS. 6 and 7 show details of the ECG stylet 130, including the pin contact 170 included in a channel 172 of the tether connector 132, as described further above. As shown in FIGS. 8A and 8B, the tether connector 132 is slid over the fin 1520 in a snug friction fit such that the pin contact 170 is received within the ECG stylet wire receptacle 1542. The ECG stylet wire receptacle 1542 is operably connected within the interface body 1512 with the ECG stylet wire contact 1560A. Thus, this connection establishes an electrically conductive pathway from the ECG stylet 130 to the location sensor 50 via the operable connections of the pin contact 170 with the ECG stylet wire receptacle 1542, and the ECG stylet wire contact 1560A (FIG. 4C) of the interface 1510 with the ECG stylet wire pin 1580A (FIG. 5) of the location sensor. This, in turn, enables ECG signals detected by the ECG stylet 130 to be conveyed to the location sensor 50 and, in one embodiment, the console 20 for processing by the system 10.

Correspondingly, FIG. 8B shows the connector ends of the leads of the ECG external electrodes 158 received within the ECG lead connector receptacles 1530 of the interface 1510 such that they each operably connect with a corresponding one of the electrical contacts 1530A therewithin. Thus, conductive pathways are established from the ECG external electrodes 158 to the location sensor via the operable connections of the connector ends of the ECG external electrode leads with ECG lead connector receptacles 1530, and the ECG lead contacts 1560B (FIG. 4C) of the interface 1510 with the ECG lead pins 1580B (FIG. 5) of the location sensor.

Figure 5:
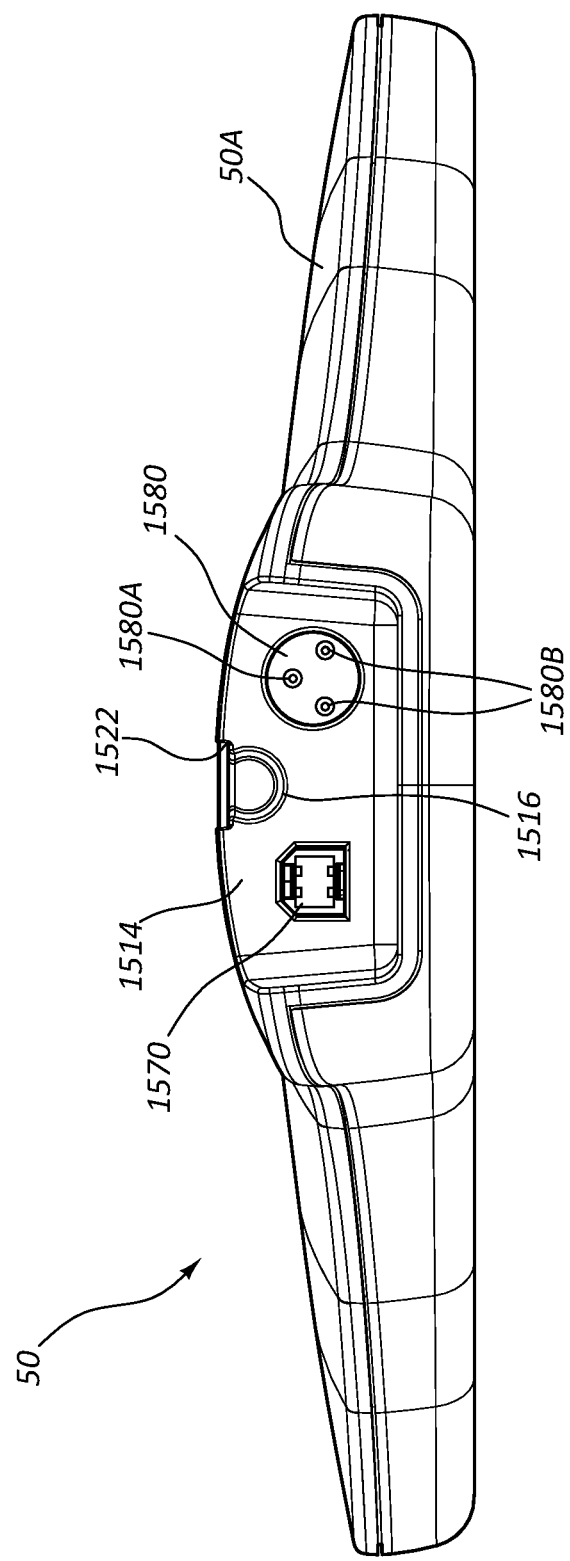
FIG. 5 is an end view of the location sensor of FIGS. 3A-3C.

Also, conductive pathways are established from the location sensor 50 to the console 20 (FIGS. 1, 2) via the operable connection of the console cable 140, namely, the operable connection of its male connector 1550 of the interface 1510 (FIG. 4C) with the receptacle 1570 of the location sensor (FIG. 5). Note that while shown as a USB-type cable, the console cable can include other styles, types, form factors, etc.

Figure 12:
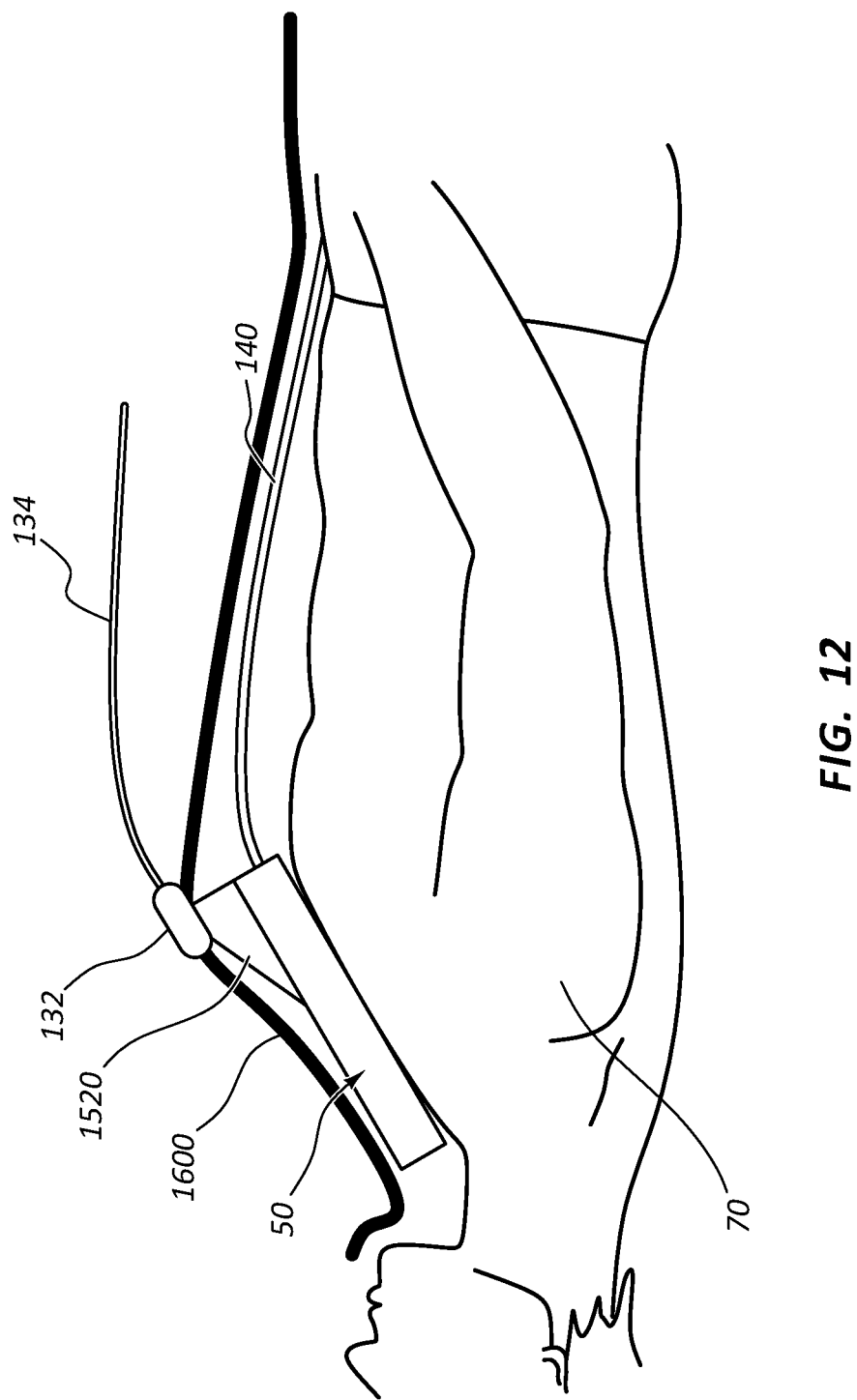
FIG. 12 shows a side view of a patient with the location sensor of FIG. 8B placed on the patient.

In the above-described configurations, therefore, the location sensor and attached components are ready for use by the catheter placement system 10, in one embodiment. Indeed, FIG. 12 shows the manner of use of the location sensor 50 when connected with the various components described above during a catheter insertion procedure using the catheter placement system 10. Note that the tether connecter 132 is configured to pierce a sterile drape 1600 (which is placed over the patient during catheter insertion procedures) such that regions above the drape are considered a sterile environment, while the location sensor 50, the fin 1520, and the console cable 140 are not considered sterile. The manner in which the tether connector 132 is able to pierce the drape 1600 and operably connect with the location sensor 50 enables such a connection without compromising the sterility of the sterile field.

Note that the various connecting components described with the above electrically conductive connections can vary in size, type, number, etc., from what is discussed herein. Note further that in the present embodiment attachment of the interface 1510 with the location sensor 50 is maintained via the friction fit of the various electrical connections between the interface and the location sensor, as just discussed above. In another embodiment, additional features can be included on one or both of the interface body 1512 and the location sensor 50 to provide a friction fit or other type of securement to maintain attachment between the interface and the location sensor.

Figure 9:
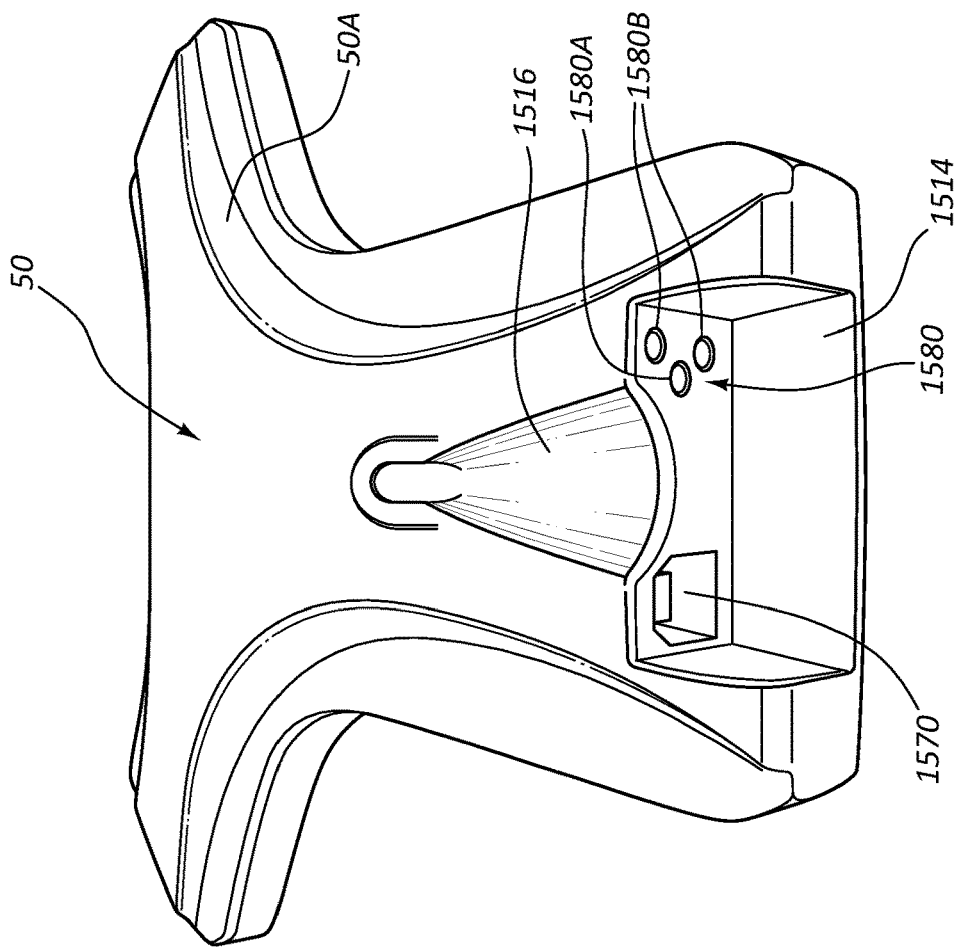
FIG. 9 is a perspective view of a location sensor according to one embodiment.

FIGS. 9-11 depict the interface 1510 according to another embodiment, wherein the ECG stylet wire contact 1560A and the two ECG lead contacts 1560B discretely extend from interface body 1512 instead of being included in a male plug (FIG. 10). Correspondingly, the ECG stylet wire pin 1580A and the two ECG lead pins 1580B of the location sensor 50 are discretely positioned instead of grouped within a receptacle in the location sensor pocket 1514 (FIG. 9). Also, note that the shape and configuration of the track 1516 of the location sensor 50 (FIG. 9) differs from that of the previous embodiment. These and other modifications are therefore contemplated.

Figure 13:
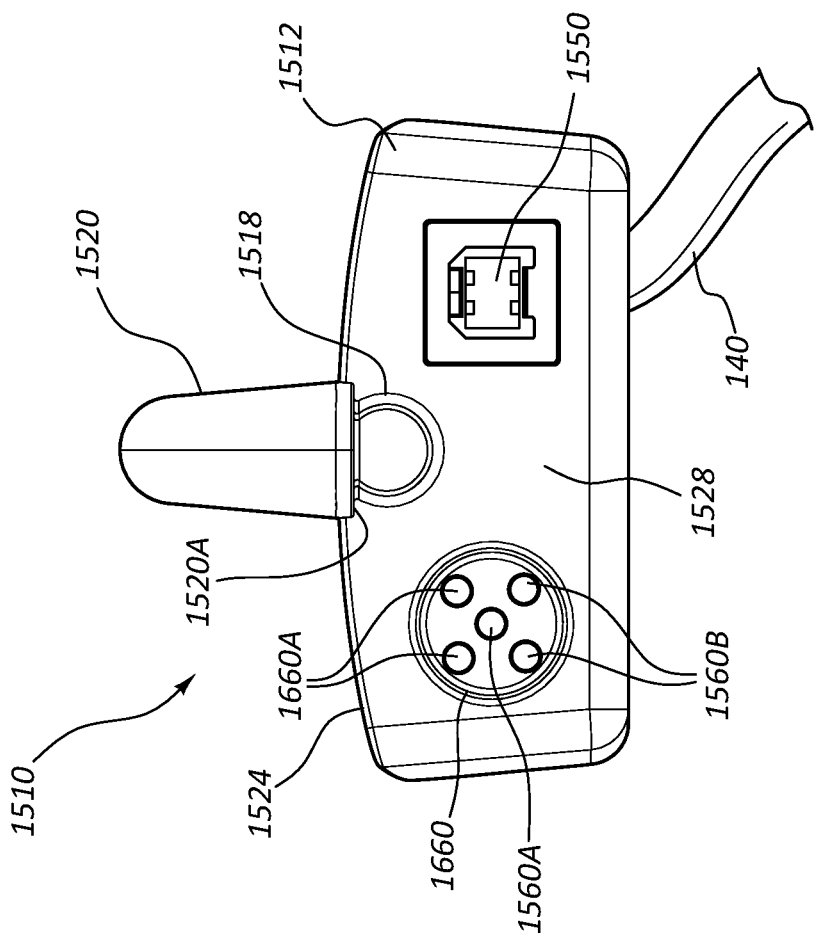
FIG. 13 is an end view of a connector interface according to one embodiment.

FIG. 13 shows an interface connector configuration according to another embodiment, wherein a connector block 1660 includes not only the ECG stylet wire contact 1560A and the ECG lead contacts 1560B, but also two electromagnetic contacts 1660A for providing power to an electromagnet element disposed in the ECG stylet 130 to be used when the system 10 is in TLS mode, described above. The particular arrangement and configuration of the various connectors can vary from what is shown here.

It is noted that the interface 1510 in one embodiment is reusable for multiple catheter insertion procedures, but is easily removable and replaceable should the need arise, such as in cases where damage to the wires or cables of the catheter insertion system 10 have been damaged due to use, accident, or repeated cleaning cycles. This, in turn enables replacement without the need to replace the entire location sensor, which can involve considerably more cost. Further, it is appreciated that the ECG stylet 130 and the external ECG electrodes and their leads are disposable and are disposed of after a single catheter insertion is complete. The console cable in one embodiment is permanently attached with the interface 1510 and thus is reusable. Also, though described here as employed with a location sensor, the interface in other embodiments can be employed to operably connect with other types of medical devices where interconnections as are enabled by the interface as described herein are needed. Further, note that various types of electrical connectors can be used to operably connect the various components described herein, including circuit board-edge connectors, peg and cuff-type connectors, type-C and other types of USB connectors, spring-loaded pins for pressing against conductive pads, etc. These and other connectors are therefore contemplated.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A connector interface designed to connect components of a catheter placement system to a location sensor of the catheter placement system, the connector interface comprising:
    a console connection interface designed for mating with a console port of the location sensor;
    an electrocardiogram (ECG) connection interface plug designed for mating with an ECG port receptacle of the location sensor; and
    a stylet connection interface designed for mating with a stylet connector recess of the location sensor,
    wherein the connector interface enables simultaneous mating of the console connection interface, the ECG connection interface plug, and the stylet connection interface to the location sensor.

2. The connector interface according to claim 1, wherein the stylet connection interface comprises a fin portion.

3. The connector interface according to claim 2, wherein the fin portion includes a receptacle configured to receive therein a male connector of an ECG stylet of the catheter placement system.

4. The connector interface according to claim 3, wherein the location sensor includes at least one sensor configured to detect a magnetic element included with the ECG stylet of the catheter placement system.

5. The connector interface according to claim 1, wherein the connector interface further comprises a recess including one or more ECG lead contacts in communication with the ECG connection interface plug.

6. The connector interface according to claim 1, further comprising a USB cable that operably connects the location sensor to a console of the catheter placement system.

7. The connector interface according to claim 6, wherein the USB cable is permanently attached to the connector interface.

8. The connector interface according to claim 1, wherein the location sensor is designed to be temporarily disposed on a chest portion of a patient.

9. The connector interface according to claim 1, wherein the connector interface is removable from the location sensor and is designed for multiple uses.

10. The connector interface according to claim 1, wherein the console connection interface is a universal serial bus (USB) type B plug, and wherein the console port of the location sensor is a USB type B receptacle.

11. The connector interface according to claim 10, wherein the stylet connection interface is a rail, wherein the stylet connector recess of the location sensor is a track, and wherein the rail is designed to slide in the track.

* * * * *